(12) United States Patent  (10) Patent No.: US 8,246,799 B2
Oliver et al.  (45) Date of Patent: Aug. 21, 2012

(54) DEVICES AND METHODS FOR ANALYZING BIOMOLECULES AND PROBES BOUND THERETO

(75) Inventors: John S. Oliver, Bristol, RI (US); Petre Ianakiev, Medford, MA (US)

(73) Assignee: Nabsys, Inc., Providence, RI (US)

( * ) Notice: Subject to any disclaimer, the term of this patent is extended or adjusted under 35 U.S.C. 154(b) by 110 days.

(21) Appl. No.: 12/789,817

(22) Filed: May 28, 2010

(65) Prior Publication Data
US 2010/0310421 A1 Dec. 9, 2010

Related U.S. Application Data

(60) Provisional application No. 61/181,907, filed on May 28, 2009, provisional application No. 61/318,048, filed on Mar. 26, 2010.

(51) Int. Cl.
*G01N 27/26* (2006.01)
(52) U.S. Cl. ............. 204/403.01; 435/6.1; 435/6.11; 435/6.13; 435/7.1; 435/6.18; 422/82.01; 204/450; 204/452; 204/549; 977/702; 977/925
(58) Field of Classification Search ............ 422/83; 204/403.01; 977/702, 925
See application file for complete search history.

(56) References Cited

U.S. PATENT DOCUMENTS

| | | | |
|---|---|---|---|
| 5,314,829 A | 5/1994 | Coles | |
| 5,405,519 A | 4/1995 | Schwartz | |
| 5,427,663 A | 6/1995 | Austin et al. | |
| 5,539,082 A | 7/1996 | Nielsen et al. | |
| 5,560,811 A | 10/1996 | Briggs et al. | |
| 5,599,664 A | 2/1997 | Schwartz | |
| 5,681,947 A | 10/1997 | Bergstrom et al. | |
| 5,683,881 A | 11/1997 | Skiena | |
| 5,720,928 A | 2/1998 | Schwartz | |
| 5,773,571 A | 6/1998 | Nielsen et al. | |
| 5,795,782 A | 8/1998 | Church et al. | |
| 5,837,115 A | 11/1998 | Austin et al. | |
| 5,908,745 A | 6/1999 | Mirzabekov et al. | |
| 5,972,619 A | 10/1999 | Drmanac et al. | |
| 6,015,714 A | 1/2000 | Baldarelli et al. | |
| 6,020,599 A | 2/2000 | Yeo | |
| 6,025,891 A | 2/2000 | Kim | |

(Continued)

FOREIGN PATENT DOCUMENTS

DE  19936302  2/2001

(Continued)

OTHER PUBLICATIONS

Golomb et al. (Applications of numbered undirected graphs, Proc. IEEE, vol. 65, No. 4, pp. 562-570, 1977).*

(Continued)

*Primary Examiner* — Sally Merkling
(74) *Attorney, Agent, or Firm* — Goodwin Procter LLP

(57) ABSTRACT

Devices and methods for detecting the length of analytes and/or sequencing analytes are provided in which two or more electrical signals are obtained as an analyte traverses a nanopore or fluidic channel. Detection of the relative position of probes hybridized to a biomolecule and/or the length of the analyte (e.g., a biomolecule) rely on detection events to determine a distance associated with the biomolecule. Multiple signals may be obtained (e.g., as functions of time) corresponding to a plurality of detector volumes at known locations along a fluidic channel through which the biomolecule passes, and the distances may be determined from the multiple signals.

7 Claims, 46 Drawing Sheets

U.S. PATENT DOCUMENTS

| | | | |
|---|---|---|---|
| 6,084,648 A | 7/2000 | Yeo |
| 6,100,949 A | 8/2000 | Kim |
| 6,108,666 A | 8/2000 | Floratos et al. |
| 6,128,051 A | 10/2000 | Kim et al. |
| 6,147,198 A | 11/2000 | Schwartz |
| 6,150,089 A | 11/2000 | Schwartz |
| 6,174,671 B1 | 1/2001 | Anantharaman et al. |
| 6,182,733 B1 | 2/2001 | McReynolds |
| 6,210,891 B1 | 4/2001 | Nyren et al. |
| 6,210,896 B1 | 4/2001 | Chan |
| 6,258,568 B1 | 7/2001 | Nyren |
| 6,263,286 B1 | 7/2001 | Gilmanshin et al. |
| 6,267,872 B1 | 7/2001 | Akeson et al. |
| 6,274,320 B1 | 8/2001 | Rothberg et al. |
| 6,294,136 B1 | 9/2001 | Schwartz |
| 6,303,288 B1 | 10/2001 | Furcht et al. |
| 6,304,318 B1 | 10/2001 | Matsumoto |
| 6,340,567 B1 | 1/2002 | Schwartz et al. |
| 6,355,420 B1 | 3/2002 | Chan |
| 6,362,002 B1 | 3/2002 | Denison et al. |
| 6,392,719 B2 | 5/2002 | Kim |
| 6,400,425 B1 | 6/2002 | Kim et al. |
| 6,403,311 B1 | 6/2002 | Chan |
| 6,413,792 B1 | 7/2002 | Sauer et al. |
| 6,428,959 B1 | 8/2002 | Deamer |
| 6,448,012 B1 | 9/2002 | Schwartz |
| 6,464,842 B1 | 10/2002 | Golovchenko et al. |
| 6,503,409 B1 | 1/2003 | Fleming |
| 6,509,158 B1 | 1/2003 | Schwartz |
| 6,537,755 B1 | 3/2003 | Drmanac |
| 6,537,765 B2 | 3/2003 | Stricker-Kongra et al. |
| 6,610,256 B2 | 8/2003 | Schwartz |
| 6,617,113 B2 | 9/2003 | Deamer |
| 6,627,067 B1 | 9/2003 | Branton et al. |
| 6,672,067 B2 | 1/2004 | Farmer et al. |
| 6,673,615 B2 | 1/2004 | Denison et al. |
| 6,685,841 B2 | 2/2004 | Lopez et al. |
| 6,689,563 B2 | 2/2004 | Preparata et al. |
| 6,696,022 B1 | 2/2004 | Chan et al. |
| 6,713,263 B2 | 3/2004 | Schwartz |
| 6,746,594 B2 | 6/2004 | Akeson et al. |
| 6,762,059 B2 | 7/2004 | Chan et al. |
| 6,772,070 B2 | 8/2004 | Gilmanshin et al. |
| 6,790,671 B1 | 9/2004 | Austin et al. |
| 6,818,395 B1 | 11/2004 | Quake et al. |
| 6,911,345 B2 | 6/2005 | Quake et al. |
| 6,919,002 B2 | 7/2005 | Chopra |
| 6,927,065 B2 | 8/2005 | Chan et al. |
| 6,936,433 B2 | 8/2005 | Akeson et al. |
| 7,001,792 B2 | 2/2006 | Sauer et al. |
| 7,005,264 B2 | 2/2006 | Su et al. |
| 7,034,143 B1 | 4/2006 | Preparata et al. |
| 7,071,324 B2 | 7/2006 | Preparata et al. |
| 7,170,050 B2 | 1/2007 | Turner et al. |
| 7,189,503 B2 | 3/2007 | Akeson et al. |
| 7,211,414 B2 | 5/2007 | Hardin et |
| 7,217,562 B2 | 5/2007 | Cao et al. |
| 7,238,485 B2 | 7/2007 | Akeson et al. |
| 7,248,771 B2 | 7/2007 | Schmidt et al. |
| 7,250,115 B2 | 7/2007 | Barth |
| 7,262,859 B2 | 8/2007 | Larson et al. |
| 7,279,337 B2 | 10/2007 | Zhu |
| 7,282,130 B2 | 10/2007 | Flory |
| 7,282,330 B2 | 10/2007 | Zhao et al. |
| 7,297,518 B2 | 11/2007 | Quake et al. |
| 7,302,146 B2 | 11/2007 | Turner et al. |
| 7,315,019 B2 | 1/2008 | Turner et al. |
| 7,329,492 B2 | 2/2008 | Hardin et al. |
| 7,351,538 B2 | 4/2008 | Fuchs et al. |
| 7,355,216 B2 | 4/2008 | Yang et al. |
| 7,371,520 B2 | 5/2008 | Zhao et al. |
| 7,402,422 B2 | 7/2008 | Fuchs et al. |
| 7,462,449 B2 | 12/2008 | Quake |
| 7,476,503 B2 | 1/2009 | Turner et al. |
| 7,476,504 B2 | 1/2009 | Turner |
| 7,501,245 B2 | 3/2009 | Quake et al. |
| 7,595,160 B2 | 9/2009 | White et al. |
| 7,678,562 B2 | 3/2010 | Ling |
| 2001/0004728 A1 | 6/2001 | Preparata et al. |
| 2002/0028458 A1 | 3/2002 | Lexow |
| 2002/0058279 A1 | 5/2002 | Fritsch et al. |
| 2002/0127855 A1 | 9/2002 | Sauer et al. |
| 2002/0137089 A1 | 9/2002 | Deamer |
| 2003/0003609 A1 | 1/2003 | Sauer et al. |
| 2003/0064095 A1 | 4/2003 | Martin et al. |
| 2003/0064382 A1 | 4/2003 | Preparata et al. |
| 2003/0080042 A1 | 5/2003 | Barth et al. |
| 2003/0104428 A1 | 6/2003 | Branton et al. |
| 2003/0143614 A1 | 7/2003 | Drmanac |
| 2003/0207326 A1 | 11/2003 | Su et al. |
| 2003/0211502 A1 | 11/2003 | Sauer et al. |
| 2003/0232346 A1 | 12/2003 | Su |
| 2004/0137734 A1 | 7/2004 | Chou et al. |
| 2004/0146430 A1 | 7/2004 | Dugas |
| 2004/0197843 A1 | 10/2004 | Chou et al. |
| 2005/0019784 A1 | 1/2005 | Su et al. |
| 2005/0127035 A1 | 6/2005 | Ling |
| 2006/0019247 A1 | 1/2006 | Su et al. |
| 2006/0063171 A1 | 3/2006 | Akeson et al. |
| 2006/0154399 A1 | 7/2006 | Sauer et al. |
| 2006/0269483 A1 | 11/2006 | Austin et al. |
| 2006/0287833 A1 | 12/2006 | Yakhini |
| 2007/0020772 A1 | 1/2007 | Cao et al. |
| 2007/0042366 A1 | 2/2007 | Ling |
| 2007/0080511 A1 | 4/2007 | Campbell |
| 2007/0084163 A1 | 4/2007 | Lai |
| 2007/0084702 A1 | 4/2007 | Lin et al. |
| 2007/0138132 A1 | 6/2007 | Barth |
| 2007/0190542 A1 | 8/2007 | Ling et al. |
| 2007/0218471 A1 | 9/2007 | Kim et al. |
| 2007/0231795 A1 | 10/2007 | Su |
| 2007/0238112 A1 * | 10/2007 | Sohn et al. ............ 435/6 |
| 2008/0041733 A1 | 2/2008 | Hibbs et al. |
| 2008/0085840 A1 | 4/2008 | Buzby |
| 2008/0096287 A1 | 4/2008 | Barth |
| 2008/0102504 A1 | 5/2008 | Akeson et al. |
| 2008/0119366 A1 | 5/2008 | Sauer et al. |
| 2008/0171316 A1 | 7/2008 | Golovchenko et al. |
| 2008/0187915 A1 | 8/2008 | Polonsky et al. |
| 2008/0234136 A1 | 9/2008 | Drmanac et al. |
| 2008/0242556 A1 | 10/2008 | Cao et al. |
| 2008/0254995 A1 | 10/2008 | Kim et al. |
| 2009/0005252 A1 | 1/2009 | Drmanac et al. |
| 2009/0011943 A1 | 1/2009 | Drmanac et al. |
| 2009/0035777 A1 | 2/2009 | Kokoris et al. |
| 2009/0099786 A1 | 4/2009 | Oliver et al. |
| 2009/0176652 A1 | 7/2009 | Dahl et al. |
| 2010/0078325 A1 | 4/2010 | Oliver |
| 2010/0243449 A1 | 9/2010 | Oliver |

FOREIGN PATENT DOCUMENTS

| | | |
|---|---|---|
| EP | 1486775 * | 12/2004 |
| EP | 1486775 A1 | 12/2004 |
| EP | 1685407 | 8/2006 |
| WO | WO-9004652 | 5/1990 |
| WO | WO-9617957 | 6/1996 |
| WO | WO-9835012 | 8/1998 |
| WO | WO-0009757 | 2/2000 |
| WO | WO-0022171 | 4/2000 |
| WO | WO-0118246 | 3/2001 |
| WO | WO-0137958 | 5/2001 |
| WO | WO-0142782 | 6/2001 |
| WO | WO-0207199 | 1/2002 |
| WO | WO-0250534 | 6/2002 |
| WO | WO-03000920 | 1/2003 |
| WO | WO-03010289 | 2/2003 |
| WO | WO-03079416 | 9/2003 |
| WO | WO-03106693 | 12/2003 |
| WO | WO-2004035211 | 4/2004 |
| WO | WO-2004085609 | 10/2004 |
| WO | WO-2005017025 | 2/2005 |
| WO | WO-2006020775 | 2/2006 |
| WO | WO-2006028508 | 3/2006 |
| WO | WO-2006052882 | 5/2006 |
| WO | WO-2007106509 | 9/2007 |
| WO | WO-2007111924 | 10/2007 |
| WO | WO-2007127327 | 11/2007 |

| WO | WO-2008021488 | 2/2008 |
| --- | --- | --- |
| WO | WO-2008039579 | 4/2008 |
| WO | WO-2008042018 | 4/2008 |
| WO | WO-2008046923 | 4/2008 |
| WO | WO-2008049021 | 4/2008 |
| WO | WO-2008069973 | 6/2008 |
| WO | WO-2008079169 | 7/2008 |
| WO | WO-2010111605 | 9/2010 |
| WO | WO-2010111605 A2 | 9/2010 |
| WO | WO-2010138136 | 12/2010 |
| WO | WO-2010138136 A1 | 12/2010 |
| WO | WO-2012047589 A2 | 4/2012 |

OTHER PUBLICATIONS

Giehart B., et al., (2008) "Nanopore with transverse nanoelectrodes for electrical characterization and sequencing of DNA" Sensors and Actuators B., Elsevier Sequoia S.A, ScienceDirect,132:2.
Invitation to Pay Additional Fees and, Where Applicable, Protest Fee & Partial International Search dated Aug. 19, 2010, PCT/US2010/028848, 7 pages.
International Search Report and Written Opinion dated Sep. 30, 2010, PCT/US2010/028848, 14 pgs.
Bloom et al., Applications of Numbered Undirected Graphs, Proceedings of the IEEEE, vol. 65, No. 4, Apr. 1977, pp. 562-570.
Ghosh, et al, Direct detection of double-stranded DNA: molecular methods and applications for DNA diagnostics, Molecular BioSystems, 2006, 551-560, 10 pages.
International Preliminary Report on Patentability, Application No. PCT/US2009/055876, issuance date Mar. 8, 2011, 6 pages.
International Preliminary Report on Patentability, Application No. PCT/US2008/078432, issuance date Apr. 7, 2010, 6 pages.
International Preliminary Report on Patentability, Application No. PCT/US2010/028848, issuance date Sep. 27, 2011, 8 pages.
International Preliminary Report on Patentability, Application No. PCT/US2009/055878, issuance date Nov. 29, 2011, 9 pages.
Ben-Dor et al, "On the Complexity of Positional Sequencing by Hybridization", Journal of Computational Biology, vol. 8, No. 4, 2001, pp. 361-371.
Branton, Daniel et al, "The potential and challenges of anopore sequencing," Nature Biotechnology, vol. 26, No. 10, Oct. 2008, pp. 1146-1153.
International Search Report and Written Opinion, PCT/US2011/059933, dated Apr. 2, 2012, 13 Pages.
Akeson, et al., "Microsecond time-scale discrimination among polycytidylic acid, polyadenylic acid, and polyuridylic acid as homopolymers or as segments within single RNA molecules," Biophys. J. 77, 3227-3233 (1999).
Alberts, B., et al., (1970) "T4 Bacteriophage Gene 32: A Structural Protein in the Replication and Recombination of DNA," Nature 227:1313-1318.
Amit, B., et al., (1974) "Photosensitive Protecting Groups of Amino Sugars and Their Use in Glycoside Synthesis. 2-Nitrobenzyloxycarbonylamino and 6-Nitroveratryloxycarbonylamino Derivatives," J. Org. Chem. 39:192-196.
Arratia, R., et al., (1989) "Poisson Process Approximation for Repeats in One Sequence and Its Application to Sequencing by Hybridization," Dept. of Mathematics, University of Southern California.
Ashkin, "Optical trapping and manipulation of neutral particles using lasers," Proc. Natl. Acad. Sci. USA, vol. 94, Dd. 4853-4860, May 1997.
Austin, M., et al., (2004) "Fabrication of 5 nm Linewidth and 14 nm Pitch Features by Nanoimprint Lithography," App. Phys. Lett. 84:5299-5301.
Bains, W., et al., (1988) "A Novel Method for Nucleic Acid Sequence Determination," J. Theor. Biol. 135:303-307.
Baliga, R., et al., (2001) "Kinetic Consequences of Covalent Linkage of DNA Binding Polyamides," Biochemistry 40:3-8.
Bennett et al. Pharmacogenomics (2005) 6:373-382.
Bianco, P., et al., "Interaction of the RecA Protein of *Escherichia coli* with Single-Stranded Oligodeoxyribonucleotides," Nucleic Acids Research vol. 24. No. 24 (1996) 4933-4939.
Buchmueller, K.L., et al., (2005) "Extending the Language of DNA Molecular Recognition by Polyamides: Unexpected Influence of Imidazole and Pyrrole Arrangement on Binding Affinity and Specificity," J. Am. Chem. Soc. 127:742-750.
Buchmueller, K.L., et. al., (2006) "Physical and Structural Basis for the Strong Interactions of the -ImPy- Central Pairing Motif in the Polyamide f-ImPyIm," Biochemistry 45:13551-13565.
Cao, H., et al., (2002) "Fabrication of 10 nm Enclosed Nanofluidic Channels," Applied Physics Letters 81(1): 174-176.
Cao, H., et al., (2002) "Gradient Nanostructures for Interfacing Microfluidics and Nanofluidics," Applied Physics Letters 81:3058-3060.
Chen, C., et al., (1994) "Analogous Organic Synthesis of Small-Compound Libraries: Validation of Combinatorial Chemistry in Small-Molecule Synthesis," J. Am. Chem. Soc. 116:2661-2662.
Chen, P., et al., (2004) "Probing Single DNA Molecule Transport Using Fabricated Nanopores," Nano Letters 4:2293-2298.
Chetverin, A., et al., (1994) "Oligonucleotide Arrays: New Concepts and Possibilities," Bio/Technology 12:1093-1099.
Cox, M. (2007) "Motoring Along with the Bacterial RecA Protein," Nature Reviews—Molecular Cell Biology 9:127-138.
Dervan, P.B. (2001) "Molecular Recognition of DNA by Small Molecules," Bioorg. Med. Chem. 9:2215-2235.
Dervan, P.B., et al., (2003) "Recognition of the DNA minor groove by pyrrole-imidazole polyamides," Curr. Op. Struc. Biol. 13:284-299.
Doss, R.M., et al., (2006) "Programmable Oligomers for Minor Groove DNA Recognition," J. Am. Chem. Soc. 128:9074-9079.
Drmanac, R., et al. (1989) "Sequencing of Megabase Plus DNA by Hybridization: Theory of the Method," Genomics 4:114-128.
Ellervik, U., et al., (2000) "Hybroxybenzamide/Pyrrole Pair Distinguishes T-A from A-T Base Pairs in the Minor Groove of DNA," J. Am. Chem. Soc. 122:9354-9360.
Farkas, Z., et al., (2003) "DNA Uptake Into Nuclei: Numerical and Analytical Results," J. Phys.: Condens. Matter 15:S1767-S1777.
Fechter, E.J., et al., (2005) "Sequence-specific Fluorescence Detection of DNA by Polyamide-Thiazole Orange Conjugates," J. Am. Chem. Soc. 127:16685-16691.
Floreancig, P.E., et al., (2000) "Recognition of the Minor Groove of DNA by Hairpin Polyamides Containing α-Substituted-, β-Amino Acids," J. Am. Chem. Soc. 122:6342-6350.
Fodor, S., et al., (2005) "Light-Directed, Spatially Addressable Parall Chemical Synthesis" Research Article 6 pgs.
Fologea, D., et al., (2005) "Slowing DNA Translocation in a Solid-State Nanopore," Nano Lett. 5(9):1734-7.
Frieze, A., et al., (1999) "Optimal Reconstruction of a Sequence From its Probes," 12 pgs.
Gerland, U., et al., (2004) "Translocation of Structured Polynucleotides Through Nanopores," Phys. Biol. 1:19-26.
Gershow, M., et al., (2007) "Recapturing and Trapping Single Molecules with a Solid-State Nanopore," Nature Nanotech. 2:775-779.
Gracheva, M., et al., (2002) "Simulation of the Electric Response of DNA Translocation through a Semiconductor Nanopore-Capacitor," Nanotechnology 17:622-633.
Guo, L. (2004) "Recent Progress in Nanoimprint Technology and its Application," J. Phys. D: Appl. Phys 37:R123-R141 (Appendices B-D).
Gygi, M.P., et al., (2002) "Use of fluorescent sequence-specific polyamides to discriminate human chromosomes by microscopy and flow cytometry," Nucleic Acids Research 30:2790-2799.
Halby, L., et al., (2005) "Functionalized head-to-head hairpin polyamides: Synthesis, double-stranded DNA-binding activity and affinity," Bioorg. Med. Chem. Lett. 15:3720-3724.
Heller, C., (2001) "Principles of DNA Separation with Capillary Electrophoresis," Electrophoresis 22:629-643.
Heng, J., et al., (2004) "Sizing DNA Using a Nanometer-Diameter Pore," Biophysical Journal 87:2905-2911.
Hudson, B., (1999) "An Experimental Study of SBH with Gapped Probes," 50 pgs.
International Search Report for PCT/US04/04138, mailed May 4, 2006, 5 pages.
International Search Report and Written Opinion dated May 2, 2009, PCTUS2008/078432.
International Search Report and Written Opinion for PCT/US09/558876 dated Feb. 10, 2010.
International Search Report and Written Opinion dated Mar. 24, 2010 for PCT/US09/055878, 13 pages.
International Search Report and Written Opinion for PCT/US09/558876 dated Jun. 29, 2010, 10 pages.

Jonsson, U., et al., (1991) "Real-Time Biospecific Interaction Analysis Using Surface Plasmon Resonance and a Sensor Chip Technology," BioTechniques, 11:620-627.

Ju et al., Proc. Nat. Acad. Sci. USA (2006) 103:19635-19640.

Kalaugher, L., (2002) "Diffraction Gradient Lithography Aids Nanofluidics," Nanotechweb.org.

Kanehisa, L. (1984) "Use of Statistical Criteria for Screening Potential Homologies in Nucleic Acid Sequences," Nucleic Acids Research 12:203-213.

Kasianowicz et al., "Characterization of Individual Polynucleotide Molecules Using a Membrane Channel," Proc. Nat. Acad. Sci. USA 93:13770-13773 (1996).

Khrapko, K.R. et al., (1989) "An Oligonucleotide Hybridizatioin Approach to DNA Sequencing," FEBS Lett. 256:118-22.

Kim, C., et al., (1992) "Binding Properties of Replication Protein A from Human and Yeast Cells," Mol. and Cell. Bio. 12(7):3050-3059.

Kuo, et al., "Hybrid three-dimensional nanofluidic/microfluidic devices using molecular gates," Sensors and Actuators A, vol. 102 (Oct. 2002):223-233.

Langa, "Self-organized growth of single crystals of nanopores," Applied Physics Letters, AIP, American Institute of Physics, 2003, vol. 82, No. 2, pp. 278-280.

Li et al., "Lon-beam sculpting at nanometre length scales", Nature 412,166-169 (2001).

Liang, X., et al., (2007) "Single Sub-20 nm wide Centimeter-Long NanoFluidic Channel Fabricated by Novel Nanoimprint Mold Fabrication and Divest Imprinting," Nano Letters 7:3774-3780.

Liang, X., et al., (2008) "Nanogap Detector Inside Nanofluidic Channel for Fast Real Time Label-Free DNA Analysis," Nano Letters 8:1472-76.

Ling, X., et al., "Hybridization Assisted Nanopore Sequencing," Patent Specification, 32 pgs.

Loakes, D., et al., (1994) "5-Nitroindole as an Universal Base Analogue," Nucleic Acids Research 22:4039-4043.

Loakes, D., et al., (1995) "3-Nitropyrrole and 5-Nitroindole as Universal Bases in Primers for DNA Sequencing and PCR," 23:2361-2366.

Lohman, T., et al., (1994) "*Escherichia coli* Single-Stranded DNA-Binding Protein: Multiple DNA-Binding Modes and Cooperatives," Annu. Rev. Biochem. 63:527-70.

Losi, et al., "Time-Resolved Absorption and Photothermal Measurements with Recombinant Sensory Rhodopsin II from *Natronobacterium pharaonis*," Biophys. J. 77, 3277-3286, Dec. 1999.

Lysov, Y.P., et al., (1988) "Determination of the Nucleotide Sequence of DNA Using Hybridization with Oligonucleotides. A New Method," Dokl. Acad. Nauk SSSR 303:1508-1511 [Article in Russian].

Margulies et al., (2005) Nature 437:376-380.

Marques, M.A., et al., (2004) "Expanding the Repertoire of Heterocycle Ring Pairs for Programmable Minor Groove DNA Recognition," J. Am. Chem. Soc. 126:10339-10349.

McEntee, K., et al. "Binding of the RecA Protein of *Escherichia coli* to Single- and Double-Stranded DNA." J. Biol. Chem. (1981) 256:8835.

Meller, A., et al., (2000) "Rapid Nanopore Discrimination Between Single Polynucleotide Molecules," PNAS 97:1079-1084.

Meller, et al., "Voltage-driven DNA translocations through a nanopore," Phys. Rev. Lett. 86(15),3435-3438 (2001).

Nice, E., et al., (1993) "Mapping of the Antibody- and Receptor-Binding Domains of Granulocyte Colony-Stimulating Factor Using an Optical Biosensor," Journal of Chromatography 646:159-168.

Nichols, R., et al., (1994) "A Universal Nucleoside for Use at Ambiguous Sites in DNA Primers," Letters to Nature 369:492-493.

Novopashina, D.S., et al., (2005) "Sequence-Specific Conjugates of Oligo(2'-O-methylribonucleotides) and Hairpin Oligocarboxamide Minor-Groove Binders: Design, Synthesis, and Binding Studies with Double-Stranded DNA," Chemistry & Biodiversity 2:936-952.

Optical Tweezers: Introduction to Optical Tweezers, Retrieved Apr. 21, 2010 from http://www.nbi.dk/~tweezer/introduction.htm, pp. 1-5.

Pablo, P.J., et al., (2000) "Absence of dc-Conductivity." Phys. Rev. Lett. 85:4992-4995.

Partial International Search Report dated Feb. 15, 2010 for PCT/US09/055878, 3 pages.

Perry, J., et al., (2005) "Review of Fabrication of Nanochannels for Single Phase Liquid Flow," 3rd Intl. Conference on Microchannels and Minichannels, Paper No. ICMM2005-75104.

Pevzner, P. et al., (1991) "Improved Chips for Sequencing by Hybridization," Journal of Biomolecular Structure & Dynamics 9:399-410.

Pevzner, P., (1989) "1-Tuple DNA Sequencing: Computer Analysis," Journal of Biomolecular Structure & Dynamics 7:63-73.

Powell, M., et al., (1993) "Characetrization of the Pf3 Single-Strand DNA Binding Protein by Circular Dichroism Spectroscopy," Biochemistry 32:12538-12547.

Preparata, F., et al., (1999) "On the Power of Universal Bases in Sequencing by Hybridization," 7 pgs.

Preparata, F.P., et. al., (2000) "Sequencing-by-Hybridization at the Information-Theory Bound: An Optimal Algorithm," J. Comp. Biol. 7: 621-630.

Quake et al. Proc. Nat. Acad. Sci. USA (2003) 100:3960-3964.

Riehn, R. et al., (2005) Proc. Nat. Acad. Sci., 102:1012.

Robertson, J., et al., (2007) "Single-Molecule Mass Spectrometry in Solution Using a Solitary Nanopore," PNAS 104:8207-8211.

Rucker, V.C., et al., (2003) "Sequence Specific Fluorescence Detection of Double Strand DNA," J. Am. Chem. Soc. 125:1195-1202.

Sanger, F. et al., (1977) "DNA Sequencing with Chain-Terminating Inhibitors," Proc. Natl. Acad. Sci. USA 12:5463-5467.

Shinohara. Y., et al., (1995) "Use of a Biosensor Based on Surface Plasmon Resonance and Biotinyl Glycans for Analysis of Sugar Binding Specificities of Lectins," J. Biochem, 117:1076-1082.

Singer, E. (2008) "The $100 Genome," Technology Review 4 pgs.

Smeets, R., et al., (2008) "Translocation of RecA-Coated Double-Stranded DNA through Solid-State Nanopores," Nano Letters pp. A-G.

Southern, E.M. (1996) "DNA Chips: Analysing Sequence by Hybridization to Oligonucleotide on a Large Scale," Trends in Genetics 12(3):110-115.

Storm, et al., "Fabrication of solid-state nanopores with single-nanometre precision," Nature Materials 2,537-540, Auaust 2003.

Storm, A., et al., (2005) "Fast DNA Translocation through a Solid-State Nanopore," Nano Letters 5(7):1193-1197.

Strezoska, Z., et al., (1991) "DNA Sequencing by Hybridization: 100 Bases Read by a Non-Gel-Based Method," Proc. Natl. Acad. Sci. USA 88:10089-10093.

Tegenfeldt, J., et al., (2004) "The Dynamics of Genomic-Length DNA Molecules in 100 nm Channels," Proc. Nat. Acad. Sci. USA 101:10979-10983.

Tersoff, "Less is more," Nature 412, 135-136, Jul. 2001.

Terwilliger, T., et al., (1996) "Gene V Protein Dimerization and Cooperativity of Binding to Poly (dA)," Biochemistry 35:16652-16664.

Tucker, P., et al., (1994) "Crystal Structure of the Adenovirus DNA Binding Protein a Hook-On Model for Cooperative DNA Binding," The EMBO Journal 13(13):2994-3002.

Urbach, A.R., (2001) "Toward rules for 1:1 polyamide:DNA recognition," PNAS 98:4343-4348.

Warren, C.L., et al., (2006) "Defining the Sequence-Recognition Profile of DNA-Binding Molecules," PNAS 103:867-872.

Warren, S., (1996) "The Expanding World of Trinucleotide Repeats," Science 271:1374-1375.

Web article (2003) "DNA Combed Into Nanochannels," http://www.nature.com.

Written Opinion dated Jul. 1, 2008, PCT/US06/38748.

Zhang, W., et al., (2006) "Discrimination of Hairpin Polyamides with an α-Substituted-γ-aminobutyric Acid as a 5'-TG-3' Reader in DNA Minor Groove," J. Am. Chem. Soc. 128:8766-8776.

Zwolak, M., et al., (2008) "Physical Approaches to DNA Sequencing and Detection." Rev. Mod. Phy. 80:141-165 (J).

* cited by examiner

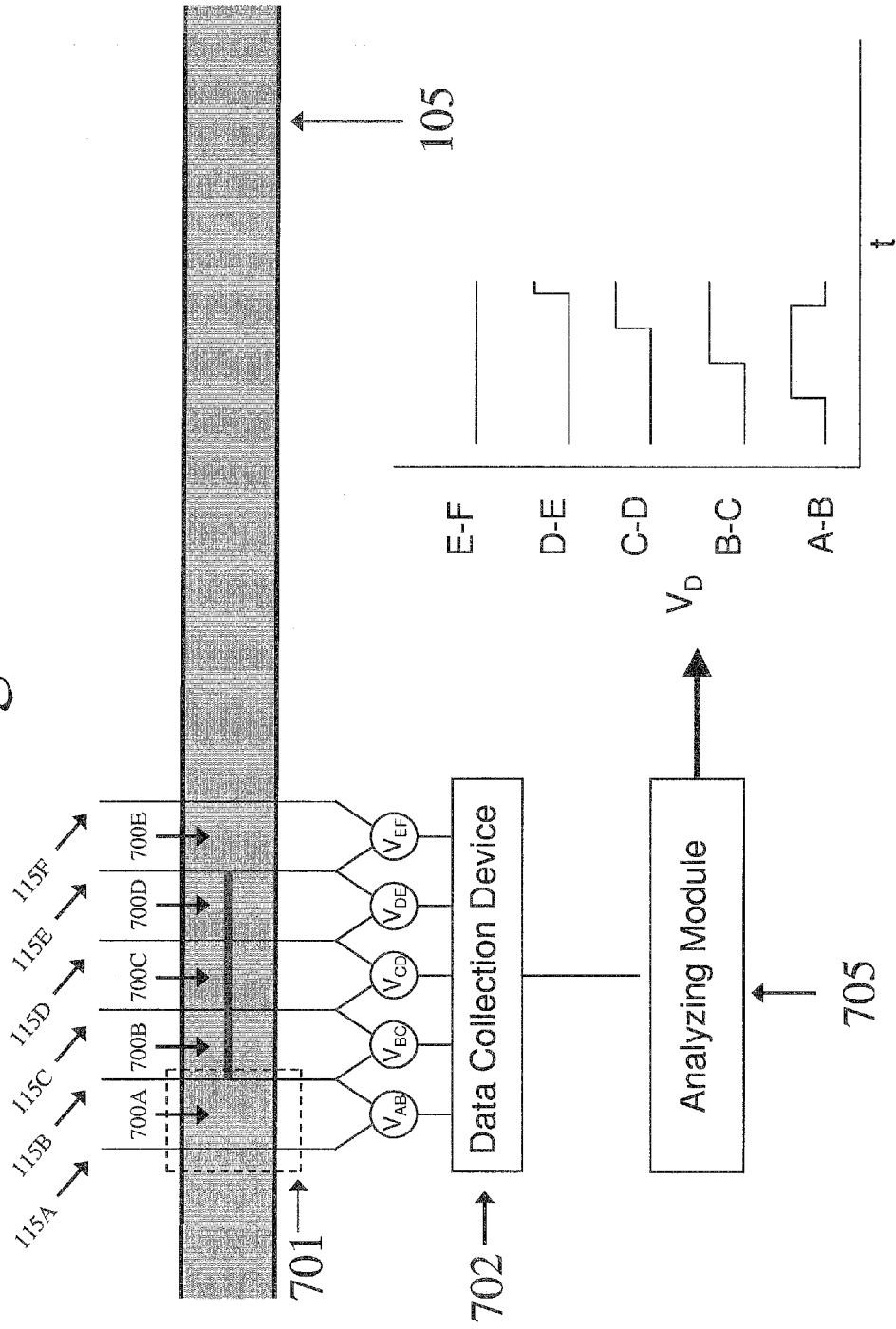

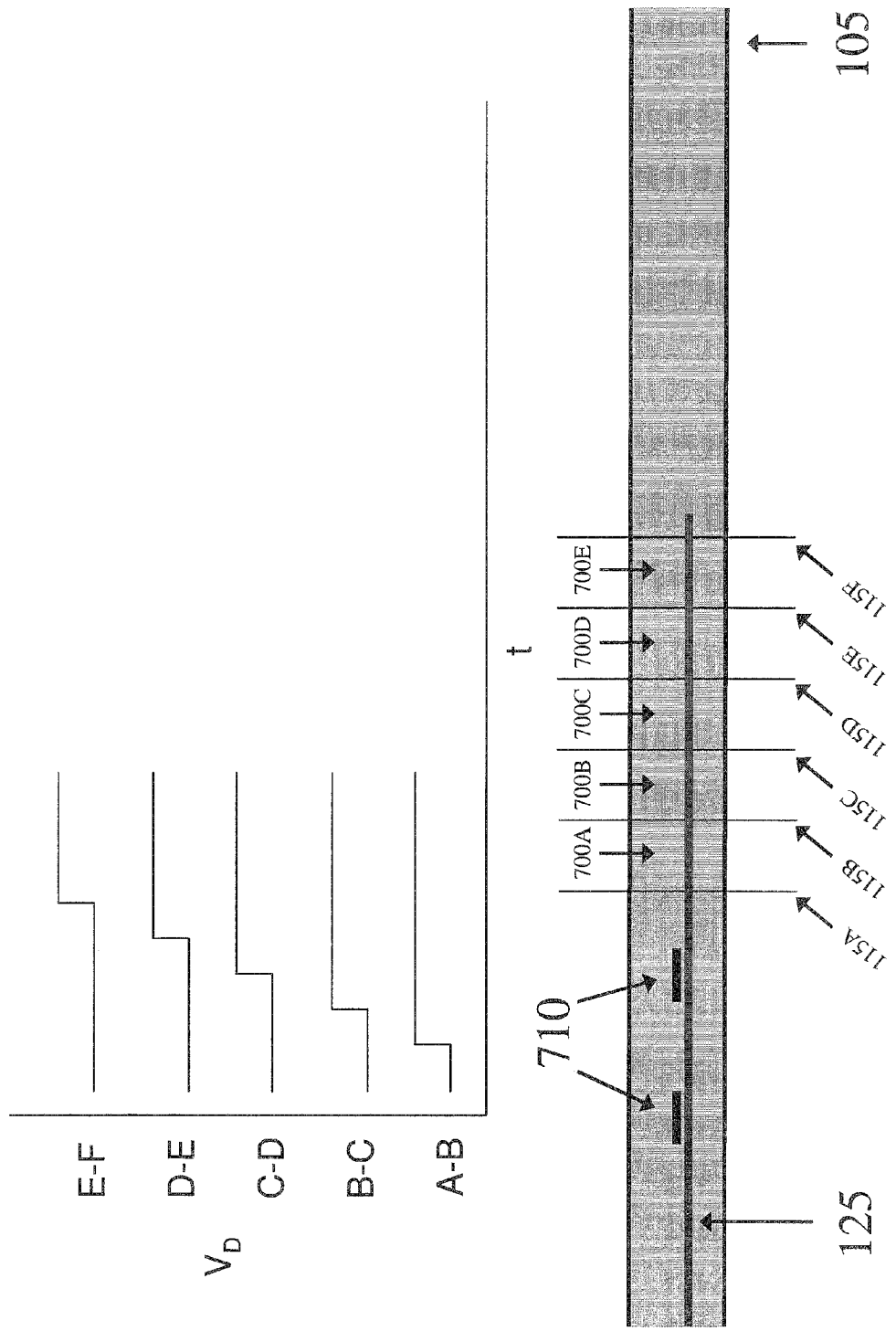

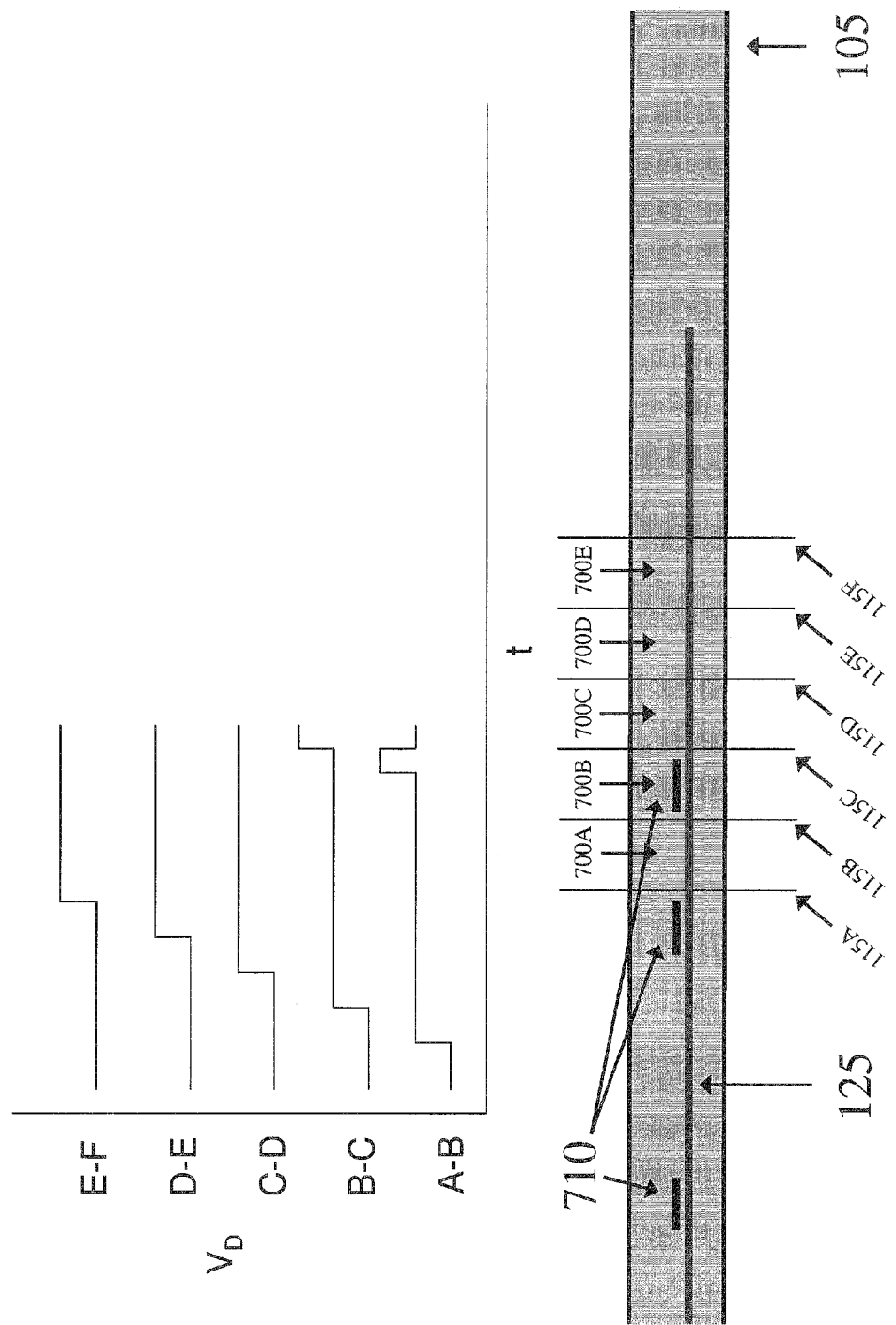

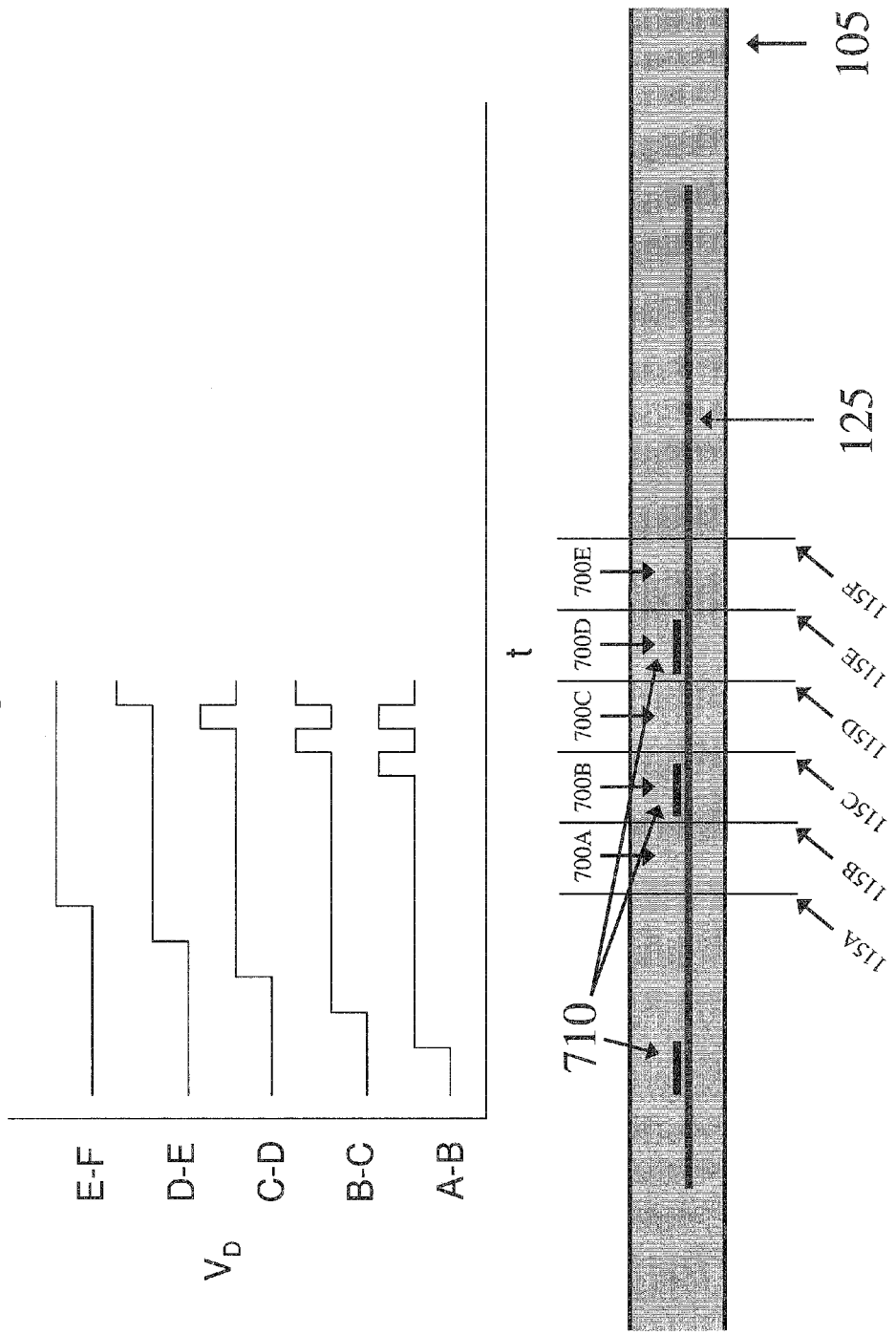

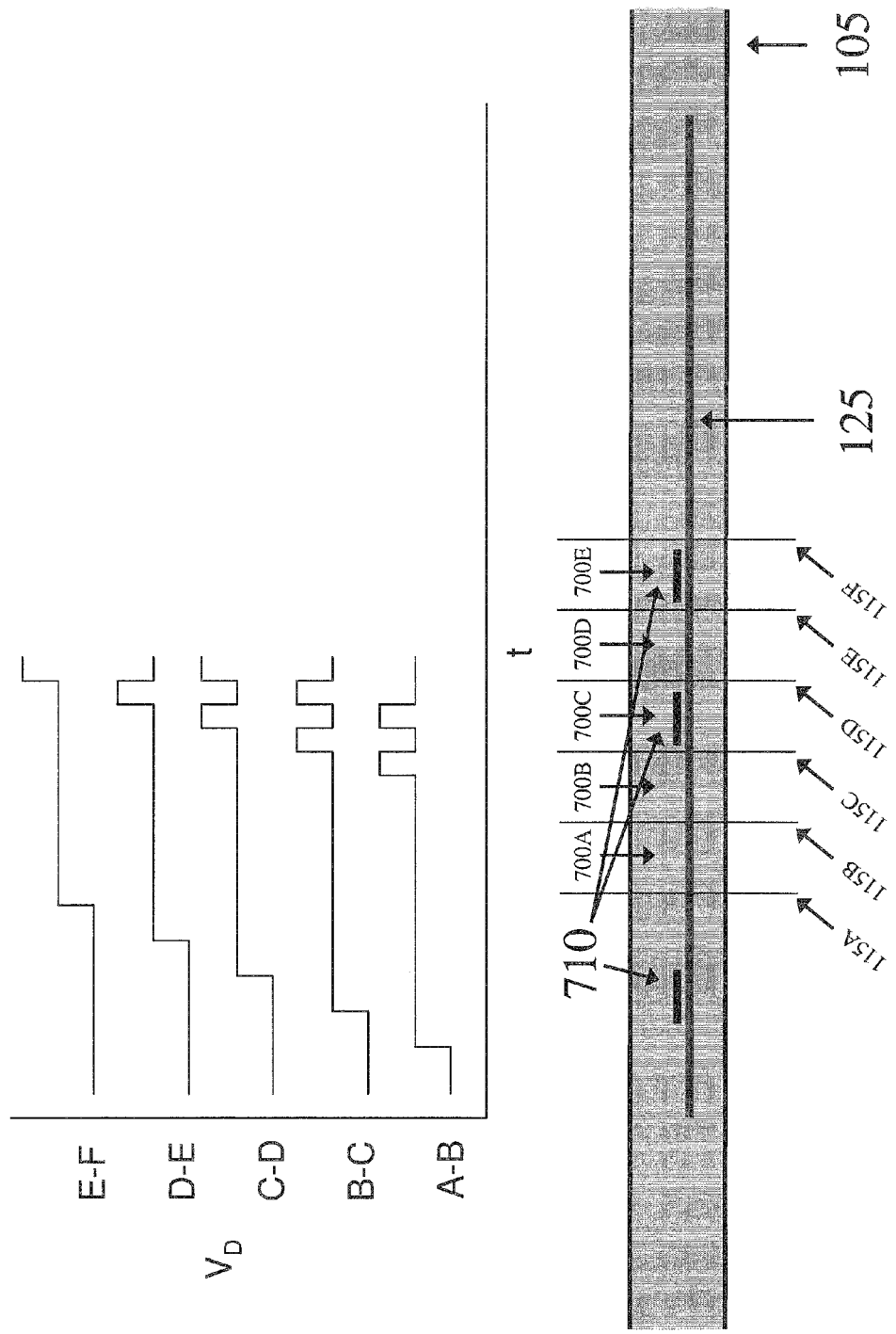

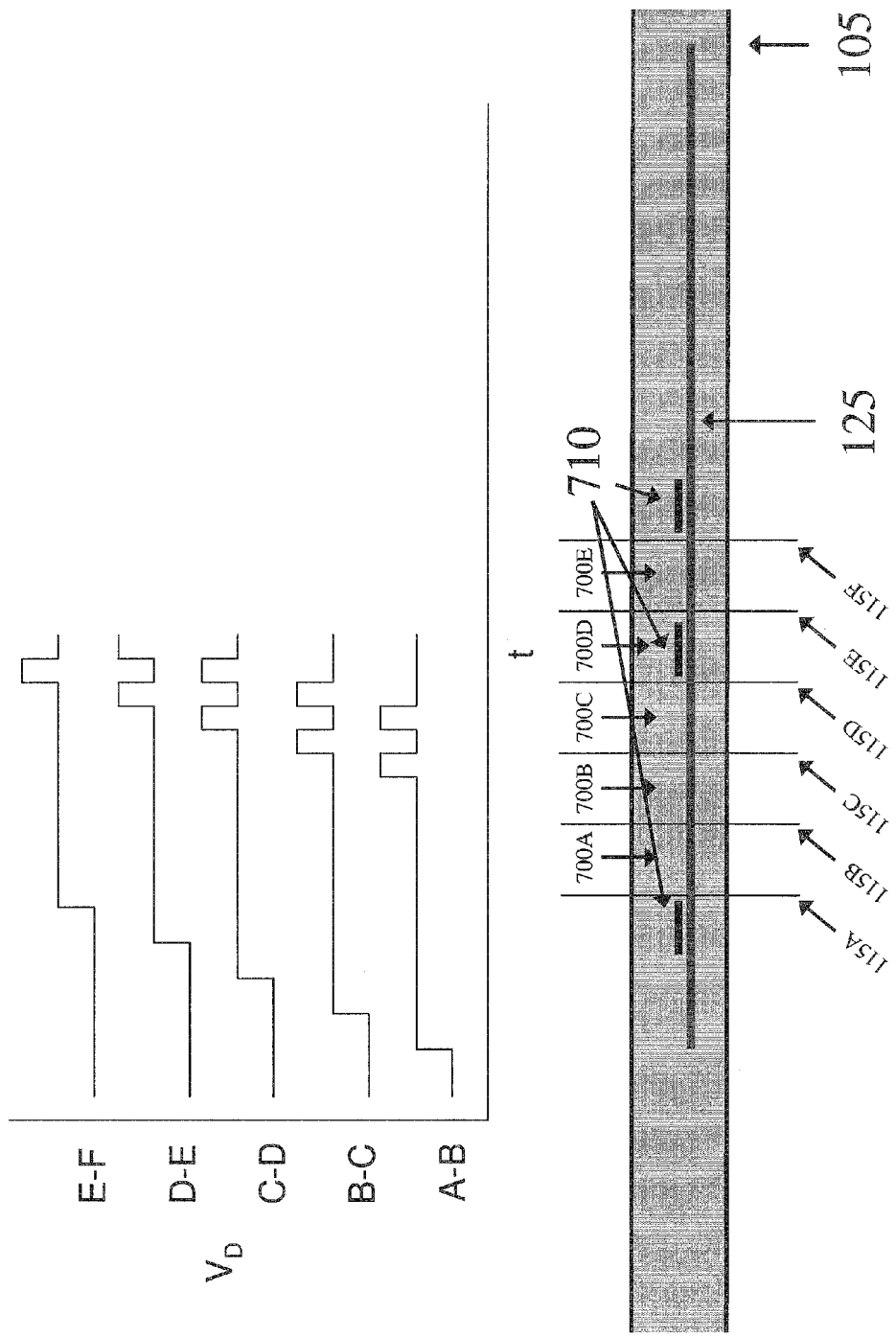

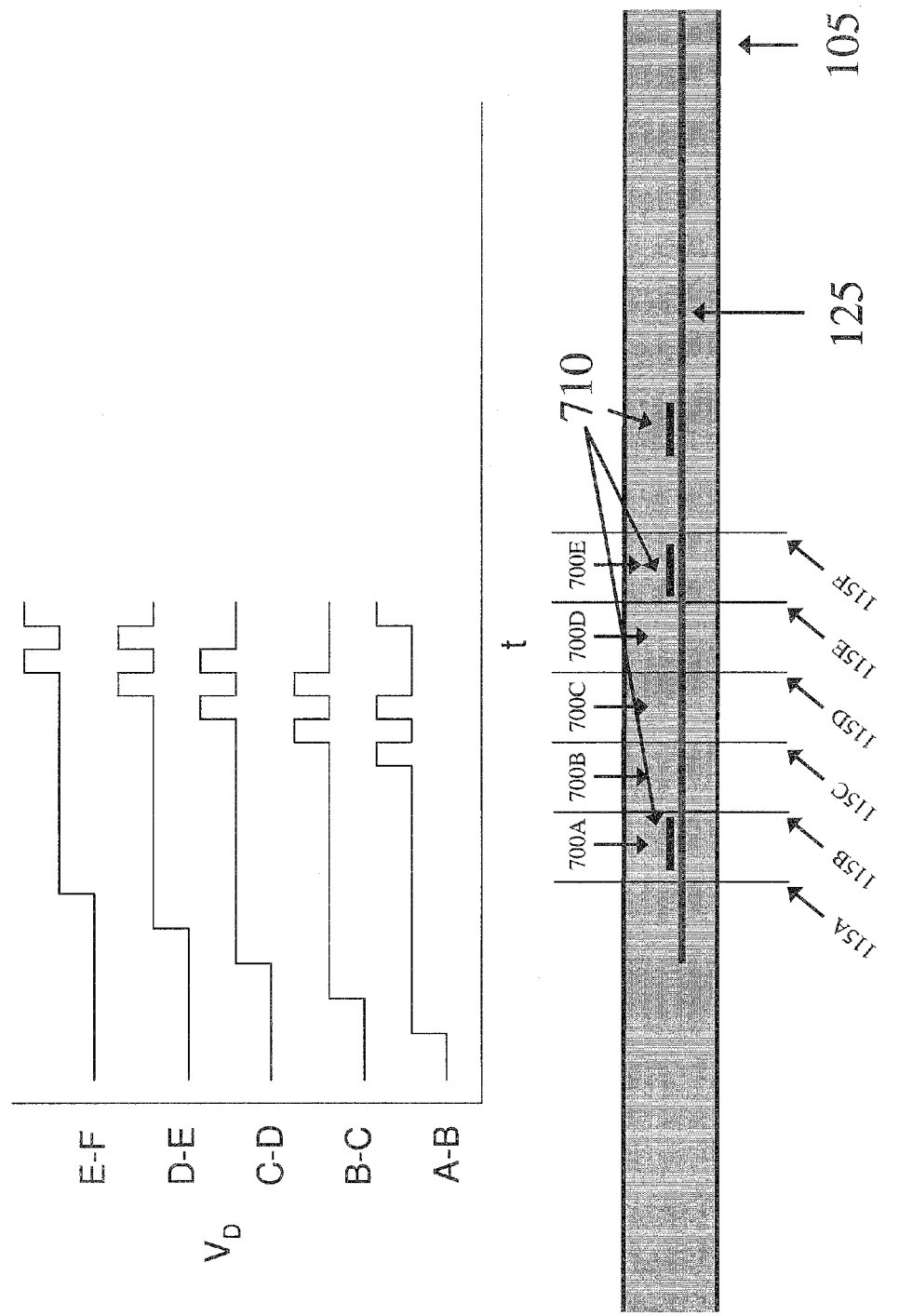

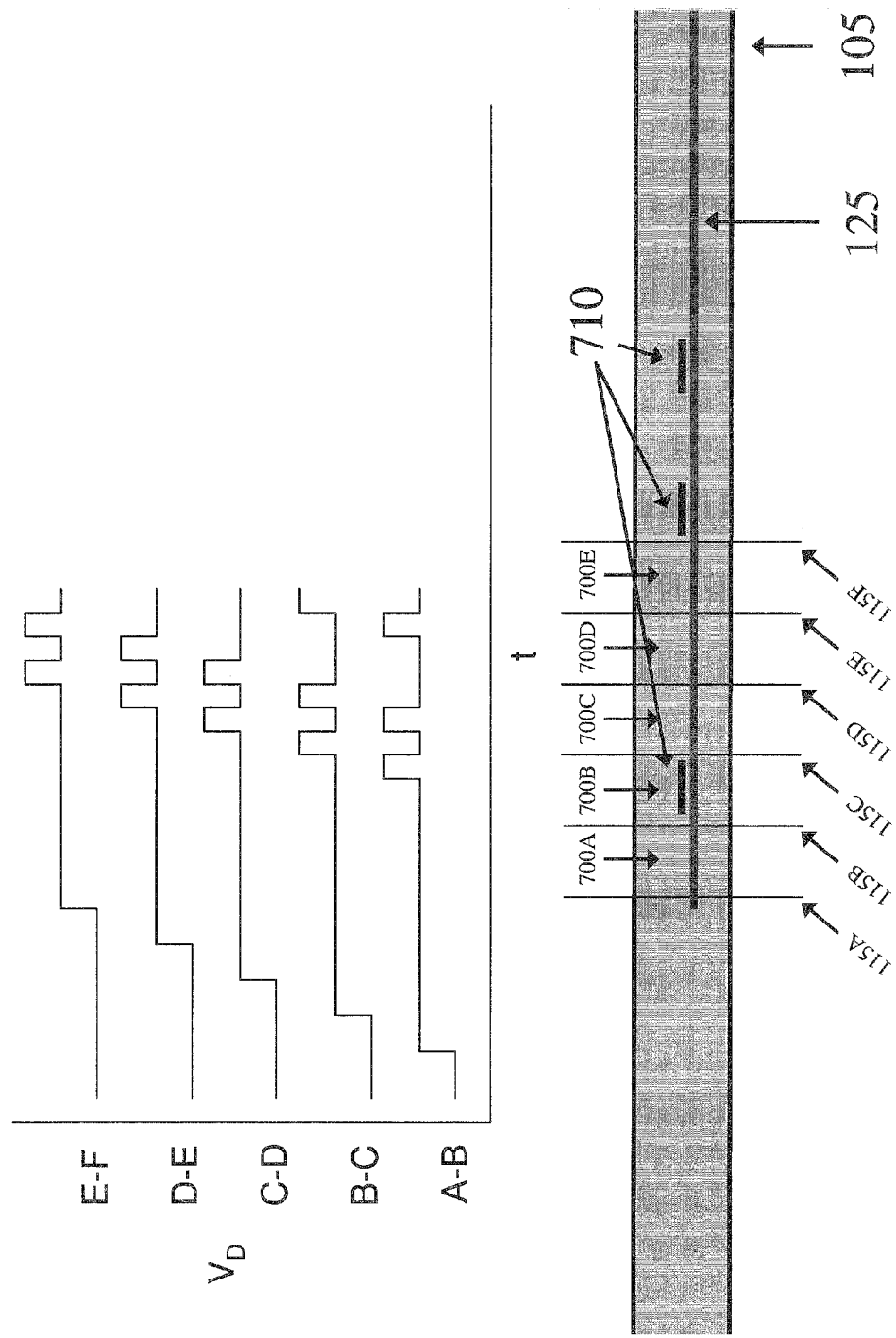

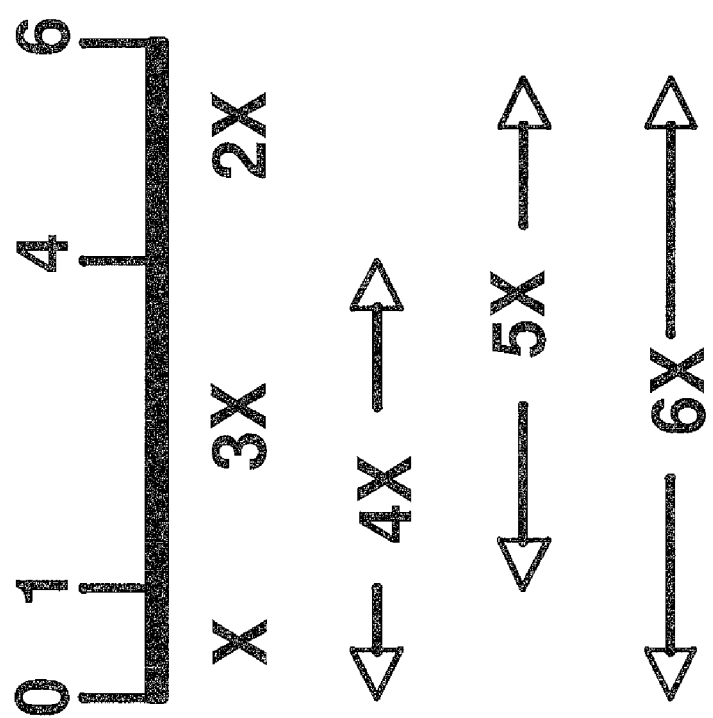

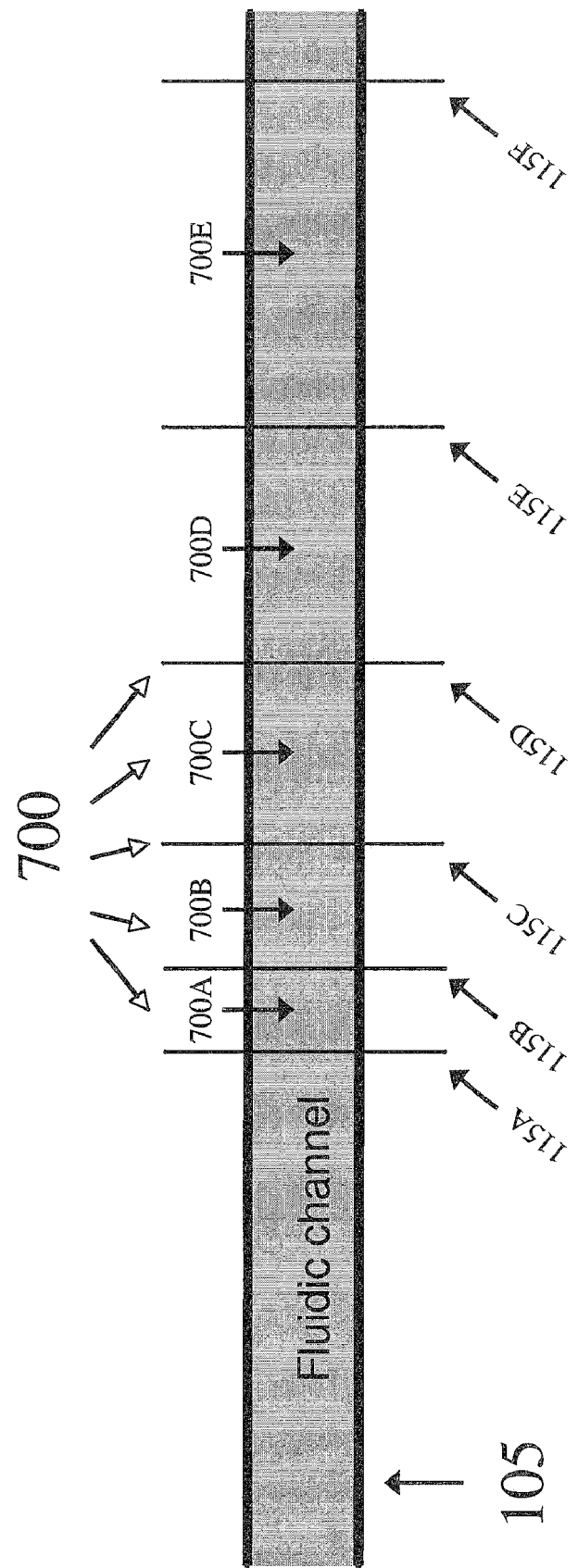

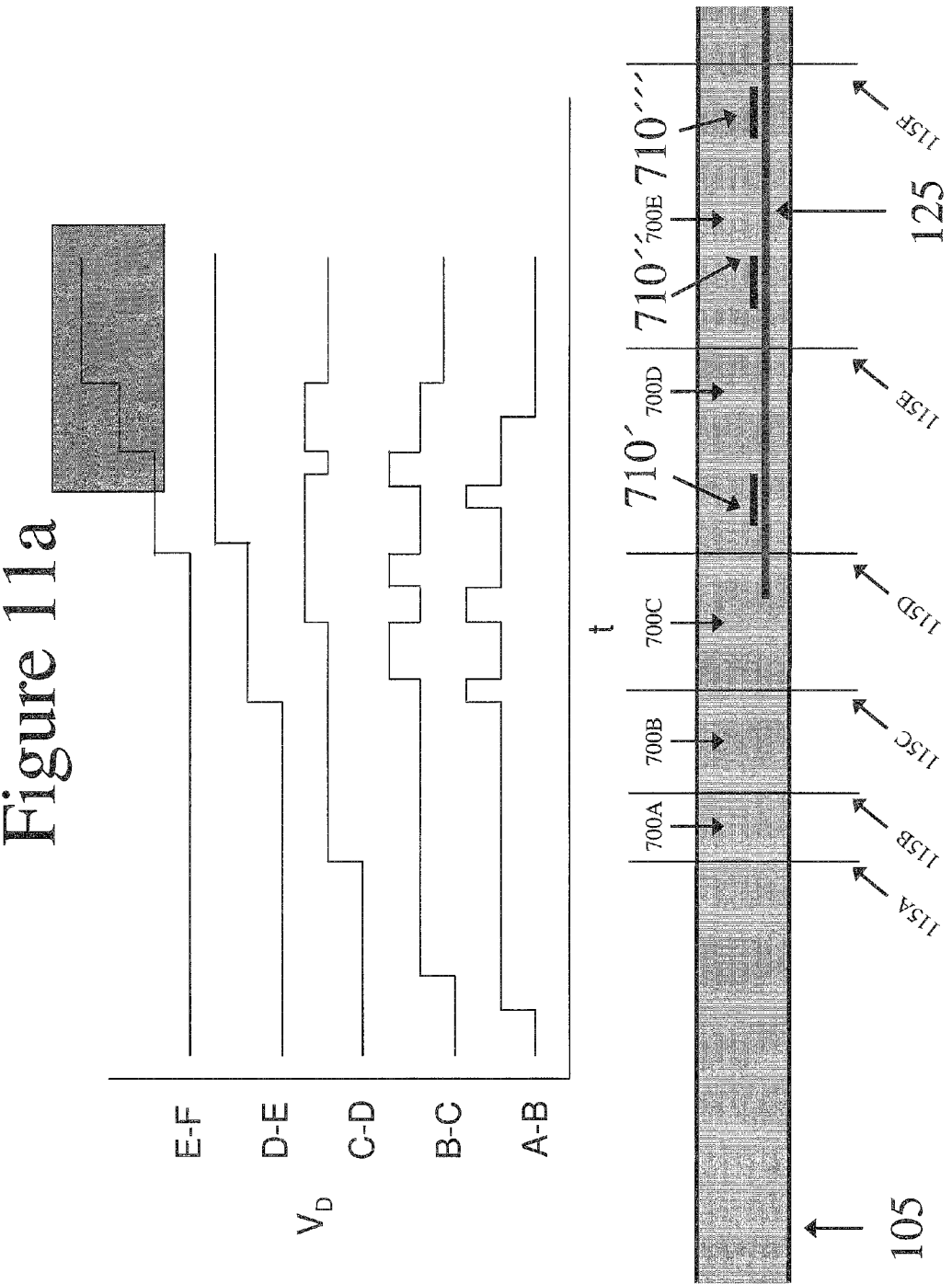

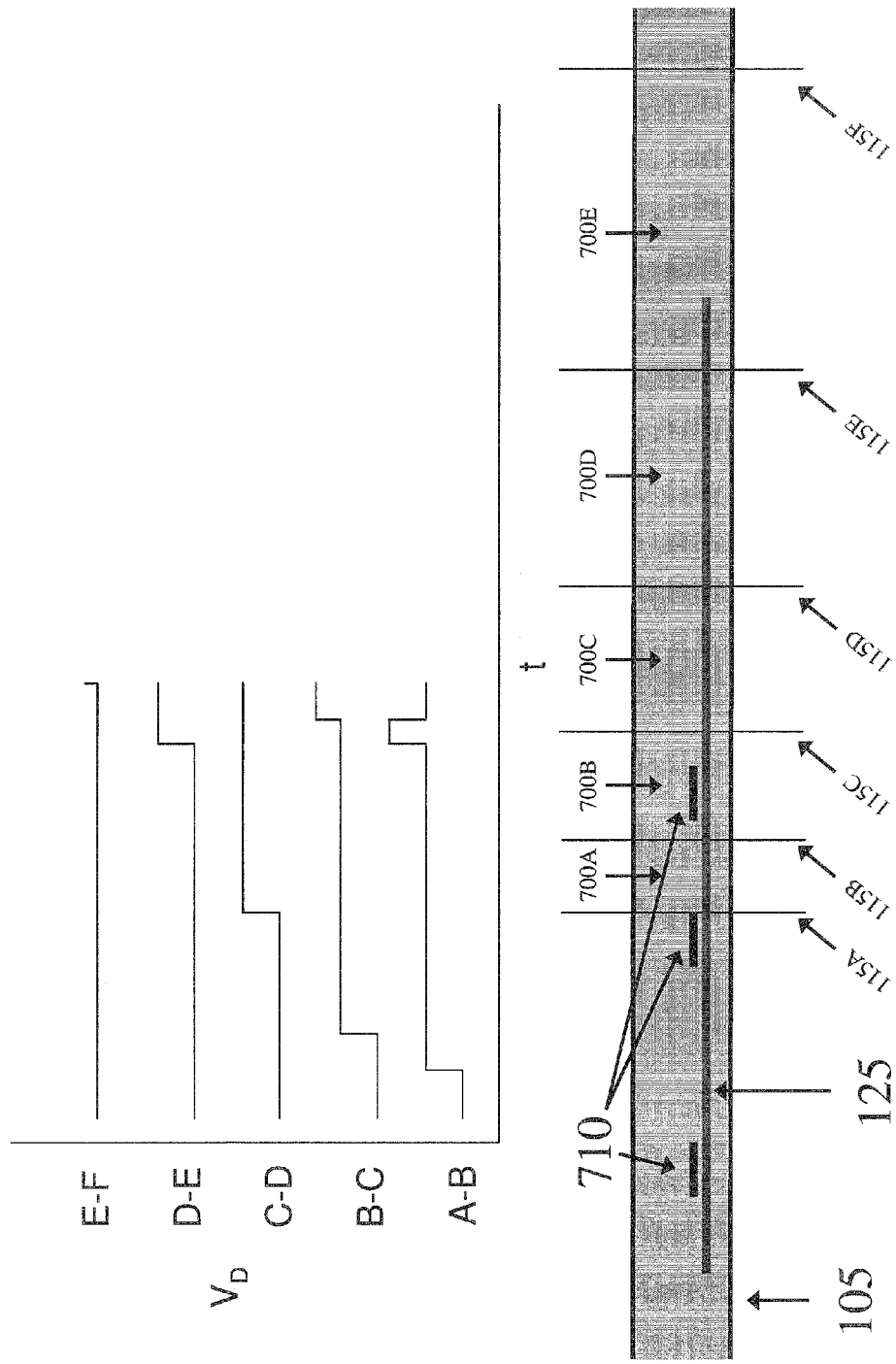

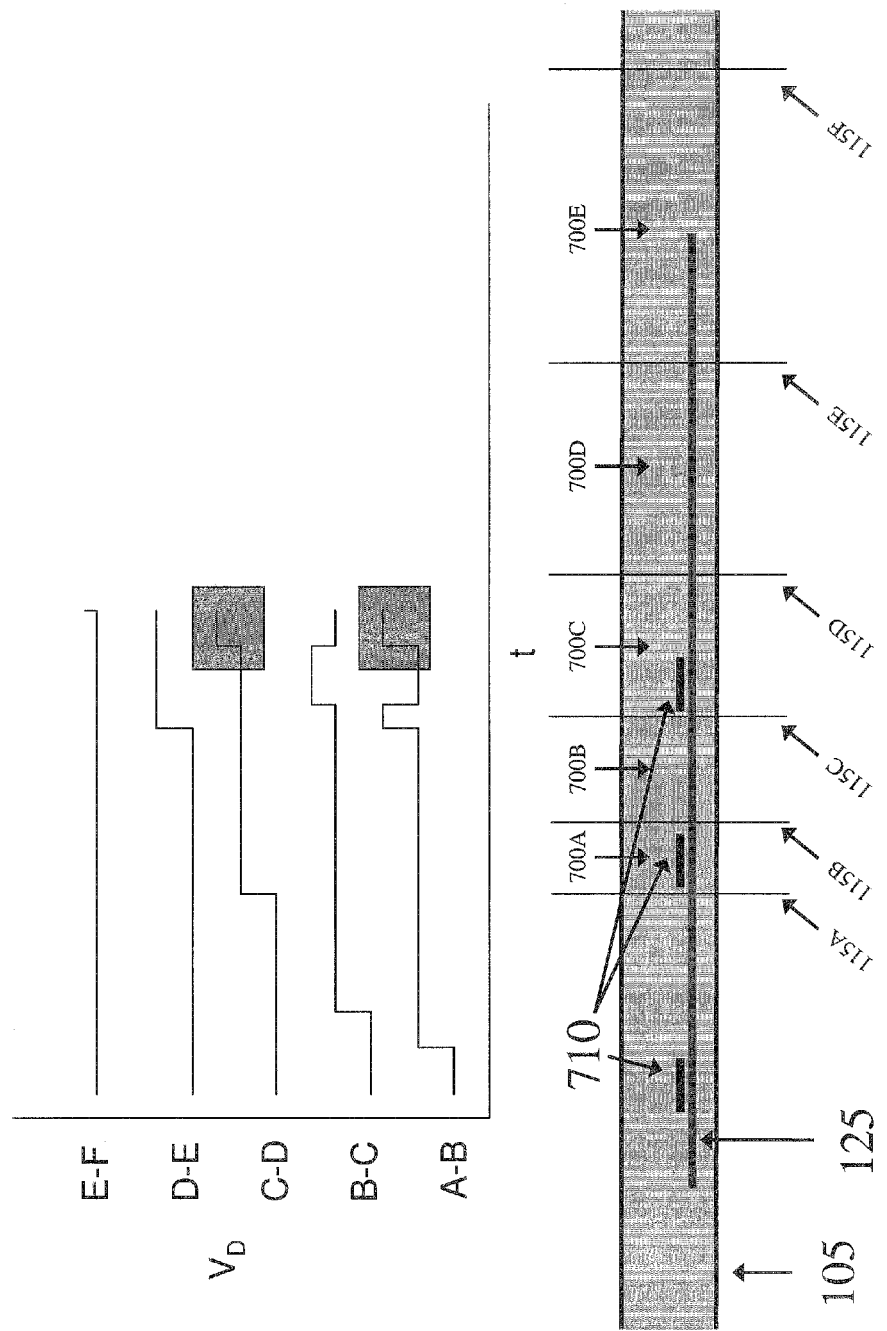

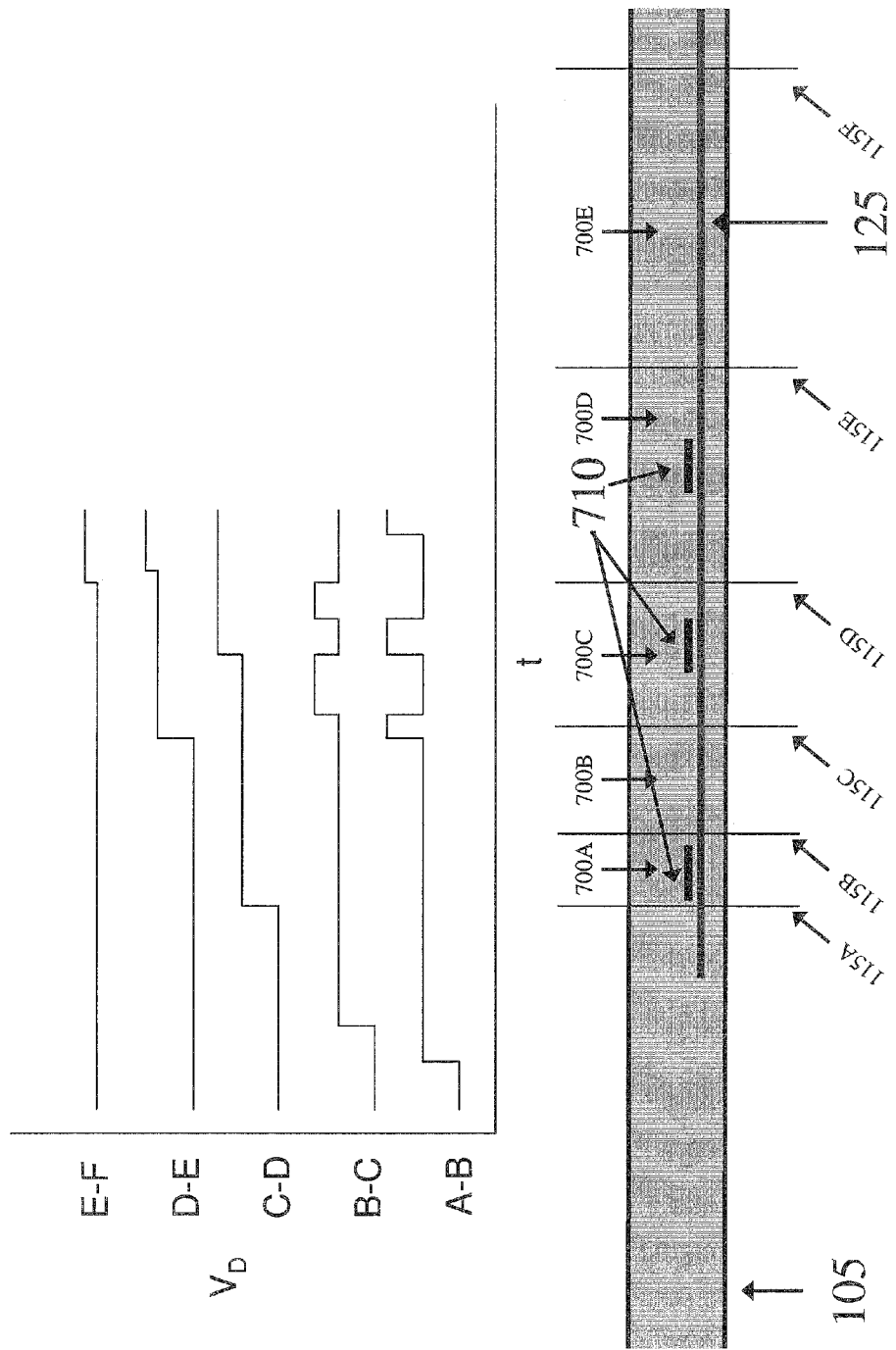

DEVICES AND METHODS FOR ANALYZING BIOMOLECULES AND PROBES BOUND THERETO

RELATED APPLICATIONS

This application claims the benefit of priority under 35 U.S.C. §119(e) to U.S. Provisional Ser. No. 61/318,048 filed Mar. 26, 2010 and U.S. Provisional Ser. No. 61/181,907 filed May 28, 2009. The entirety of each of these two applications is incorporated herein by reference.

SEQUENCE LISTING

The instant application contains a Sequence Listing which has been submitted via EFS-Web and is hereby incorporated by reference in its entirety. Said ASCII copy, created on Jul. 15, 2010, is named NAB007.txt and is 1,066 bytes in size.

FIELD OF INVENTION

The present invention relates generally to methods and devices for analyzing biomolecules. Mapping and sequencing of such biomolecules is contemplated herein.

BACKGROUND

A number of different approaches for sequencing nucleic acids exist. The traditional methods are the dideoxy-chain termination method described by Sanger et al., Proc Natl. Acad. Sci. USA, (1977) 74: 5463-67 and the chemical degradation method described by Maxam et al., Proc. Natl. Acad. Sci. USA, (1977) 74: 560-564. Of these two methods, the Sanger procedure has been the most widely used. The original Sanger method relied on radioactive labeling of the reaction products and separation of the reaction products by slab gel electrophoresis.

Both the Sanger and Maxam methods are time and labor intensive. The start of the Human Genome Project was the impetus for the development of improved, automated systems to perform Sanger sequencing. As a result, detection of fluorescence has replaced autoradiography and capillary electrophoresis has replaced the ultrathin slab gels originally used to separate reaction products. Automated sequencers have been developed and are capable of processing large numbers of samples without operator intervention.

The completion of the Human Genome Project has refocused the need for new technologies that are capable of rapidly and inexpensively determining the sequence of human and other genomes. There is has been much discussion in recent years about personalized medicine. The vision of personalized medicine involves every individual having his or her complete genome sequenced at high accuracy and using this information to guide clinical care, specifically for risk stratification of patients and pharmacogenomics.

In recent years, a number of technological advances have been developed enabling a great reduction in the cost of sequencing and substantially increasing the amount of sequence data produced. Most sequencing methods currently available utilize optical detection for the determination of the DNA sequence. The most prevalent sequencing methods are referred to as sequencing by synthesis (SBS).

Typical embodiments of SBS consist of the stepwise synthesis of a strand of DNA that is complementary to a template sequence from the target genome to be sequenced. The SBS methods can be divided into those that are performed in batch mode and those that are performed in real-time. The batch mode processes rely on the stepwise synthesis of the new DNA strand with the limitation that the synthesis is only allowed to proceed for one nucleotide position, for one nucleotide type, or for the combination of one nucleotide position and one nucleotide type. The incorporation of the nucleotide occurs in parallel for large numbers of templates. Detection is achieved using a variety of methods.

Embodiments of the batch mode utilizing a single nucleotide type are used by Roche for pyrosequencing with the 454 platform. The Roche technology (see, e.g., Margulies et al. (2005) Nature, 437:376-380; U.S. Pat. Nos. 6,274,320; 6,258,568; 6,210,891) utilizes pyrosequencing. The method depends on several enzymes and cofactors to produce luminescence when a nucleotide is incorporated. A single nucleotide species is introduced into a large number of small reaction vessels each containing multiple copies of a single template. The incorporation of the nucleotide is accompanied by light emission. When the reaction has run to completion, the reagents are washed from the reaction volumes and a next nucleotide and its required reagents are washed into the reactions. Each template is thus extended in an iterative fashion, one nucleotide at a time. Multiple incorporations of the same nucleotide require the quantitative determination of the amount of light emitted. Homopolymer tracts in templates may be difficult to accurately sequence as the incremental amount of light emitted for each subsequent position in the homopolymer becomes small compared to the total amount emitted.

In a second embodiment of the SBS method, platforms by Helicos (see, e.g., Quake et al Proc. Nat. Acad. Sci. USA (2003) 100: 3960-3964; U.S. Pat. Nos. 6,818,395; 6,911,345; 7,297,518; 7,462,449 and 7,501,245), Illumina (see, e.g., Bennett et al. Pharmacogenomics (2005) 6:373-382), and Intelligent Bio-Systems (see, e.g., Ju et al. Proc. Nat. Acad. Sci. USA (2006) 103:19635-19640) allow only the incorporation of a single nucleotide at each step. Template strands are attached to a solid support and a primer sequence is annealed. A polymerase used to extend the primer to make a complement to the template. The nucleotides are derivatized such that after the incorporation of a single nucleotide, the growing strand is incapable of further extension. The nucleotides are further derivatized to make them fluorescent. In the Helicos technology, the four nucleotides are labeled with the same fluorescent tag. This requires that each nucleotide type be added separately. In contrast, the Illumina and Intelligent Bio-Systems technologies utilize four different fluorescent tags so that a mixture of all four derivatized nucleotides may be added at the same time. For both technologies, the incorporation of a nucleotide is accompanied by the appearance of fluorescence in the growing strand. In the case of Illumina, the wavelength of the fluorescence emission indicates the identity of the newly incorporated nucleotide. In the Helicos technology, only a single nucleotide type is added at each cycle. Thus, the appearance of fluorescence at a position on the solid support indicates the incorporation of the added nucleotide for that template. Templates that do not incorporate the nucleotide present in the reaction remain dark.

Following the observation of any incorporated fluorescence, the blocking groups and fluorescent tags are removed prior to the next cycle. Multiple cycles result in the acquisition of sequence data for many templates in a single run. The instrumentation typical for these technologies is said to allow for the automated acquisition of sequence information for hundreds of thousands to millions of templates in parallel.

SBS methods may also be performed in real-time. In this embodiment, polymerase is used to incorporate fluorescently labeled nucleotides and the fluorescence is observed during DNA strand synthesis. The four nucleotides are labeled with different fluorescent tags. The fluorescent tags are attached to the terminal phosphate of the nucleotide triphosphate. During incorporation of the nucleotide into the growing strand the fluorophore is released to solution and the growing strand remains non-fluorescent. The identity of the incorporated strand is determined while the nucleotide resides in the active site of the enzyme and before the cleaved diphosphate is released to bulk solution.

The fluorescence of the incorporated nucleotide typically is measured in a background fluorescence from a much larger concentration of unincorporated nucleotide. Pacific Biosystems (see, e.g., U.S. Pat. Nos. 7,170,050; 7,302,146; 7,315,019; 7,476,503; and 7,476,504) identifies the incorporated nucleotide based on the residence time in the polymerase active site. Fluorescence emission from the active site for an appropriate time indicates incorporation and the emission wavelength determines the identity of the incorporated nucleotide. Polymerase is attached to the bottom of zero-mode waveguides. Zero-mode waveguides are reaction cells whose dimensions limit the fluorescence excitation to the evanescent wave from the light source. Thus, only fluorescent tags close to the bottom surface of the reaction volume are excited.

Visigen (now owned by Life Technologies) identifies the incorporated nucleotide through Fluorescent Resonant Energy Transfer (FRET) between an acceptor in the polymerase active site and a fluorescent tag on the nucleotide (see, e.g., U.S. Pat. Nos. 7,211,414 and 7,329,492). Only nucleotides held in the active site of the polymerase show fluorescence. Incorporation is identified by the residence time of the fluorescence in the active site and the nucleotide identity is determined by the emission wavelength.

Other recently developed methods to sequence DNA rely on hybridization and ligation. Both the SOLiD and Complete Genomics technologies rely on the combination of hybridization and ligation. The SOLiD system (Life Technologies) immobilizes short template strands via an adapter. A primer and a pool of labeled oligonucleotides containing two fixed positions and six degenerate positions is hybridized to the template. The primer hybridizes to the adaptor. The pool consists of 65,536 (4^8) different sequences. Four fluorescent dyes are used to label the oligonucleotides in a fashion that creates four subsets based on the sixteen combinations at the two fixed positions. Thus, each fluorescent tag is associated with four of the sixteen possible combinations. Following hybridization, a ligase is added and any probes in the pool that hybridized contiguously with the primer are ligated to the primer. The fluorescence of the hybridized and ligated product is determined. The fluorescence defines which subset of sequences hybridized to the template and ligated to the primer. The terminal three bases and the associated fluorescent tag are cleaved from the hybridized and ligated oligonucleotide. Subsequent rounds of hybridization, ligation, and cleavage are performed. In this first series of reactions, each cycle identifies a subset for the pair of nucleotides in the template that is 5 nucleotides downstream from subset of 4 pairs that were identified in the last cycle. After several cycles, the primer, and the oligonucleotides that have been ligated to it, is washed off the template The entire procedure is repeated starting with a primer that is one nucleotide shorter than the original primer, then with primers that are two, three, and four nucleotides shorter than the original primer. These subsequent rounds shift the frame of interrogation so that the bases that make-up the template strand can be identified from the union between the two subsets of reaction that overlapped at that position.

Complete Genomics technology utilizes a similar hybridization and ligation method (see, e.g., US Patent Application Publication Nos. 20080234136; 20090005252; 20090011943; and 20090176652). In the Complete Genomics technology, a primer is hybridized to an adaptor that is attached to the end of the template. A series of pools of oligonucleotides is constructed. In each pool, the nucleotide at a single position is identified by using four-color fluorescence. The remaining positions are degenerate. The first pool is hybridized to the template. Oligonucleotides that hybridize adjacent to the primer are subsequently ligated. After washing excess oligonucleotides away, the fluorescence of the ligated oligonucleotide identifies the nucleotide at the defined position in that pool. The ligated primer and oligonucleotide are washed off the template and the process is repeated with the next pool of oligonucleotides that probe the next position down from the primer.

The SBS and hybridization-ligation methods generate short pieces or reads of DNA sequence. While the short reads can be used to re-sequence human genomes, they are not favorable for the de novo assembly of human genomes. With the recent realization that human genomes contain large numbers of inversions, translocations, duplications, and indels (e.g., mutations that include both insertions, deletions, and the combination thereof), the quality of human genome data from short reads is even more suspect. Genetic rearrangements are even more prevalent in cancer.

While embodiments of the short read technologies that incorporate paired-end reads have been proposed and the length of the sequence data from these technologies has increased incrementally over the last two years, it is clear that longer read technologies are necessary for the accurate assembly of human genome data.

In addition to the undesirable nature of short reads, all of the DNA sequencing methods described above employ optical detection. The throughput of optical methods limits the ultimate performance characteristics of any of these sequencing technologies. Optical methods are capable of identifying single molecules. However, the time required to observe and accurately identify events is typically too slow to meet the need for higher throughput. While the current generation of sequencing technologies has lowered the cost of sequencing by orders of magnitude in comparison to the methods used to sequence the first human genomes, the methods remain too slow and costly for routine analysis of human genomes.

A need therefore exists for efficient methods and devices capable of rapid and accurate nucleic acid sequencing for de novo assembly of human genomes. It is desirable to have long read lengths and to use as little nucleic acid template as possible. Moreover, single-molecule optical detection of DNA has limitations with respect to sensitivity and speed.

Thus, there remains a need for improved methods and devices for the analysis of biomolecules, including methods and devices for mapping and sequencing such biomolecules.

SUMMARY

Embodiments of the present invention provide improved devices and methods for determining the length and sequences of analytes (e.g., biomolecules, such as biopolymers) by detecting electrical arising signals from an analyte as the analyte traverses a nanopore or fluidic channel. Embodiments of the invention als provide a method for determining the length of an analyte or distance between markers on an analyte without having to rely on an absolute correlation between time and position. In one embodiment, two or more electrical signals may be detected by disposing a plurality of sensing electrodes along a length of a fluidic channel. The detection of two or more electrical signals from separate sensing electrodes enables more accurate determination of analyte length and sequence. The distance between hybridization events on a target biomolecule can be more accurately determined by using coincident detection events. Accurate determination of distance between hybridizing probes enables highly accurate sequencing.

More particularly, certain embodiments of the present invention utilize multiple pairs of nanoscale electrodes for electronic sensing of target biomolecules, e.g., DNA, RNA, proteins, and polypeptides, in fluidic microchannels and nanochannels. In these embodiments, the sensing elements in the fluidic channel may be used to determine the length of the analyte or they may be used to determine the distance between probes hybridized to a target strand of biomolecule. The device design is similar to nanochannel devices used for optical detection. Two micro-scale liquid reservoirs may be fabricated at a distance of 100 to 200 µm. One or more fluidic channels may connect the two reservoirs. A cap may be fabricated by drilling holes that will allow fluid introduction to each reservoir and to provide access for macroscopic electrodes. Along the length of the fluidic channels, a series of sensing elements are fabricated. Each sensing element may be composed of two electrodes that bisect the fluidic channel. In use, a voltmeter may be used to monitor the potential difference for each pair of sensing electrodes.

The biomolecule to be analyzed may be introduced to one of the microfluidic reservoirs. Macroscopic electrodes may be connected to a power supply and used to apply a potential between the two reservoirs. Biomolecule fragments may be electrophoretically driven from the microscopic reservoir into the channels. Alternatively, the fragments may be driven by a chemical gradient, a pressure gradient, or combinations of these, with or without electrophoresis. As each biomolecule fragment moves down the fluidic channel, it may enter and exit each of the sensing elements disposed in the fluidic channel.

In the absence of a biomolecule fragment, the detector volumes contain only the ionic solution and typically have a baseline potential difference measured between the two electrodes that make up the sensing element. As biomolecule fragments enter the detector volume, the potential measured between the two sensing electrodes may change because the biomolecule has an ionic conductivity different from that of the ionic solution. When the biomolecule enters the detector volume, the conductivity of the channel between the two sensing electrodes will typically be reduced as the biomolecule is less conductive than the buffer solution (See de Pablo, P. J.; Moreno-Herrero, F; Colchero, J.; Gomez-Herrero, J.; Herrero, P.; Baro, A. M.; Ordejon, P.; Soler, J. M.; Artacho, E. Absence of dc-Conductivity in *Phys. Rev. Lett.* 2000, 85, 4992-4995, which is incorporated by reference in its entirety). When a portion of the biomolecule that has a probe hybridized to it enters the sensing volume, the potential may change further.

For purposes of simplification, description of the embodiments of the present invention may refer to the biomolecules as "DNA." It should be understood that such references are not intended to be limiting, and that references to DNA are intended to include all of the defined biomolecules described above, i.e., DNA, RNA, proteins, and polypeptides.

Typically, a DNA fragment will have two or more positions where probes are hybridized. As the DNA is translocated through a fluidic channel having multiple detector volumes, the locations where the probes are hybridized to the DNA also move through each of the detector volumes in turn. An electrical property, typically electrical potential, in each detector volume is monitored and changes in that property are recorded. When two or more probes, located at different positions on the target DNA, reside in different detector volumes at the same time, the distance between the probes can be determined directly, based on a predetermined, known distance between each of the detection volumes. The distance between any two probes may be determined by noting which detector volumes show detection for that pair of probes. Such detection is referred to herein as "coincident detection." As the spacing of the sensing electrodes, and thereby detector volumes, is known, coincident detection of probes in two detector volumes allows one to determine with great accuracy the distance between those probes on the target biomolecule independent of the velocity of the analyte.

Errors in the determination of the length of the analyte are dependent on the accuracy to which the distances between detector volumes are known or can be measured, either directly or through a calibration step. Because the determination of the distances between hybridization events relies on knowledge of the distance between sensing electrodes, such determination does not require that the biomolecule move with constant velocity through the device. In certain embodiments of the invention, the spacing between detector volumes may be chosen to vary in a fashion that enables the determination of a variety of different distances.

If two probes do not fill different detector volumes at exactly the same time, the time between the exit of one probe from a detector volume and the entrance of a different probe to that detector volume can be used to make adjustments to the distance between the two affected sensing elements to determine the distance between probes. In this case, the time used to correct the distance information should be small and will not add significant error to the distance measurement. Again, it is important to choose spacing for the sensing electrodes such that errors are reduced.

In one aspect, the invention features a device for determining the length of an analyte by detecting electrical signals. The device may comprise first and second fluid chambers separated by a structure and in fluid communication with one another across the structure. The structure may comprise one or more nanopores defined in a substrate and associated with electrodes to detect changes in an electrical property as target biomolecules translocate therethrough. Alternatively, the structure may comprise a fluidic channel defined in a substrate and a plurality of sensing electrodes disposed along a length of the fluidic channel. A plurality of sensing electrodes may be disposed along a length of the fluidic channel for detection of two or more electrical signals corresponding to two or more detector volumes disposed along the fluidic channel. The sensing electrodes may be configured for connection to a measurement tool for capturing the electrical signals corresponding to the detector volumes. The fluidic channel may include or consist essentially of a nanochannel or a microchannel. The relative positions of the sensing electrodes may be known. The captured electrical signals in conjunction with the relative positions of the sensing electrodes may be used to determine the length of the analyte and the relative positions of probes thereon.

One or more of the following features may be included in a device for determining a length of an analyte by detecting electrical signals. A data collection device may be configured for recording electrical signals captured by the measurement tool as a function of time. A computer may be in electrical communication with the data collection device, the computer programmed to determine which detector volumes record a change in electrical signal at the same time. An electronic circuit may be configured to output a signal only when two electrical signals corresponding to two detector volumes change at the same time.

In the case of a nanopore, a pair of electromotive electrodes may be positioned on either side of the pore. In that embodiment, the electrodes, while providing the electromotive force for translocation of the biomolecule analyte across the nanopore, may also serve to detect changes in an electrical property, such as current fluctuations, indicative of the presence of the analyte and probes as they transit the nanopore. Alternatively, in the case of a microchannel or nanochannel, a pair of electromotive electrodes may be disposed at a first end and a second end of the fluidic channel. The pair of electromotive electrodes may include macroscopic electrodes arranged to generate a constant, changing, or oscillating electrophoretic force in the fluidic channel for translocation of the analyte disposed therein.

The device may be configured such that positive pressure and/or a chemical gradient, with or without an electrophoretic force, may be used to drive the analyte through the nanopore or fluidic channel.

The substrate in which each nanopore or fluidic channel is formed may include or consist essentially of silicon, silicon dioxide, fused silica, and gallium arsenide. At least one of the sensing electrodes may include or consist essentially of platinum, gold, chrome, titanium, silver chloride, silver, and graphene.

A sensing element corresponding to a given detector volume may include two or more detector electrodes disposed on opposing sides of the fluidic channel and/or two or more detector electrodes disposed on a first side of the fluidic channel. In one preferred embodiment, two or more detector electrodes transverse the fluidic channel and are laterally displaced in the channel by a known or predetermined distance. A sensing element corresponding to a given detector volume may include a first detector electrode transversing the fluidic channel, and a second detector electrode on a side of the fluidic channel.

The measurement tool may include at least one of a voltmeter, an ammeter, or a field-effect transistor.

A plurality of nanopores or fluidic channels may be defined in the substrate. A voltage amplifier may be configured to amplify the two or more electrical signals.

When used in the present invention, nanopores may have a diameter selected from a range of about 1 nm to about 1 μm. More preferably the nanopore has a diameter that is between about 2.3 nm and about 100 nm. Even more preferably the nanopore has a diameter that is between about 2.3 nm and about 50 nm.

The fluidic channel may be a microchannel having a width selected from a range of about 1 μm to about 25 μm or a nanochannel having a width selected from a range of about 10 nm to about 1 μm. In the case of a microchannel, the depth may be selected from a range of about 200 nm to about 5 μm, whereas in the case of a nanochannel, the depth may be selected from a range of about 10 nm to about 1 μm. In either case, the channel may have a length selected from a range of about 1 μm to about 10 cm.

The device may include at least three pairs of detector electrodes, and a distance between detector volumes defined by a first and second pair of detector electrodes may be unequal to a distance between detector volumes defined by the second and third pair of electrodes.

The device may comprise at least three pairs of detector electrodes, a detector volume defined by a first pair of detector electrodes may be unequal to a detector volume defined by a second pair of detector electrodes, and a detector volume defined by the second pair of detector electrodes may be unequal to a detector volume defined by a third pair of detector electrodes.

Each detector volume may be associated with one or more detector electrodes.

In one embodiment, the fluid channel includes a first grouping of n laterally displaced, equally-spaced electrodes to provide n−1 equally-sized and spaced detector volumes, as well as additional groupings of laterally displaced, equally-spaced electrodes, where such additional groupings are separated from the first grouping by varying distances. As will be described in detail below, such electrode configurations allow the determination of highly accurate analyte lengths and probe spacing over a broad range of distances.

The description of elements of the embodiments of other aspects of the invention may be applied to this aspect of the invention as well.

In another embodiment, the invention features a method for determining a length of an analyte in a fluidic channel. A potential is applied along the fluidic channel. The analyte is translocated from a first end of the fluidic channel to a second end of the fluidic channel. Two or more electrical signals are detected as the analyte moves through the fluidic channel, the two or more electrical signals corresponding to two or more detector volumes of the fluidic channel. The two or more electrical signals are detected using a plurality of detector electrodes disposed along the length of the fluidic channel. The length of the analyte is determined by analyzing the two or more detected electrical signals. The fluidic channel is a nanochannel or a microchannel.

One or more of the following features may be included in a method for determining the length of an analyte. Applying the potential along the fluidic channel may generate an electrophoretic force which causes the analyte to translocate within the channel. Likewise, the analyte may be translocated by using a chemical gradient and/or a pressure differential, with or without an electrophoretic force.

Determining the length of the analyte may include identifying at least two detector volumes in which the analyte is sensed at a given time, and determining a distance between detector electrodes corresponding to the at least two detector volumes.

Determining the distance between probes hybrided on the analyte may include identifying at least two detector volumes in which the probes are sensed at a given time, and determining a distance between detector electrodes corresponding to such detector volumes.

An amount of analyte that partially fills the detector volume may also be determined by comparing the electrical signal caused by the analyte to a maximum signal caused by a sample biomolecule long enough to fill the detector volume entirely.

A correction factor may be applied to a measured length to determine an actual length of the analyte. As noted above, the analyte may include a biopolymer such as a DNA molecule or fragment, an RNA molecule or fragment, and/or a polypeptide or portion thereof. The biomolecule may be a single-stranded molecule. A portion of the analyte may be at least partially hybridized, such that the detected electrical signals indicate the presence of a probe bound to the analyte.

In accordance with embodiments of the invention, prior to being analyzed, the biomolecule, whether or not at least partially hybridized with a probe, may be incubated with a protein or enzyme that binds to the biomolecule and forms at least a partial coating along the biomolecule. If a protein is selected as the binding entity, the protein may include one or more of RecA, T4 gene 32 protein, f1 geneV protein, human replication protein A, Pf3 single-stranded binding protein, adenovirus DNA binding protein, and *E. coli* single-stranded binding protein.

In some embodiments, it is advantageous that the probes have a tag, particularly when used in conjunction with a protein coating step. In these embodiments, the portion of the probe that is intended to hybridize with the target biomolecule may be appended to a readily detectable dendrimer, bead or peptide. In one preferred embodiment, the tag comprises a biomolecule structure, such as a hairpin for example, with the portion of the probe intended to hybridize with the target biomolecule extending beyond the structure. In yet another preferred embodiment, the tag comprises a structure having loops or other identifiable features thereon which make the structure, and its corresponding probe, uniquely distinguishable from other tagged probes.

The description of elements of the embodiments of other aspects of the invention may be applied to this aspect of the invention as well.

In an aspect, the invention features a method for mapping of a biomolecule, including preparing an analyte by hybridizing a plurality of probes, each with specificity for the same sequence on the biomolecule, such that the plurality of probes attaches to portions of the biomolecule to produce a partially hybridized biomolecule. Using the methods and apparatus described herein, a map of the hybridization sites on the biomolecule may be generated. This map may be combined with short read data derived from this or other sources to generate sequence information for the target biomolecule.

In yet another aspect, the invention features a method for determining a sequence of a biomolecule, including preparing an analyte by hybridizing a first plurality of probes, each with specificity for the same sequence on the biomolecule, with the biomolecule such that the first plurality of probes attaches to portions of the biomolecule to produce a partially hybridized biomolecule.

The analyte may be disposed in a fluidic microchannel or nanochannel. A potential may be applied along the fluidic channel. The analyte may be translocated from a first end of the fluidic channel to a second end of the fluidic channel. Two or more electrical signals may be detected as the analyte moves through the fluidic channel, the two or more electrical signals corresponding to two or more detector volumes of the fluidic channel. The two or more electrical signals may be detected by using a plurality of detector electrodes disposed along the length of the fluidic channel, the detected electrical signals indicating locations of the hybridized probes along the biomolecule. The electrical signals may be analyzed to determine in which detector volumes probes bound to the biomolecule are located. At least a portion of the sequence of the biomolecule may be determined using a distance between detector electrodes corresponding to the detector volumes in which the probes are located. The process is then repeated using a second plurality of probes, each selected to have specificity for the same sequence on the biomolecule, but a different sequence than that to which the first plurality of probes is complementary. It is preferred that the second plurality of probes is complementary to a sequence on the biomolecule that shares a sub-region that is complementary to the first plurality of probes. With either or both probe sets, the probes may be provided with tags and/or the partially hybridized biomolecule may be coated with a protein or enzyme as described above.

In addition, one or more of the following features, previously described, may be included in the analysis of each probe set. An electrical potential may be applied along the fluidic channel to provide an electrophoretic translocating force therein. The analyte may be translocated by using a chemical gradient and/or a pressure differential, with or without the electrophoretic force. A distance between probes may be determined by using a coincident response of electrical signals corresponding to two or more detector volumes. A spacing between detector electrodes may be used to determine a maximum and/or minimum distance between probes.

In a preferred embodiment, the electrical signal will initially change when the biomolecule moves through a detector volume associated with two detector electrodes and further change when a portion of the biomolecule including a hybridized probe moves through the detector volume.

Determining the sequence of the biomolecule may include using a computer algorithm to process the two or more electrical signals.

It is noted that the second plurality of probes may be hybridized with the biomolecule either subsequent to, or in parallel with, the hybridization of the first plurality of probes.

In one embodiment, sequencing efficiency can be improved through the use of pools of probes rather than a single probe. Thus, the biomolecule to be sequenced may be hybridized with a collection of two or more probes each having a known and different specificity for a sequence on the biomolecule. The different probes may be tagged in a fashion that allows the devices disclosed herein to determine which probe is present on the biomolecule at each instance of hybridization. Alternatively, the identity of each probe may be unknown. The identity of one or more of the probes in the pool may be determined subsequently by hybridizing a probe that has an overlapping or otherwise related sequence specificity.

For example, a pool containing two probes with sequences ACTGCC and TAAGTC may be hybridized with a first target biomolecule sample and the distances between all instances of hybridization determined. Subsequently a pool of probes consisting of CTGCCA, CTGCCC, CTGCCG, and CTGCCT may be hybridized with a second target biomolecule sample having the same target sequence. The second pool of probes may hybridize to all of the positions that were hybridized by the probe ACTGCC in the first pool, as well as to additional sequences. The hybridization of both pools in separate experiments may allow a high confidence determination of which hybridization event was related to each of the probes in the first pool. Other pooling schemes may be envisaged by those skilled in the art.

A candidate sequence may be determined by ordering at least two probe map sequences using at least one probe map of positional information or a combination of overlapping probe map sequences and positional information. The first and second probe maps may include information about an error of the positional information for each probe.

A candidate sequence may be determined by ordering at least two probe sequences using at least one of (i) positional information and parameters relating to the error in positional information or (ii) a combination of overlapping sequences of the probe molecules and positional information and error in positional information.

In a further embodiment, the biomolecule may include a double-stranded target molecule.

In embodiments using double-stranded biomolecule targets, preparing the analyte may include contacting the biomolecule with a first probe having a first probe specificity for recognition sites of the biomolecule to form a first plurality of local ternary complexes. The first probe may have a first known recognition site sequence. The electrical signals may be used to determine positional information of the first plurality of local ternary complexes. Preparing the analyte may include contacting the biomolecule with a second probe having a second probe specificity for recognition sites of the biomolecule to form a second plurality of local ternary complexes. The second probe may have a second known recognition site sequence different from the first known recognition site.

Positional information of at least the first and second pluralities of local ternary complexes may be aligned to determine a sequence of the biomolecule.

The description of elements of the embodiments of other aspects of the invention may be applied to this aspect of the invention as well.

In yet another aspect, embodiments of the invention include a system for determining a length of an analyte, the system including an analyzing module that determines the length of the analyte based at least in part on a plurality of electrical signals captured by the devices described above.

The description of elements of the embodiments of other aspects of the invention may be applied to this aspect of the invention as well.

In another aspect, embodiments of the invention include an apparatus for determining a length of an analyte. The apparatus may include (a) a memory that stores code defining a set of instructions; and (b) a processor that executes the instructions thereby to determine the length of the analyte from two or more detected electrical signals captured by the devices described above.

The description of elements of the embodiments of other aspects of the invention may be applied to this aspect of the invention as well.

In another aspect, embodiments of the invention include an apparatus and system for sequencing a biomolecule. The system may include (a) a fluidic channel defined in a substrate; (b) a plurality of detector electrodes disposed along a length of the fluidic channel for detection of two or more electrical signals corresponding to two or more detector volumes disposed along the fluidic channel. The fluidic channel may be configured such that a biomolecule with at least a first plurality of probes attached thereto may pass therethrough, the detector electrodes may be configured for connection to a measurement tool for capturing the electrical signals corresponding to the detector volumes as the biomolecule passes through the fluidic channel. The fluidic channel may be a nanochannel or a microchannel, and relative positions of the detector electrodes may be known. The system may also include an analyzing module that determines at least a portion of the sequence of the biomolecule based at least in part on a plurality of the captured electrical signals. The analyzing module may be configured to perform one or more steps of the method described above.

In an aspect, embodiments of the invention provide a method for mapping a target biomolecule, the method including the steps of a) providing a single-stranded or double-stranded target biomolecule; b) providing an apparatus having first and second fluid chambers in fluid communication with one another, wherein the first and second fluid chambers are separated by a structure defining a nanopore, a microchannel, and/or a nanochannel, and wherein the apparatus includes at least one pair of electrodes defining at least one detector volume within the structure; c) providing at least one probe set, the probe set having a first plurality of identical probes that selectively hybridize to complementary regions on the target biomolecule; d) hybridizing the probes to the target biomolecule to provide a partially hybridized biomolecule having probes hybridized to complementary regions thereon; e) coating at least a portion of the partially hybridized biomolecule with one or more proteins; f) translocating the partially hybridized biomolecule through the at least one detector volume; g) monitoring, as a function of time, changes in an electrical property detected by the at least one pair of electrodes defining the at least one detector volume as the partially hybridized biomolecule translocates therethrough; and h) differentiating between hybridized and non-hybridized regions of the target biomolecule based at least in part on the detected changes in the electrical property in the at least one detector volume, thereby mapping at least a portion of the target biomolecule.

One or more of the following features may be included. The biomolecule may be, for example, a deoxyribonucleic acid, a ribonucleic acid, and/or a polypeptide. The structure may define at least one nanopore having a diameter of between about 1 nanometer and about 1 micrometer. The structure may define at least one microchannel having a width of between about 1 micrometer and about 25 micrometers. The structure may define at least one nanochannel having a width of between about 10 nanometers and about 1 micrometer. The at least one probe set may include hybridizing polyamides. The at least one probe set may include oligomers of non-cognate bases. For example, the at least one probe set may include DNA, RNA, locked nucleic acid, and/or peptide nucleic acid. The at least one probe set may include an antibody and/or a fragment thereof. The at least one probe set may also include hybridizing oligonucleotides having n contiguous bases capable of hybridizing to complementary regions on the biomolecule, where n is an integer from 4 to 12. The at least one probe set may also include gapped probes, and the gapped probes may have 6 contiguous bases capable of hybridizing to complementary regions on the biomolecule. In addition, at least a portion of the probes in the at least one probe set each may have attached thereto a detectable tag, and the tag may not hybridize with the biomolecule.

The coating step may include at least partially coating at least one of the partially hybridized biomolecule and the detectable tag with one or more proteins. The coating step may also include at least partially coating the partially hybridized biomolecule and the detectable tag with one or more proteins. The one or more proteins in the coating step may include one or more of RecA, T4 gene 32 protein, f1 geneV protein, human replication protein A, Pf3 single-stranded binding protein, adenovirus DNA binding protein, and/or $E.$ $coli$ single-stranded binding protein. The tag may include a detectable identification region, thereby facilitating detection of the specific probe set to which the tag is attached. The tag may also include a structured biomolecule, and the structured biomolecule may have a hairpin structure. The tag may include a detectable identification region, the detectable identification region having a unique pattern of detectable loops formed by the structured biomolecule.

The partially hybridized biomolecule may be translocated through the at least one detector volume using electrical energy, a pressure gradient, a chemical gradient, and/or a combination thereof.

The changes in the electrical property may be changes in electrical potential.

The structure may define a nanopore, and the at least one pair of electrodes may define the at least one detector volume across the nanopore. The structure may define a microchannel, and the two paired electrodes of one or more of the at least one pair of electrodes may be (i) laterally offset with respect to each other to define a detector volume therebetween, and/or (ii) positioned across the channel with substantially no lateral offset with respect to each other. The structure may define a nanochannel, and the two paired electrodes of one or more of the at least one pair of electrodes may be (i) laterally offset with respect to each other to define a detector volume therebetween, and/or (ii) positioned across the channel with substantially no lateral offset with respect to each other.

In certain embodiments, the method further includes sequencing at least a portion of the target biomolecule by repeating steps d) to h) for each of a plurality of different probe sets having a known sequence, wherein the known sequences of the probes used in subsequent hybridizations at least partially overlap such that gaps in a sequence of the target biomolecule are filled in with the known sequences of the subsequently used probe set(s).

The description of elements of the embodiments of other aspects of the invention may be applied to this aspect of the invention as well.

In another aspect, embodiments of the invention provide a method for sequencing a target biomolecule, the method including the step of processing the biomolecule map derived using the method described above along with short-read data, thereby identifying at least a partial sequence of the target biomolecule.

The description of elements of the embodiments of other aspects of the invention may be applied to this aspect of the invention as well.

In another aspect, embodiments of the invention provide a method for sequencing a target biomolecule, including the steps of a) providing a single-stranded or a double-stranded target biomolecule; b) providing an apparatus having first and second fluid chambers in fluid communication with one another, wherein the first and second fluid chambers are separated by a structure defining a nanopore, a microchannel, and/or a nanochannel, and wherein the apparatus includes at least one pair of electrodes defining at least one detector volume within the structure; c) providing at least two probe sets, each of the probe sets including a plurality of identical probes that selectively hybridize to complementary regions on the target biomolecule, each probe set hybridizing to a different complementary region, wherein at least one region complementary to the first probe set shares a subregion that is complementary to the second probe set; d) hybridizing the first probe set to a first sample of the target biomolecule to provide a first partially hybridized biomolecule sample having first probes hybridized to complementary regions thereon; e) at least partially coating the first partially hybridized biomolecule sample with one or more proteins; f) translocating the first partially hybridized biomolecule sample through the detector volume; g) monitoring, as a function of time, changes in an electrical property detected by the at least one pair of electrodes defining the at least one detector volume as the first partially hybridized biomolecule sample translocates therethrough; h) differentiating between hybridized and non-hybridized regions of the first target biomolecule sample based at least in part on the detected changes in the electrical property in the at least one detector volume; i) hybridizing the second probe set to a second sample of the target biomolecule to provide a second partially hybridized biomolecule sample having second probes hybridized to complementary regions thereon; j) at least partially coating the second partially hybridized biomolecule sample with one or more proteins; k) translocating the second partially hybridized biomolecule sample through the detector volume; l) monitoring, as a function of time, changes in an electrical property detected by the at least one pair of electrodes defining the at least one detector volume as the second partially hybridized biomolecule sample translocates therethrough; m) differentiating between hybridized and non-hybridized portions of the second target biomolecule sample based at least in part on the detected changes in the electrical property in the at least one detector volume; n) assembling correlated data sets from the first target biomolecule sample and the second target biomolecule sample, thereby sequencing at least a portion of the target biomolecule.

One or more of the following features may be included. The biomolecule may be, for example, a deoxyribonucleic acids, a ribonucleic acid, and/or a polypeptide. The structure may define at least one nanopore having a diameter of between about 1 nanometer and about 1 micrometer. The structure may define at least one microchannel having a width of between about 1 micrometer and about 25 micrometers. The structure may define at least one nanochannel having a width of between about 10 nanometers and about 1 micrometer. At least one of the first or second probe sets may include hybridizing polyamides. At least one of the first or second probe sets may include oligomers of non-cognate bases. The at least one of the first or second probe sets may include at least one of DNA, RNA, locked nucleic acids, and/or peptide nucleic acids. At least one of the first or second probe sets may include antibodies and/or fragments thereof.

At least one of the first or second probe sets may include hybridizing oligonucleotides having n number of contiguous bases capable of hybridizing to complementary regions on the biomolecule, where n is an integer from 4 to 12. At least one of the first or second probe sets may include gapped probes. The gapped probes may have 6 contiguous bases capable of hybridizing to complementary regions on the biomolecule. At least a portion of the probes in at least one of the first or second probe sets each may have attached thereto a detectable tag. The tag may not hybridize with the biomolecule. The coating step may include at least partially coating at least one of the partially hybridized biomolecule and the detectable tag with one or more proteins. The coating step may include at least partially coating the partially hybridized biomolecule and the detectable tag with one or more proteins. The one or more proteins in the coating step may include RecA, T4 gene 32 protein, f1 geneV protein, human replication protein A, Pf3 single-stranded binding protein, adenovirus DNA binding protein, and $E.\ coli$ single-stranded binding protein. The tag may include a detectable identification region unique to its probe set, thereby allowing the specific probe set with which the tag is included to be identified. The tag may include a structured biomolecule, and the structured biomolecule may have a hairpin structure. The tag may include a detectable identification region that has a unique pattern of detectable loops formed in the structured biomolecule.

The first and second partially hybridized biomolecule samples may be translocated through the detector volume using electrical energy, a pressure gradient, a chemical gradient, and/or a combination thereof.

The changes in the electrical property may be changes in electrical potential.

The structure may define a nanopore, and the at least one pair of electrodes may define at least one detector volume across the nanopore. The structure may define a microchannel, and the two paired electrodes of the one or more of the at least one pair of electrodes may be (i) laterally offset with respect to each other to define a detector volume therebetween and/or (ii) positioned across the channel with substantially no lateral offset with respect to each other. The structure may define a nanochannel, and the two paired electrodes of one or more of the at least one pair of electrodes may be (i) laterally offset with respect to each other to define a detector volume therebetween and/or (ii) positioned across the channel with substantially no lateral offset with respect to each other.

In certain embodiments, the at least two probe sets comprises a series of different probe sets each having a known sequence, the method further comprising repeating steps d) to h) for each of the series of different probe sets to produce a series of data sets differentiating between hybridized and non-hybridized portions of the target biomolecule, wherein step n) comprises assembling the series of data sets corresponding to the series of hybridizations to thereby sequence at least a portion of the target biomolecule.

The description of elements of the embodiments of other aspects of the invention may be applied to this aspect of the invention as well.

In another aspect, embodiments of the invention include an apparatus for analyzing a target biomolecule, including a) first and second fluid chambers in fluid communication with one another, wherein the first and second fluid chambers are separated by a structure defining at least one nanopore; b) at least one pair of electrodes positioned on opposite sides of the structure and defining a detector volume therethrough, the electrodes being in communication with an electrical signal detector and data collection device for respectively detecting and recording changes in an electrical property as the target biomolecule translocates through the detector volume; and c) a driving force generator for translocating the target biomolecule from the first fluid chamber to the second fluid chamber through the detector volume.

One or more of the following features may be included. The nanopore may have a diameter of between about 1 nanometer and about 1 micrometer. The changes in the electrical property may be changes in an electrical current applied across the detector volume. The driving force generator may include electrical energy, a pressure gradient, a chemical gradient, and/or a combination thereof.

The apparatus may further include a memory for storing code that defines a set of instructions, and a processor for executing the set of instructions to differentiate between hybridized and non-hybridized regions of the target biomolecule based at least in part on the detected changes in electrical property as the target biomolecule translocates through the at least one detector volume. In certain embodiments, the processor is configured to execute the set of instructions to assemble a series of data sets differentiating between hybridized and non-hybridized portions of the target biomolecule for each of a plurality of probe-target hybridizations, thereby sequencing at least a portion of the target biomolecule, wherein the sequences of the probes are known and at least partially overlap.

The description of elements of the embodiments of other aspects of the invention may be applied to this aspect of the invention as well.

In yet another aspect, embodiments of the invention include an apparatus for analyzing a target biomolecule, the apparatus including a) first and second fluid chambers in fluid communication with one another, the first and second fluid chambers being separated by a structure defining a nanochannel and/or a microchannel; b) at least one pair of electrodes laterally offset from one another along the channel and defining at least one detector volume therein, the electrodes being in communication with an electrical signal detector and data collection device for respectively detecting and recording changes in an electrical property as the target biomolecule translocates through the at least one detector volume; and c) a driving force generator for translocating the target biomolecule from the first fluid chamber to the second fluid chamber through the detector volume.

One or more of the following features may be included. The structure may define a nanochannel having a width between about 10 nanometers and about 1 micrometer. The nanochannel may have a depth between about 10 nanometers and about 1 micrometers. The nanochannel may have a length between about 1 micrometers and about 10 centimeters. The structure may define a microchannel having a width between about 1 micrometer and about 25 micrometers. The microchannel may have a depth between about 200 nanometers and about 5 micrometers. The microchannel may have a length between about 1 micrometers and about 10 centimeters. The changes in the electrical property may be changes in an electrical potential. The driving force generator may be electrical energy, a pressure gradient, a chemical gradient, and/or a combination thereof.

The apparatus may further include a memory for storing code that defines a set of instructions, and a processor for executing the set of instructions to differentiate between hybridized and non-hybridized regions of the target biomolecule based at least in part on the detected changes in electrical property as the target biomolecule translocates through the at least one detector volume. In certain embodiments, the processor is configured to execute the set of instructions to assemble a series of data sets differentiating between hybridized and non-hybridized portions of the target biomolecule for each of a plurality of probe-target hybridizations, thereby sequencing at least a portion of the target biomolecule, wherein the sequences of the probes are known and at least partially overlap.

The description of elements of the embodiments of other aspects of the invention may be applied to this aspect of the invention as well.

In another aspect, embodiments of the invention include an apparatus for analyzing a target biomolecule, the apparatus including a) first and second fluid chambers in fluid communication with one another, the first and second fluid chambers being separated by a structure defining a nanochannel and/or a microchannel; b) a plurality of electrodes each laterally offset from one another along the nanochannel and/or microchannel, thereby defining a plurality of detector volumes therein, the electrodes being in communication with an electrical signal detector and data collection device for respectively detecting and recording changes in an electrical property as the target biomolecule translocates through the at least one detector volumes; and c) a driving force generator for translocating the target biomolecule from the first fluid chamber to the second fluid chamber through the detector volumes.

One or more of the following features may be includes. The plurality of electrodes may include a first plurality of n electrodes, with each electrode being laterally offset by a predetermined distance along the nanochannel or microchannel, to thereby define n−1 detector volumes.

The apparatus may include a second plurality of m electrodes, with each electrode being laterally offset by a predetermined distance along the nanochannel or microchannel, to thereby define m−1 detector volumes.

The second plurality of electrodes may be laterally offset from the first plurality of electrodes by a distance greater than either the first or second predetermined distances.

A plurality of detector volumes may be defined in each nanochannel or microchannel, with the spacing between each detector volume being predetermined and unequal. For example, the spacing between the plurality of detector volumes may define a Golomb ruler.

The apparatus may include a first plurality of eleven electrodes, with each electrode being laterally offset along the nanochannel or microchannel by a distance approximating ten base pairs of the target biomolecule, to thereby define 10 detector volumes.

The apparatus may include a second plurality of eleven electrodes, with each electrode being laterally offset along the nanochannel or microchannel by a distance approximating ten base pairs of the target biomolecule, to thereby define 10 detector volumes, the second plurality of electrodes being laterally offset along the nanochannel or microchannel from the first plurality of electrodes by a distance approximating one hundred base pairs of the target biomolecule.

The apparatus may include a third plurality of eleven electrodes, with each electrode being laterally offset along the nanochannel or microchannel by a distance approximating ten base pairs of the target biomolecule, to thereby define 10 detector volumes, the third plurality of electrodes being laterally offset along the nanochannel or microchannel from the second plurality of electrodes by a distance approximating three hundred base pairs of the target biomolecule.

The apparatus may include a fourth plurality of eleven electrodes, with each electrode being laterally offset along the nanochannel or microchannel by a distance approximating ten base pairs of the target biomolecule, to thereby define 10 detector volumes, the fourth plurality of electrodes being laterally offset along the nanochannel or microchannel from the third plurality of electrodes by a distance approximating seven hundred base pairs of the target biomolecule.

BRIEF DESCRIPTION OF DRAWINGS

FIG. 7a is a graph and schematic diagram illustrating a fluidic channel transversed by 6 electrodes; an electrical signal is recorded as the biomolecule enters each detector volume (i.e., a volume associated with two electrodes);

FIGS. 8a-8i are graphs and schematic diagrams illustrating a biomolecule with hybridized probes being translocated from a first end to a second end of a fluidic channel disposed by 6 transverse detector electrodes and the resultant electrical signals;

FIG. 9c is an illustration of a Golomb ruler of length 6;

FIG. 10 is a schematic diagram illustrating an alternative arrangement of electrodes with varying distances between electrodes;

FIGS. 11a-11g are graphs and schematic diagrams illustrating a biomolecule with hybridized probes being translocated in a fluidic channel with detector electrodes having varying distances therebetween;

DETAILED DESCRIPTION

Figure 1:
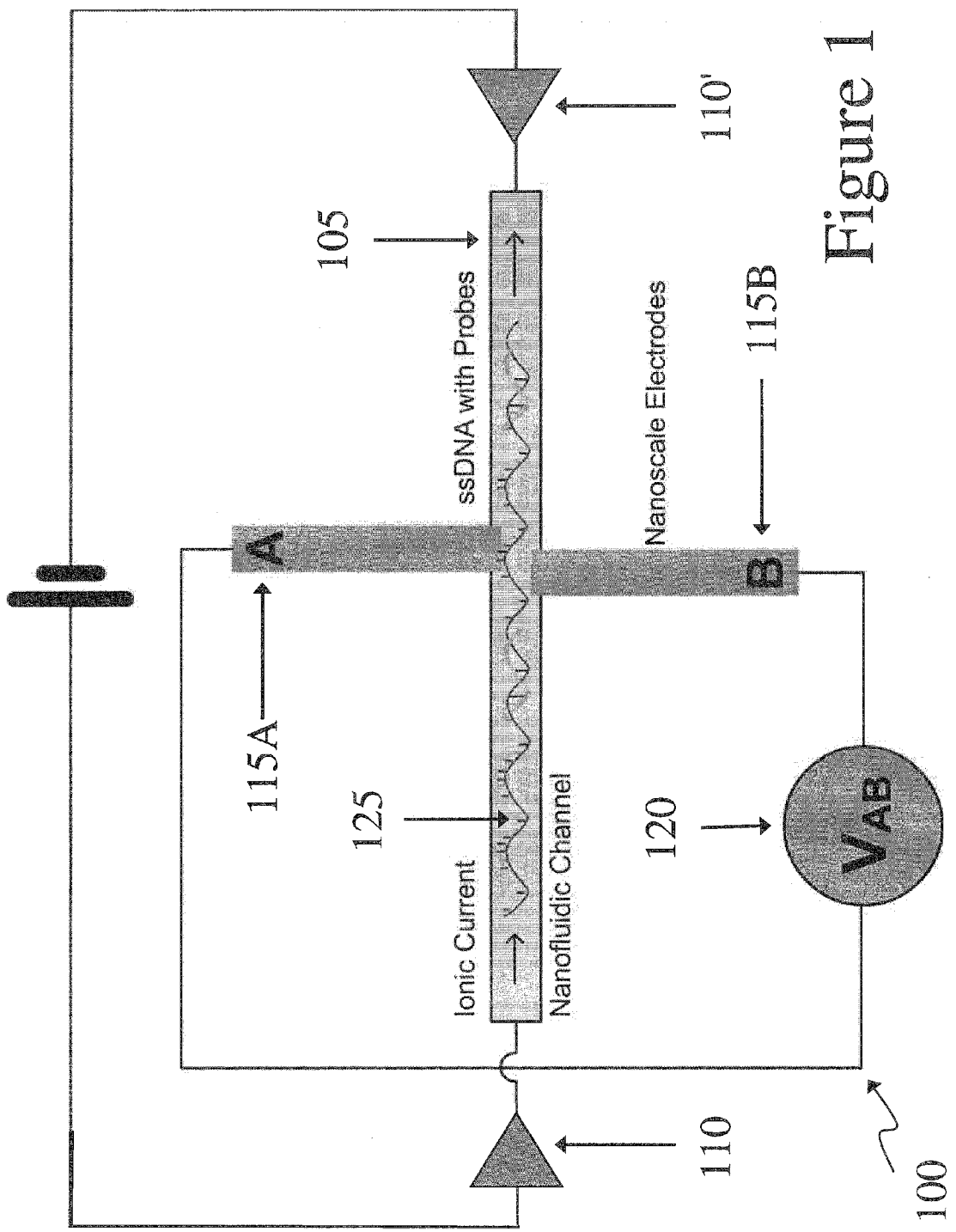
FIG. 1 is a schematic diagram illustrating a longitudinally displaced transverse electrode device configuration.

The use of electronic detection applied to DNA sequencing may help overcome the limitations associated with single-molecule detection. For example, Hybridization-Assisted Nanopore Sequencing (HANS), which uses nanopores to detect and locate the position of hybridization events (e.g., hybridized probes on a biopolymer), may provide highly accurate DNA sequence information, with long read lengths. The HANS method relies on detecting the position of hybridized probes on single molecules of the biomolecule to be sequenced or characterized. The resulting positional hybridization data is used to reconstruct sequence information of the target strand. The process for sequence reconstruction is similar to that for reconstructing sequence data from Sequencing by Hybridization (SBH) experiments with the important difference that the addition of positional information removes the inherent mathematical limitations of SBH and results in successful reconstruction of extremely long sequences.

The HANS method provides a number of benefits over other sequencing technologies. For example, the inherent nature of reconstructing data from multiple overlapping hybridization events reduces errors. Further, the rapid nature of the sensing allows for higher accuracy since coverage can be extensive without significantly impacting the timely production of data. Thus, a significant benefit of the HANS approach is the long read lengths obtainable by the method, which may be used to identify genomic rearrangements and/or reconstruct haplotypes from diploid organisms or separate genomes of related mixtures of, for instance, viral or microbial species.

In the HANS method, two reservoirs of solution are separated by a nanometer sized hole, or nanopore, that serves as a fluidic constriction of known dimensions. The application of a constant DC voltage between the two reservoirs results in a baseline ionic current that is measured. If an analyte is introduced into a reservoir, it may pass through the fluidic channel and change the observed current, due to a difference in conductivity between the electrolyte solution and analyte. The magnitude of the change in current depends on the volume of electrolyte displaced by the analyte while it is in the fluidic channel. The duration of the current change is related to the amount of time that the analyte takes to pass through the nanopore constriction. In the case of DNA translocation through a nanopore, the physical translocation is driven by the electrophoretic force generated by the applied DC voltage between the two reservoirs.

DNA can also be translocated through nanochannels by applying a DC voltage. See, e.g., Riehn, R. et al. *Proc. Nat. Acad. Sci.* 2005, 102, 10012, which is incorporated herein by reference in its entirety. Detection of DNA molecules in a nanochannel has been accomplished by applying a current through electrodes that are perpendicular to the nanochannel. See Liang, X.; Chou, S. Y. *Nano Lett.* 2008, 8, 1472, which is incorporated herein by reference in its entirety. As DNA passes between the electrodes the observed current passing between two electrodes disposed on the opposite side of the channel changes. The length of the DNA strand may be inferred from the time of passage of the strand past the electrodes.

Nanoscale pores that allow passage of biomaterials provide one tool for the analysis of biomolecules by determining the distance between hybridization sites. Unlike fluidic channels, the accurate determination of distance when employing nanopores relies on maintenance of a constant velocity of the biomolecule through the nanopore during the measurement. Extending nanopores into fluidic channels (e.g., nanochannels and microchannels) containing multiple sensing electrodes provides new uses and a new level of precision in biomolecule analysis.

The construction of various devices, including a fluidic channel device incorporating a plurality of electrode pairs as voltage or current detectors along its length is described below. These electrode pairs can detect changes in the conductivity of the fluid volume between them as biomolecules pass through the fluidic channel. Simultaneous changes in the conductivity at distant electrode pairs may allow for the determination of the length of the biomolecule. The degree of these changes may also allow for the determination of the location of probes on the biomolecule. This determination may be used in the mapping, sequencing and identification of biomolecules.

The technology disclosed herein allows the determination of biomolecule length and distances between hybridization positions. In the case of systems using fluidic channels, such determinations may be made without the need to determine the velocity of the biomolecule.

As used herein, "target" means a biomolecule, for example, having sequence information that is to be determined using embodiments of the present invention. The target biomolecule may be a biopolymer such as a deoxyribonucleic acid, a ribonucleic acid, a protein, or a polypeptide. The target biomolecule may be single- or double-stranded.

As used herein, a "probe" means any molecule or assembly of molecules capable of sequence—specific covalent or non-covalent binding to a target molecule. A probe may be, but is not limited to, a DNA sequence, an RNA sequence, a locked nucleic acid (LNA) sequence, a peptide nucleic acid (PNA) sequence, antibodies or antibody fragments. The terms "nucleotide" and "base" are used interchangeably and mean a molecule consisting of a phosphate group, a sugar and one of five nitrogen-containing bases that can make up DNA or RNA polynucleotide chains or strands. For DNA, the nitrogen-containing bases include cytosine (C), adenine (A), guanine (G) and thymine (T) and the sugar is a 2-deoxyribose. For RNA, the deoxyribose sugar is replaced by a ribose sugar instead of deoxyribose and uracil bases (U) instead of thymine bases (T). The probes may include oligomers of non-cognate bases. As used herein, "non-cognate" is intended to mean probes that bind to target sequences whose identity is not known. As noted above, in certain instances, further description of the embodiments of the present invention may refer to "DNA." Unless otherwise specified, such use is for simplification only, and it should be understood that such references are not intended to be limiting, and that references to DNA are intended to include all of the defined biopolymers described above, i.e., DNA, RNA, LNA, PNA, proteins, and polypeptides.

The present invention also envisions the use of "gapped" probes, i.e., probes having a pattern of universal and designate nucleotides. A "universal" nucleotide, as used herein, is intended to mean a chemical entity which, when present in the probe, will engage in a base-pairing relationship with any natural nucleotide. Exemplary universal nucleotides include 5-nitroindole and 3-nitropyrrole. Further description of gapped probes may be found in U.S. Pat. Nos. 6,689,563; 7,034,143 & 7,071,324, the teachings of which are incorporated herein by reference.

The term "tag" means a moiety that is attached to a probe in order to make the probe more visible to a detector. These tags may be proteins, double-stranded DNA, single-stranded DNA or other molecules. In one preferred embodiment, such tags include DNA structures, such as hairpins, while in other embodiments, tags may include dendrimers, beads, or peptides. When used with nanopore detectors, tags may have either a larger volume than the probe or a different charge so that they slow translocation of the biomolecule through the nanopore or fluidic channel.

A DNA probe "library" is a collection of DNA probes of a fixed length that includes a large number of, or possibly all, possible sequence permutations of a given length. A plurality of probes may be made up of multiple copies of the same probe with the same sequence selectivity or be made up of two or more probes with different sequence selectivity.

A "probe map" means a data set containing information related to the sites along a target sequence at which a probe preferentially binds. The data set may include absolute positional information referenced to a known sequence, relative information related to distances between binding sites, or both.

Error in the length information is the uncertainty of the final length of a biomolecule. This uncertainty may arise from a discrepancy between multiple readings or may be an inherent part of the system based on the placement of sensing electrodes. The error may also result from the behavior of the analyte in a fluidic channel (e.g., a nanochannel). Non-uniform coiling, kinking, bending, and stretching of the analyte may contribute to the error. The determination of the error in the length may be determined by statistical analysis.

Error in positional information is the uncertainty of the distance between hybridized molecules. This uncertainty may arise for the same reasons as for the uncertainty in the length information. The determination of the error in the distance between probes may be determined by statistical analysis.

A "partially hybridized biomolecule" is created when the entire length of a sequence-selective probe binds to a portion of the length of the target biomolecule.

A "detector volume" is the volume of electrolyte between two detector electrodes, through which resistance or voltage is measured by the detector electrodes. The data set may be stored in computer media. Further details of the characteristics of probe and spectrum maps may be found in U.S. Patent Publication No. 2009-0099786 A1, which is incorporated herein by reference in its entirety.

Fabrication of Fluidic Channel and Detector Electrodes

Various electrical signals may be detected with the detector electrodes described herein. In some embodiments, the detected electrical signal may be a voltage. Examples of such configurations are described in detail below with respect to FIGS. 1-5. In other embodiments, a current or another electrical signal may be detected (see FIG. 6).

In one embodiment, FIG. 1 shows a device (also referred to herein as a system or apparatus) 100 including a fluidic channel 105, e.g., a micro- or nanochannel, a pair of electromotive electrodes 110, 110', and a pair of detector electrodes 115A, 115B. The detector electrodes 115A, 115B may be in electrical connection with an electrical signal detector 120 for detecting and recording changes in an electrical property, such as a voltmeter. The fluidic channel 105 may be defined in a substrate including silicon, silicon dioxide, fused silica, and/or gallium arsenide. The fluidic channel may contain an electrolytic solution, with electromotive electrodes 110, 110' being disposed on a first and a second end of the fluidic channel.

The electromotive electrode 110, 110' pair may include at least one anode 110' and cathode 110 in contact with the electrolytic solution to provide a constant or changing current to drive the analyte 125 through the fluidic channel, thereby functioning as a driving force generator, generating electrical energy. In an alternate embodiment, the driving force generator may be a pressure differential, such as a positive pressure, that may be used to drive the analyte through the fluidic channel. Pressure may be supplied with a fluid pump or with a pressurized gas line. Other methods of applying a driving force for the analyte may be envisioned by one of skill in the art. In some embodiments, the driving force generator may include a chemical potential gradient that may be used to move molecules through the fluidic channel. Chemical potential gradients may be created with concentration gradients. For instance, a fluidic channel may have one end immersed in a fluid that has a higher salt concentration than the fluid at the other end of the fluidic channel. The differential in salt concentration at the ends of the fluidic channel may cause an osmotic pressure that can drive analytes through the fluidic channel. These methods may be used alone or in any combination.

As the analyte 125, which may be any biomolecule including, but not limited to, polypeptides, DNA or RNA, passes through the fluidic channel 105, it may pass between the pair of detector electrodes 115A, 115B (each individually referred to herein as "A" and "B"). The detector electrodes 115A, 115B contacting the fluidic channel 105 are used to monitor the changes in conductance of the electrolytic volume between them. The changes in conductance between the detector electrodes 115A, 115B may be measured using an electrical signal detector 120, e.g., a voltmeter.

Figure 2:
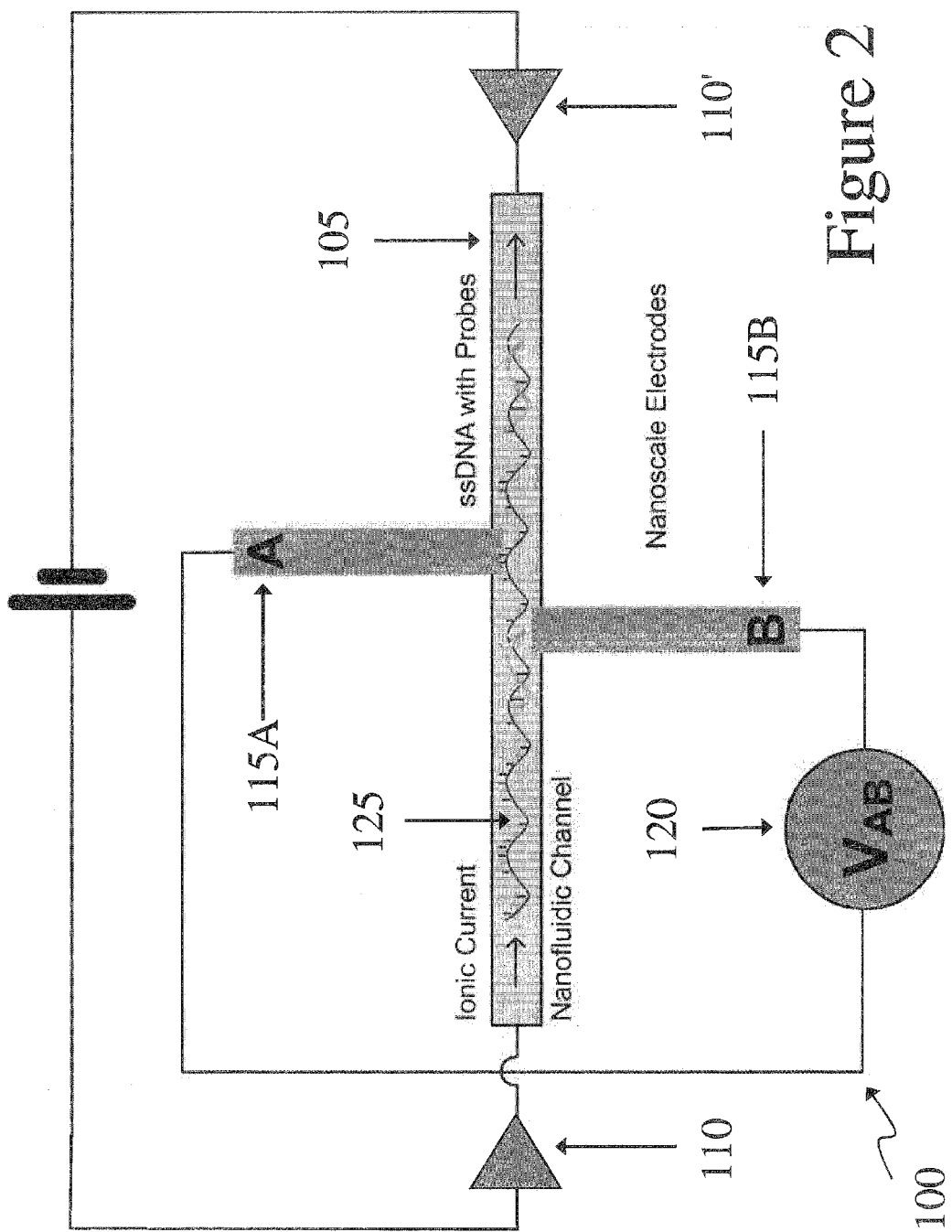
FIG. 2 is a schematic diagram illustrating a longitudinally displaced transverse electrode device configuration.
Figure 3:
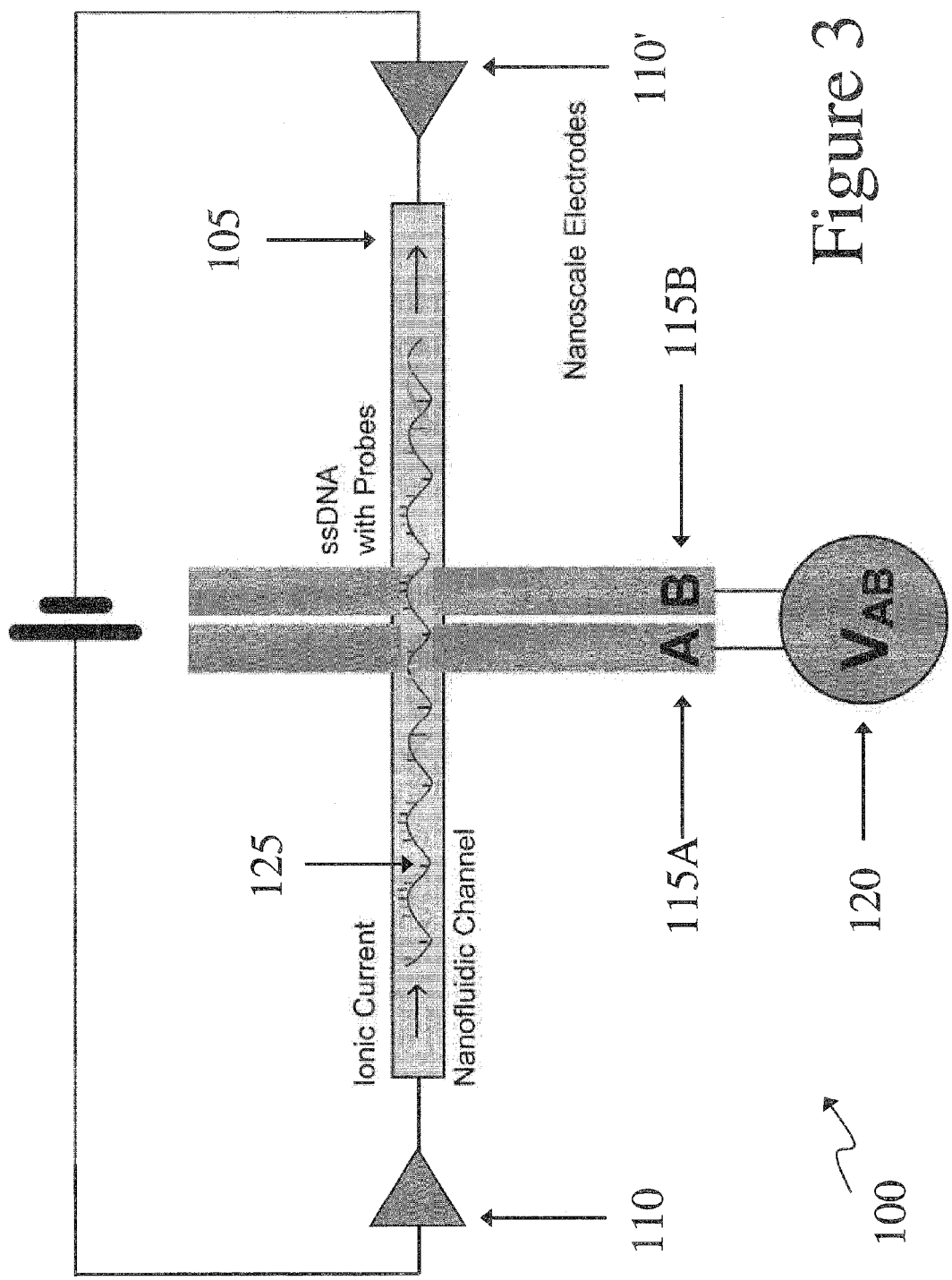
FIG. 3 is a schematic diagram illustrating a longitudinally displaced continuous transverse nanoscale electrode device configuration.
Figure 4:
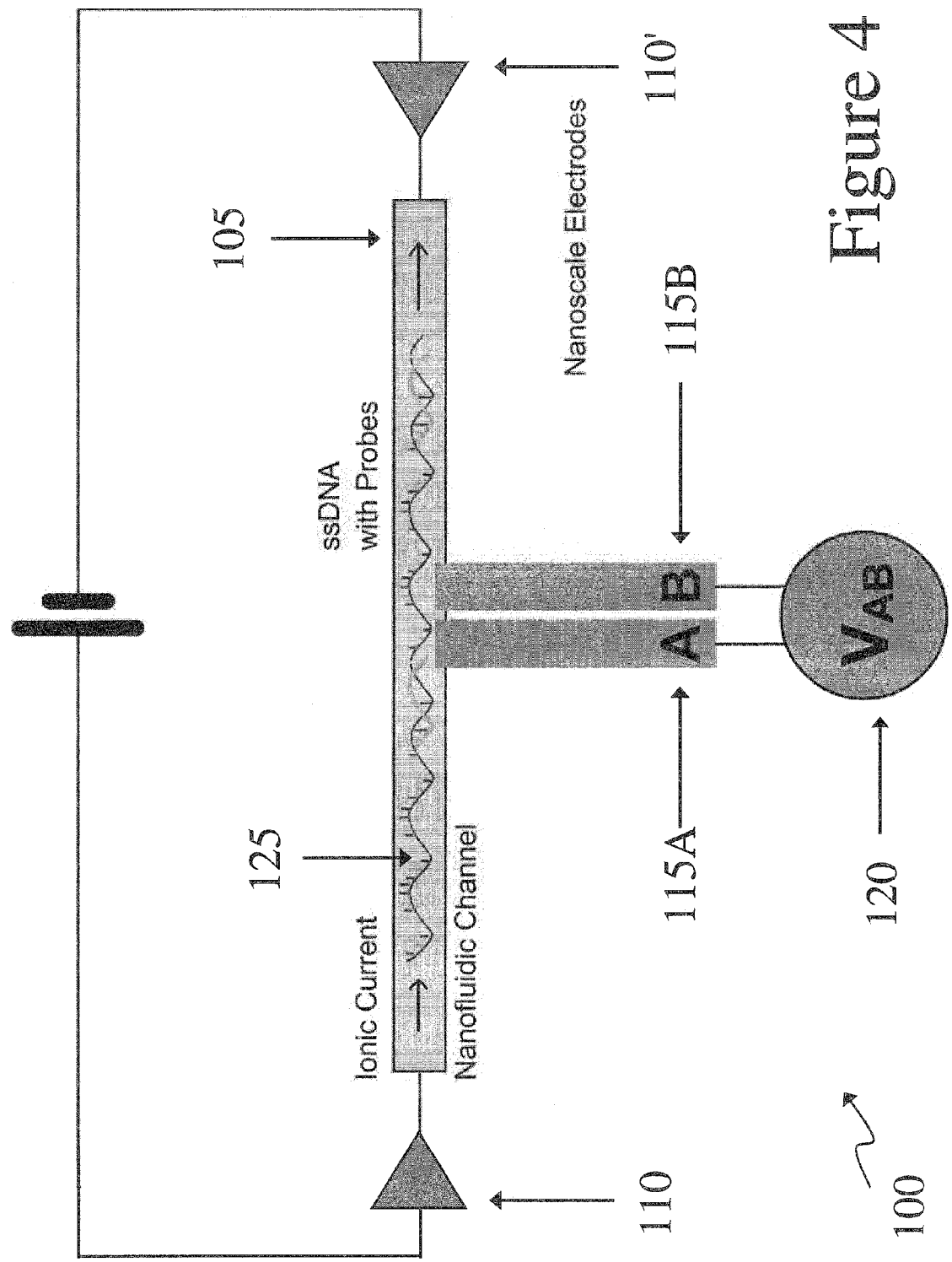
FIG. 4 is a schematic diagram illustrating a longitudinally displaced nanoscale electrode device configuration with electrodes disposed on the same side of a channel.

By making the lateral distance, e.g., along a length of the fluidic channel 105, between detector electrodes 115A, 115B small, the device 100 retains high sensitivity for an analyte 125 passing therethrough. Each detector electrode 115A, 115B in the pair may be disposed on opposite sides of the fluidic channel 105 as in FIG. 1, where tips of each detector electrode 115A, 115B in contact with the electrolytic solution are entirely or partially across from one another, or FIG. 2, in which the tips of the detector electrodes 115A, 115B are not across from each other, but are rather longitudinally displaced with respect to one another by a selected distance. Alternatively, each detector electrode 115A, 115B in a pair may cross, or transverse, the fluidic channel 105, as shown in FIG. 3. Referring to FIG. 4, in a third arrangement, two detector electrodes 115A, 115B in a pair may be on the same side of the fluidic channel 105.

The lateral distance along the channel, defined by the lateral offset between a pair of detector electrodes is referred to herein as the "detector volume". As will be described below, the apparatus is not limited to the use of one pair of detector electrodes; rather, systems with multiple detector electrodes are envisioned as well. For example, a system using three electrodes may be constructed, whereby the lateral offset distance between first and second detector electrodes (a first electrode pair) defines a first detector volume, and the lateral offset distance between second and third detector electrodes (a second electrode pair) defines a second detector volume. Such systems will be described in greater detail below.

The devices 100 described herein may be nanochannel devices formed by the fabrication of a fluidic channel 105 typically having nanoscale dimensions, and the fabrication of nanoscale electrodes. In some embodiments, the fluidic channel may have microscopic dimensions, e.g., may be a microchannel. A typical device may also have a microscale fluidic structure for introduction of buffers and samples. Thus, the techniques described herein employing nanochannels are also applicable to devices including microchannels. Some devices may include multiple nanochannels or microchannels, i.e., arrays. Some or all of the structures may also be sealed with a cap in order to provide closed channels.

Fluidic channels may be formed in the substrate by, e.g., lithographic and etch steps. The substrate may be, e.g., a silicon-on-insulator wafer, with, for example, a (100) Si surface, a Si wafer, a fused silica, or a gallium arsenide substrate.

Lithography in the sub-100 nanometer (nm) regime may be performed by various techniques, including the following: electron beam lithography (EBL), nanoimprint lithography (NIL) or deep ultraviolet optical lithography (DUV OL). See Liang, X.; Morton, K. J.; Austin, R. H.; Chou, S. Y., Single sub-20 nm wide, centimeter-long nanofluidic channel fabricated by novel nanoimprint mold fabrication and direct imprinting, *Nano Lett.* 2007, 7, 3774-3780; Austin, M. D.; Ge, H.; Wu, W.; Li, M.; Yu, Z.; Wasserman, D.; Lyon, S. A.; Chou, S. Y., Fabrication of 5 nm line width and 14 nm pitch features by nanoimprint lithography, *App. Phys. Lett.* 2004, 84, 5299-5301; and Guo, J., Recent progress in nanoimprint technology and its applications, *J. Phys. D: Appl. Phys.* 2004, 37, R123-R141, which are incorporated by reference herein in their entirety. The current industry standard in micro- and nanofabrication is optical lithography due to its low cost and high throughput. At present, optical lithography has been successfully used in the mass production of devices with critical dimensions as small as 32 nm. EBL and NIL are presently used extensively in academic research environments due to their versatility and capability of producing sub-10 nm features reproducibly. Any of these methods may be used to pattern the fluidic channels described herein.

The removal of material for the formation of the fluidic channels may be performed by, e.g., etching. Wet etching includes the immersion of the material in a solution capable of selective removal. Dry etching, i.e., reactive ion etching (RIE), involves the exposure of the sample to a charged plasma. For the resolution and control required of nanoscale fabrication, RIE is preferable due to its consistency, controllability, and efficiency. Microfluidic channels or reservoirs leading to the nanoscale channels may be etched using either wet or dry methods.

As stated previously, the fluidic channel may be a microchannel having a width selected from a range of about 1 μm to about 25 μm or a nanochannel having a width selected from a range of about 10 nm to about 1 μm. In the case of a microchannel, the depth may be selected from a range of about 200 nm to about 5 μm, whereas in the case of a nanochannel, the depth may be selected from a range of about 10 nm to about 1 μm. The fluidic channels may have a length selected from a range of, e.g., 1 micrometer (μm) to 10 centimeters (cm). It should be understood, however, that in each case presented herein, the dimensional ranges are intended to be exemplary only, and should not be considered as limitations.

After the fluidic channels are formed, detector electrodes are fabricated. Numerous metal deposition techniques suitable for fabrication of electrodes exist in conventional microfabrication process flows. Each technique has positive and negative attributes and a list of the materials that may be deposited using that technique. The three primary techniques are: electron beam evaporation, thermal evaporation, and sputtering. The detector electrodes have thicknesses ranging from 5 nm to 100 nm at the point where the electrodes intersect the fluidic channels. The electrodes may be wider and/or thicker in regions distal to the fluidic channels and approaching contact pads disposed at the perimeter of the device.

To complete the device, a cap layer may be introduced to prevent evaporation of liquid from the fluidic channel. The cap may be formed over just the nanoscale fluidic paths or over all of the fluidic channels. In the latter case, the cap structure preferably has holes or ports to allow for the introduction of fluid and samples into the fluidic paths. In another embodiment, the entire substrate, i.e., wafer, may be capped. The cap may be made of a glass plate such as borosilicate glass, phosphosilicate glass, quartz, fused silica, fused quartz, a silicon wafer, a gallium arsenide wafer, or other suitable substrates. Various techniques are suitable for accomplishing this step including anodic bonding. In anodic bonding, an underlying silicon wafer and a glass substrate are pressed together and heated while a large electric field is applied across the joint. Anodic bonding has been demonstrated to form a strong bond between a silicon wafer and the capping substrate. Direct silicon bonding has been used to join two silicon wafers. The latter method involves pressing the two wafers together under water. Other methods use an adhesive layer, such as a photoresist, to bond the cap to the substrate.

More particularly, an exemplary fabrication process for defining the fluidic channel and detector electrodes is as follows. A suitable substrate, such as a conventional (100) p-type silicon wafer, is thermally oxidized in a hydrated atmosphere to grow a thick (e.g., >1 μm) silicon-dioxide ($SiO_2$) layer. This $SiO_2$ layer may serve as insulation between subsequently formed adjacent metal electrodes, and may also reduce overall device capacitance.

Using conventional high resolution optical lithography, the pattern of the fluidic channel may be transferred to a first photoresist masking layer. RIE with an anisotropic etch species, such as $CF_4$, may be used to transfer the pattern into the $SiO_2$ layer to define a trench that functions as a fluidic channel in the completed device. The preferred width and depth of the fluidic channel may be determined by the requirements for the device sensitivity. The smaller the volume of the fluidic channel between two electrodes, the more sensitive the device is. Fluidic channel size, width, and depth, may also be determined by the size or behavior of the analyte. In one embodiment, the device described herein is used to detect strands of DNA. It may be desirable to fabricate the fluidic channel with dimensions that extend the DNA strand within the channel. For instance for double-stranded DNA, it has been found that the use of fluidic channels with dimensions of 100 nm or less are able to extend the biomolecule. See Tegenfeldt, J. O et al. *The dynamics of genomic-length DNA molecules in* 100-*nm channels*. Proc. Nat. Acad. Sci. USA, 2004, 101, 10979-10983, which is incorporated by reference herein in its entirety. Upon completion of the dry etch procedure, residual resist is removed and the substrate vigorously cleaned.

Following the etching of the fluidic channel, embedded metal detector electrodes are fabricated. Conventional high resolution optical lithography may be used to transfer the metal electrode pattern to a second photoresist masking layer. RIE with an anisotropic etch species, such as $CF_4$, may be used to transfer the pattern into the $SiO_2$ layer. The depth of these trenches may be less than, equal to, or greater than the depth of the fluidic channel. In one embodiment, the depth of these trenches exceeds or equals the depth of the fluidic channel. Upon completion of pattern transfer to the $SiO_2$ layer, a thin metal adhesion promotion layer may be deposited. A suitable layer is tantalum with a thickness of 30-50 Å, deposited via electron beam evaporation. Next, the electrode material is deposited without exposing the substrate to atmosphere. A preferred metal for the bulk of the electrodes is platinum, also deposited via electron beam evaporation. Other examples of suitable metals include gold, chrome, titanium, silver chloride, silver, and graphene. The thickness of the metal is dictated by the depth of the etched fluidic channels, such that the resultant metal trace is approximately planar with a top surface of the $SiO_2$ layer. Upon completion of the metal deposition, the substrate is immersed in a photoresist solvent that lifts-off excess metal from the surface and the substrate is vigorously cleaned. Chemical-mechanical polishing (CMP) may be performed to remove excess metal extending over the $SiO_2$ top surface, thereby planarizing a top surface of the metal to be level with the $SiO_2$ top surface.

To complete the fabrication of the device, a cap layer is preferably adhered to the device surface to provide a leak-free seal, enabling fluidic conduction. Preferred cap materials include borosilicate glass, fused silica, fused quartz, quartz, or phosphosilicate glass. Holes may be created in the cap layer to provide access to fluidic inlet, fluidic outlet, and metal electrodes. A typical method for making holes in glass wafers is ultrasonic etching, which allows for highly controllable pattern transfer to glass substrates. Anodic bonding may then be used to bond the glass cap layer to the underlying substrate, e.g., silicon wafer. The anodic bonding of two layers provides a strong and leak-free seal.

An exemplary device with a pair of such nanoscale detector electrodes is illustrated in FIG. 1, i.e., electrodes 115A, 115B. Electric current is transferred in the form of ionic flow in an electrolyte solution confined in the fluidic channel (e.g., a nanochannel). The role of the electrolyte is to maintain a uniformly distributed electric field in the fluidic channel. Typical electrolyte solutions have been described in applications of electrophoresis to separations of DNA molecules. The most common electrolytes for electrophoretic separation of DNA are Tris boric acid EDTA (TBE) and tris acetate EDTA (TAE). See, e.g., Sambrook, J.; Russell, D. W. *Molecular Cloning: A Laboratory Manual* $3^{rd}$ ed. *Cold Spring Harbor Press*, 2001, which is incorporated by reference herein in its entirety. However, any conductive medium may be used.

Operation of Fluidic Channel

During operation, a current is supplied by applying a potential to a pair of electromotive electrodes 110, 110', e.g., macroscopic electrodes disposed at opposing ends of the fluidic channel 105 and in contact with the electrolytic solution. The electromotive electrodes 110, 110' are preferably in electrical communication with wires leading to the ends of the fluidic channels as illustrated in FIGS. 1-6.

The electromotive electrodes 110, 110' may generate a constant or varying electrophoretic force in the fluidic channel 105 for translocation of an analyte 125 disposed therein. The voltage between the electromotive electrodes 110, 110' may be constant or it may be changed over the course of a measurement. For instance, it may be desirable to reduce the voltage once a DNA molecule has entered the fluidic channel 105 and before the DNA molecule has entered the volume between the detector electrodes 115A, 115B, in order to slow the passage of the DNA molecule through the detector volume. Alternatively, a pressure differential and/or a chemical potential gradient, with or without electrophoretic force, may be used to drive the analyte 125 through the fluidic channel 105. Controlling the rate of passage of the DNA molecule through the detector volume allows for more accurate detection, measurement, and analysis of the DNA.

As an example of the placement of detector electrodes 115A, 115B, a width of 20 nm may be assumed for each of detector electrodes 115A, 115B in FIG. 1. Electrode 115A may be shifted along the fluidic channel 105 relative to electrode 115B, by, e.g., 10 nm or 30 nm. Distances between detector electrodes from 30 nm to 100 nm or from 30 nm to 500 nm, or from 30 nm to 5 μm can be incorporated into a single device. For analytes of sufficient length, distances up to e.g., 500 μm may be used, e.g., up to 300 μm, 200 μm, or 100 μm may be used. Although electrodes with any distance therebetween may be fabricated, since DNA is difficult to obtain at a length greater than 500 μm, any electrode distance that is greater than 500 μm may be superfluous, as long as the length of the DNA does not exceed 500 μm. The smaller displacement between electrodes A and B is an example of an embodiment having overlap of the electrodes, even though they are displaced with respect to one another. In some embodiments, such as FIG. 2, there may be no overlap between detector electrodes 115A, 115B.

The voltage across detector electrodes 115A, 115B is proportional to the local impedance in the fluidic channel 105 between detector electrodes 115A, 115B. The spacing of the electrodes is determined by several factors. The smaller the distance between electrodes in a detection pair, the smaller the detector volume and, all other factors being constant, the smaller the particle that can be detected by the detection pair. However, fabrication limits may make it difficult to consistently place the electrodes in a pair at small distances. Thus, the selected distance is a trade-off between fabrication reproducibility and sensitivity of the device. The choice of separation distance and thus whether the electrodes are overlapping or non-overlapping depends on these constraints.

The resulting electrode arrangement provides a means to separate the current and voltage probes and may be used to employ 4-point sensing in a fluidic channel. In an embodiment, the electromotive electrodes 110, 110' at the ends of the fluidic channel 105 provide a current while the nanoscale detector electrodes 115A, 115B disposed across the fluidic channel 105 are used to measure voltage. The detector electrodes preferably have an output impedance higher than the impedance of the volume being measured.

The following calculations demonstrate the feasibility of this device concept. The fluidic channel 105 may be subjected to a constant electric field equal to the potential difference along the length of the channel divided by the length of the channel, i.e., 100 mV applied longitudinally to a 10 μm long fluidic channel results in a field of 100 mV/10 μm=10 mV/μm or 0.01 mV/nm. The potential difference between electrodes A and B separated by 10 nm is then the product of the distance between electrodes and the electric field or:

$$10 \text{ nm} \times 0.01 \text{ mV/nm} = 0.1 \text{ mV}.$$

Similarly, a potential difference of 0.3 mV exists between electrodes A and B when the spacing is 30 nm. Each of these potentials is readily detectable with conventional electronic measurement tools. When a DNA molecule or any other analyte 125 passes between a pair of electrodes, the impedance between the electrodes changes due to a resistivity difference between the electrolyte and the molecule. The resulting transient change in the potential is measured, while maintaining a constant current.

For the example shown in FIG. 1, assuming a constant velocity, the duration of each voltage pulse is proportional to the length of the DNA or other analyte 125 that passes between the two detector electrodes.

It is important to note that by shifting one of the transverse electrodes along the fluidic channel 105 by a distance of 10-50 nm, and using a fluidic channel 105 with a diameter of about 10 nm, the volume separating the two detector electrodes may be viewed as having a sensitivity equivalent to that of a conventional solid-state nanopore.

Figure 5:
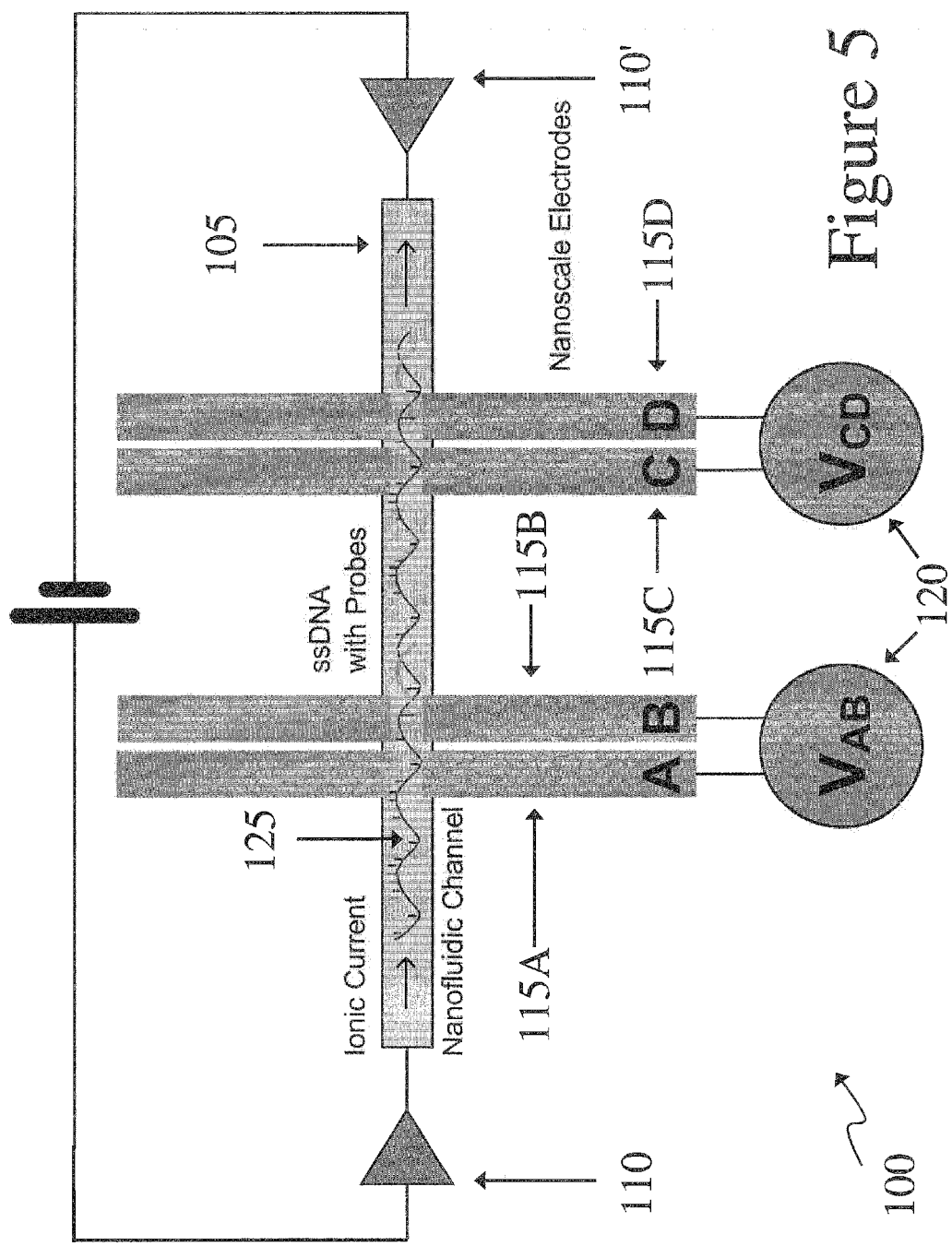
FIG. 5 is a schematic diagram illustrating a longitudinally displaced transverse electrode configuration with two pairs of electrodes disposed in a channel.

Referring to FIG. 5, multiple pairs of detector electrodes are disposed along the fluidic channel 105, with, e.g., a pair of electromotive electrodes 110, 110' with the anode 110' and cathode 110 each being disposed at one end of the fluidic channel 105, a first pair of detector electrodes 115A, 115B, e.g., 115A, 115B being disposed in the fluidic channel 105, and a second pair of detector electrodes 115C, 115D, e.g., 115C, 115D being disposed in the fluidic channel 105 distal to the first pair of electrodes in the direction of the electromotive anode 110' electrode.

In use, the voltage between a pair of electrodes, e.g., $V_{AB}$, or $V_{CD}$, may be sensed by a measurement tool 120, e.g., a voltmeter, configured to measure the potential difference between the electrode pair. In a preferred embodiment, the voltmeter may be in electrical communication with each of the electrodes in the pair via metal contact pads connected to nanowires leading to the electrodes.

Generally, an analyte 125 may be detected in the fluidic channel 105 as follows. The analyte 125 may be introduced into a fluidic channel 105. A potential is applied along the fluidic channel 105 to generate an electrophoretic force therein. For example, a potential may be applied to electromotive electrodes 110, 110' disposed at each end of the fluidic channel 105, such that an ionic current is created and the analyte 125 is translocated from a first end of the fluidic channel 105 to a second end of the fluidic channel 105. The electromotive electrodes 110, 110' may generate a constant or oscillating electrophoretic force in the fluidic channel 105 for translocation of the analyte. A voltage between a pair of detector electrodes 115A-115D disposed in the fluidic channel 105 is measured as the analyte 125 moves past each pair of detector electrodes. The voltage between the electromotive electrodes 110, 110' may be constant or it may be changed over the course of a measurement. For example, the voltage may be reduced once a DNA molecule has entered the fluidic channel 105 and before the DNA molecule has entered the volume between the detector electrodes 115A-115D, to slow the passage of the DNA molecule through the detector volume.

The analyte, e.g., the biomolecule strand and probes, are transferred from a chamber into the fluidic channel in the electrolytic solution. Typically, an electrolyte may be added to the fluidic channel by a pipette, a syringe, or a pump. An analyte sample size may be as small as practically possible, as the device allows the detection of single molecules. The fluid may wet the fluidic channels by capillary action. Analyte may be introduced into the microscale areas either with the original electrolyte or after by pumping in a new solution. An analyte, such as DNA, which may be hybridized to one or more probes, may be drawn into the fluidics channel by the potential. For small analytes, one may use diffusion, fluid flow, or a potential.

Figure 6:
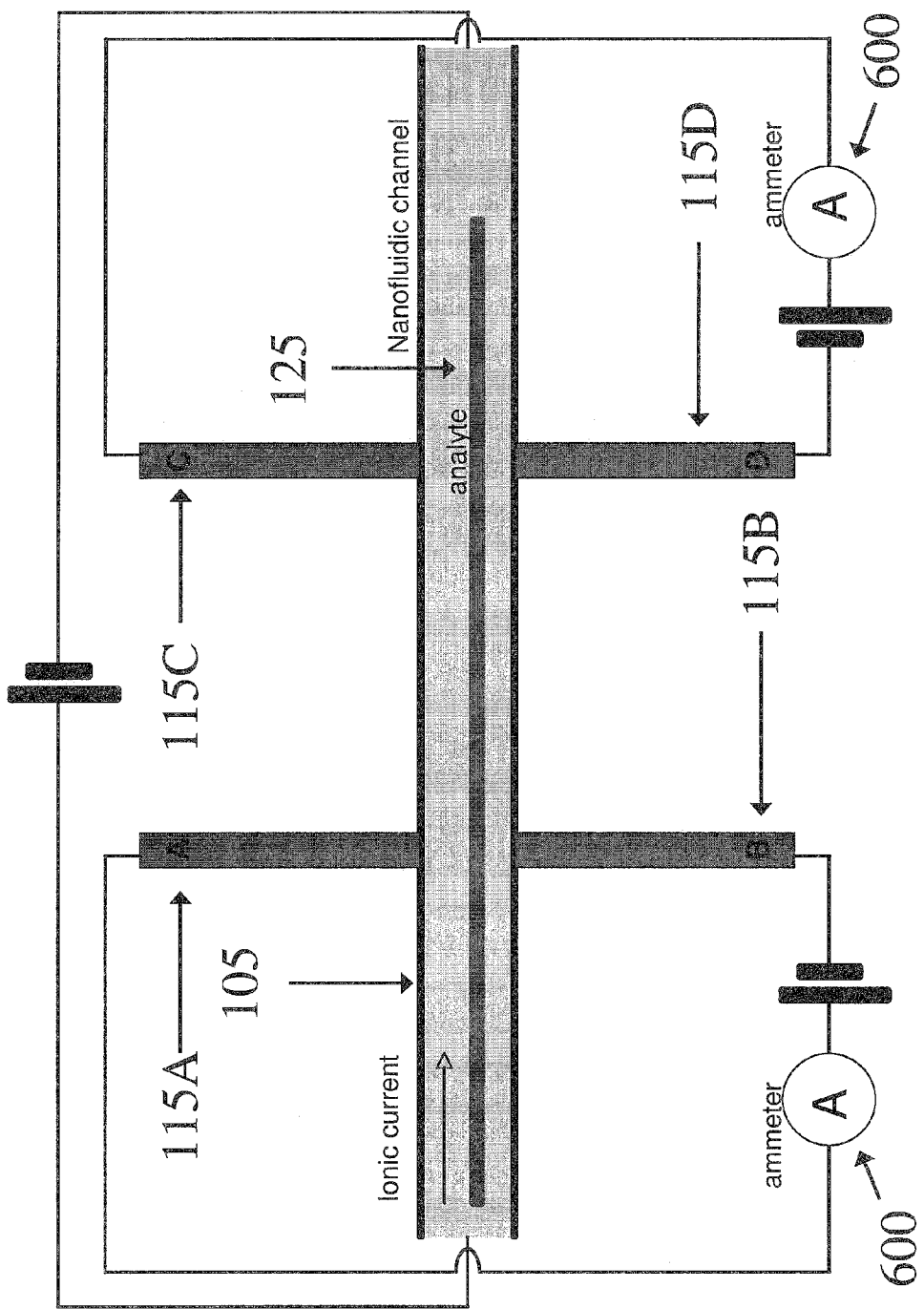
FIG. 6 is a schematic diagram illustrating a device configuration allowing the monitoring of changes in current, in accordance with an embodiment of the invention.

Referring to FIG. 6, an alternative configuration allows one to sense a current as a biomolecule passes through a fluidic channel. Two pairs of detector electrodes, e.g., 115A, 115B and 115C, 115D are disposed along the fluidic channel, with each pair of detector electrodes 115A, 115B and 115C, 115D defining a detector volume therebetween. The detector electrodes 115A-115D are connected to ammeters 600. Changes in current are measured as the analyte 125 passes through the detector volumes, allowing the length of the analyte 125 to be determined, as well as of distances between hybridized probes, analogously to the methods involving voltage changes, as described above.

Determining the Length of Biomolecules and Probe Separation Using Multiple Detector Electrode Pairs In embodiments using fluidic channels, some methods for detecting the relative position of probes hybridized to a biomolecule and/or the length of the biomolecule do not rely on the absolute time between detection events of a given electrical signal to determine a distance associated with the biomolecule (e.g., a distance corresponding to a length between probes or the length of the biomolecule itself). Instead, multiple signals are obtained (e.g., as functions of time) corresponding to a plurality of detector volumes at known locations along a fluidic channel through which the biomolecule passes, and the distances are determined by comparing the multiple signals. The positional resolution of the detector may be limited only by the physical limits of fabricating detectors that have electrodes with known positions along the fluidic channel.

When a target biomolecule, such as single-stranded DNA, is incubated with a sequence selective probe under appropriate conditions, the probe hybridizes or binds to the biomolecule at specific sites. Using the known sequence of the probes, which are complimentary to the portion of analyte to which they are bound, and the determination of the relative location of the hybridization sites allows for the construction of maps of the target biomolecule, and sequencing of the target molecule.

Nanopores may be used as detectors to determine the distance between hybridization sites as described below in and U.S. Patent Application Publication No. 2007/0190542 A1, which is incorporated herein by reference in its entirety. The construction of a fluidic channel device incorporating voltage detectors is described above. In both the nanopore and the fluidic channel (e.g., a nanochannel or microchannel), the distance between hybridization sites on the target biomolecule may be inferred from the time between the detection of a first hybridization position and a subsequent hybridization position as the biomolecule moves through the nanopore or fluidic channel.

The accurate determination of distance between hybridization positions in the previously described methods relies on a constant velocity of the biomolecule through the nanopore or fluidic channel during the measurement. The fluidic channel technology disclosed herein allows the determination of biomolecule length and distances between hybridization positions, independently of the velocity of the biomolecule.

Referring to FIG. 7a, in some embodiments, a device for determining the length of an analyte by detecting an electrical signal may include a fluidic channel 105 defined in a substrate. The substrate may be a suitable rigid material, such as silicon, silicon dioxide, fused silica, or gallium arsenide. The fluidic channel 105, e.g., a nanochannel or a microchannel, may be transversed by a plurality of detector electrodes 115A-115F disposed along a length of the fluidic channel. The relative positions of the detector electrodes 115A-115F are known. In the illustrated example, the fluidic channel 105 is transversed by six detector electrodes 115A-115F. Detector volumes 700, e.g., 700A-700E, are disposed along the fluidic channel, and may be associated with one or more detector electrodes 115A-115F; in the illustrated example, detector volumes 700A-700E are defined between the detector electrodes 115A-115F. A sensing element 701 may include two detector electrodes (an electrode pair) associated with a given detector volume, e.g., 115A, 115B and detector volume 700A. Electrical signals corresponding to the detector volumes 700 are detected by the plurality of detector electrodes 115A-115F. An analyte, e.g., a biomolecule is disposed in the fluidic channel. As the biomolecule enters each detector volume along the length of the fluidic channel, a change in the electrical signal is recorded. The length of the biomolecule may be determined from the number of detector volumes that show coincident signals.

The detector electrodes 115A-115F may be configured for connection to a measurement tool for capturing the electrical signals corresponding to the detector volumes. The measurement tool may be, for example, a voltmeter, an ammeter, or a field-effect transistor. The captured electrical signals indicate the length of the analyte. Electrical signals captured by the measurement tool may be recorded as a function of time by a data collection device 702, e.g., a Stanford Research Instruments SIM970 voltmeter. An analyzing module 705, such as a computer, e.g., an apparatus including a memory that stores code defining a set of instructions and a processor that executes the instructions thereby to determine the length of the analyte from two or more detected electrical signals, may be in electrical communication with the data collection device, programmed to determine which detector volumes record a change in electrical signal at the same time. In some embodiments, an electronic circuit may be configured to output a signal only when two electrical signals corresponding to two detector volumes change at the same time.

As discussed with reference to FIG. 1, a pair of electromotive electrodes (110, 100') may be disposed at a first and a second end of a fluidic channel. The pair of electromotive electrodes may include macroscopic electrodes arranged to generate a constant, changing, or oscillating electrophoretic force in the fluidic channel for translocation of the analyte disposed within the fluidic channel.

One or more of the detector electrodes 115A-115F may be formed from a conductive material, such as platinum, gold, chrome, titanium, silver chloride, silver and/or graphene. As described above with reference to FIGS. 1-6, the detector electrodes 115A-115F may have various configurations. For example, a sensing element corresponding to a given detector volume may include two detector electrodes 115A, 115B (an electrode pair) disposed on opposing sides of the fluidic channel 105 (FIGS. 1 and 2). In another embodiment, the sensing element may include two detector electrodes 115A, 115B disposed on the same side of the fluidic channel 105 (FIG. 4). In yet another embodiment, the sensing element may include a first detector electrode 115A transversing the fluidic channel 105 and a second detector electrode 115B transversing the fluidic channel 105 (FIG. 3).

The fluidic channel may have a width that is not smaller than approximately the same size as the analyte, and may be sufficiently large such that large molecules bound to the analyte may pass through the fluidic channel. For example the width and depth of the fluidic channel may be selected from the ranges described previously. The fluidic channel may be sufficiently deep to allow large molecules bound to the analyte to pass through and yet shallow enough to be approximately the same size as the analyte. As also described previously, the length of the fluidic channel may be selected such that the entire analyte is contained in the fluidic channel.

The size of the channel containing multiple detector volumes may be chosen with regard to the persistence length of the analyte. For example, a randomly coiled polymer (e.g., DNA) may be elongated when introduced into a confined space, such that when the confinement space becomes smaller the extent of elongation becomes greater. In some embodiments, it may be preferable to elongate the analyte to measure length or distance between probes. Depending on the cross-sectional size and the persistence length it may be useful to have the geometric mean of the width and depth of the channel be between 5% and 500% of the persistence length of the analyte.

While not wishing to be bound by theory, an analyte may be pulled into the fluidic channel (e.g., by electromotive force), and then extended (e.g., linearized) as the electromotive or other force pulls the analyte into the fluidic channel. This effect may be counterbalanced by the mass of the analyte outside of the fluidic channel as the analyte is being unwound. In some embodiments, the structure of the fluidic channel may facilitate entry of the analyte into the channel, e.g., the fluidic channel may include a series of posts (e.g., U.S. Pat. No. 7,217,562, which is incorporated by reference in its entirety) and/or a funnel shape.

In an embodiment, a fluidic channel detector may be preferably arranged such that the entire analyte enters the fluidic channel before it enters the first detector volume. This configuration provides the advantage of reducing the effect of the analyte on the conductance of the fluidic channel. For instance, if one is beginning to measure the change in potential of a detector volume while the conductance of the whole fluidic channel is changing due to more analyte entering the fluidic channel, the analysis becomes more complicated. Similarly, preferably, the analyte is contained completely in the fluidic channel when it exits the last detector volume. Thus, the length of the fluidic channel preferably has a minimum length that is approximately three times the length of the analyte (assuming that the detector volume is only as long as the analyte, which is a minimal requirement but not optimal). The length of a 1 kb segment of DNA is about 330 nm, so a length of the fluidic channel is preferably at least 1 μm in length. In one embodiment, the longest segment of DNA suitable for analysis with the described methods may be 10 megabases (Mb), which corresponds to a preferred fluidic channel of at least 10 mm. More preferably, the length of a fluidic channel is ten times the length of the analyte, and thus a more preferred upper limit for a fluidic channel length is 100 mm (10 cm). Thus, the fluidic channel length is preferably selected from a range from 1 μm to 10 cm. Longer and shorter fluidic channel lengths are also possible.

A plurality of fluidic channels may be defined in the substrate, allowing parallel or sequential analysis of various analytes. A voltage amplifier may be incorporated into the device, configured to amplify two or more electrical signals.

Figure 7B:
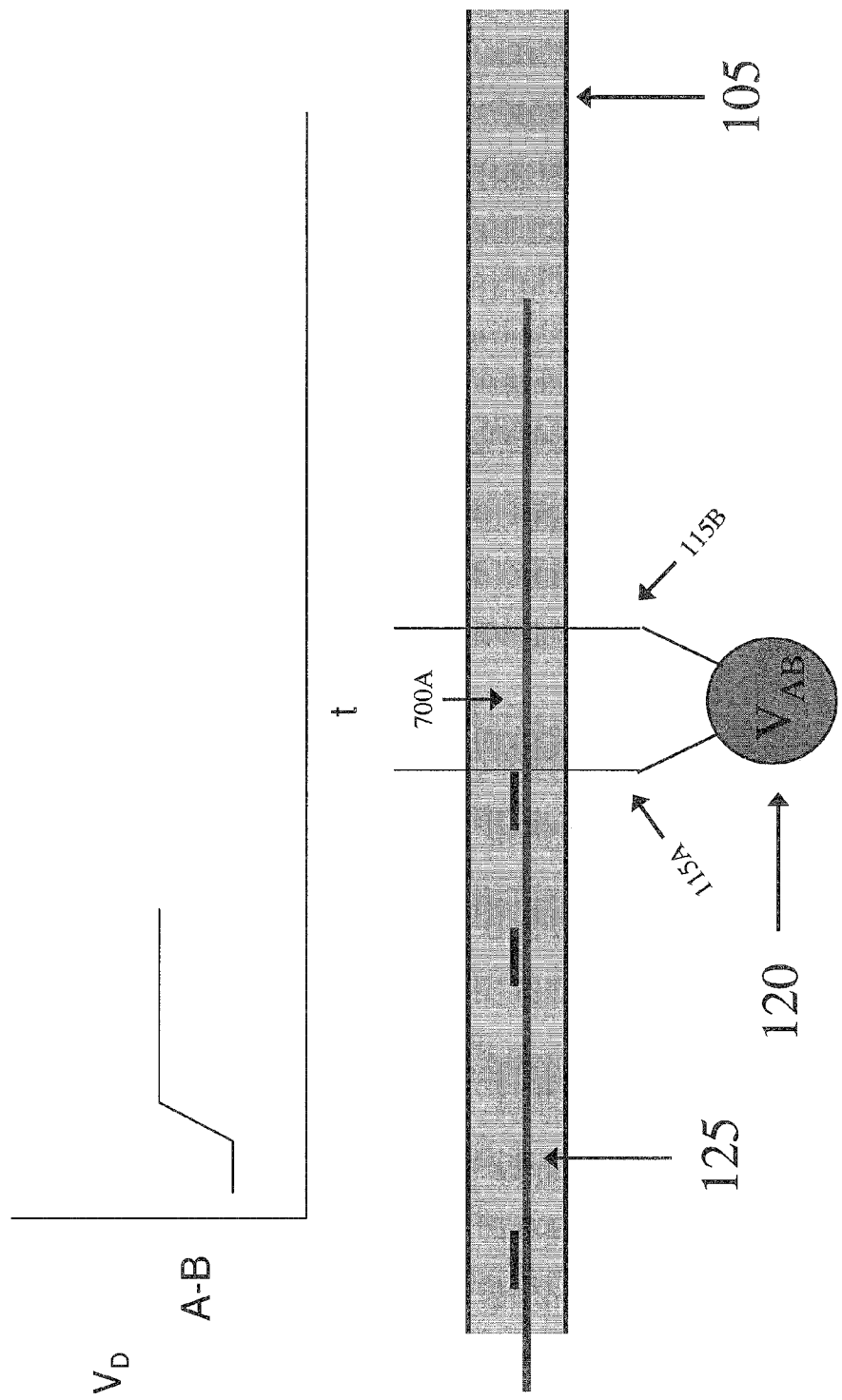
FIG. 7b is a graph illustrating an electrical signal recorded as the biomolecule enters a detector volume.

Referring to FIG. 7*b*, the electrical signal increases linearly as the analyte 125 enters the detector volume 700A. When the detector volume is completely filled, the signal stays essentially constant. The electrical signal may have fluctuations from noise and from the fact that a long analyte 125 such as DNA typically has small bends in it. When a section having a bend enters the detector volume, the electrical signal may increase slightly, and then may decrease slightly when the bend exits the detector volume. Calibration of the electrical signals, therefore, may be needed to determine length. If one measures just the distance between the ends of the analyte 125, one may not determine the actual length of the analyte 125 because of small kinks and bends. By calibrating the electrical signal by measuring the electrical signal generated by an analyte 125 of a known length, one may determine the actual length between ends.

The length of an analyte may be determined in two ways. In a first method, the length is determined by the distance between two detector electrodes that detect the analyte at the same time. Detector electrodes that are displaced with respect to one another by a distance that is less than the length of the analyte detect the analyte at the same time. Detector electrodes that are positioned farther apart than the length of the analyte do not detect the analyte at the same time. Any of the detector electrode configurations described herein may be used in this implementation. Detector electrodes displaced along a length of a fluidic channel, as well as detector electrodes disposed opposite each other in a fluidic channel may both be used.

In an embodiment, detector electrodes 115A, 115B, 115C, 115D, 115E, 115F (not shown) may be respectively disposed sequentially along a length of a fluidic channel 105, defining three detector volumes 700A, 700C, 700E between detector electrodes 115A and 115B, 115C and 115D, and 115E and 115F, i.e., between three sets of electrode pairs. If the analyte 125 fills—is detected in—two detector volumes (e.g., between detector electrodes 115A and 115B and detector electrodes 115C and 115D) at the same time, the analyte 125 is as long or longer than the distance between the two outer detector electrodes 115A, 115D disposed at the outer bounds of the two detector volumes. If the analyte 125 is not detected at the same time in a third detector volume 700E, bound by detector electrodes 115E, 115F, separated by a greater distance from detector electrodes 115A, 115B than detector electrodes 115C, 115D, then the analyte 125 is shorter than the distance between detector electrodes 115B and 115E. Thus, the length of the analyte 125 is longer than the distance between detector electrodes 115A and 115B and shorter than the distance between detector electrodes 115B and 115E. The difference between the distance 115A-115D and 115B-115E may define the resolution of the system, i.e., how accurately one can determine the length of the analyte 125.

Referring again to FIG. 7a, the resolution may be improved by also utilizing the time domain. That is, if the analyte 125 is detected at the same time in detector volumes 700B, 700C between detector electrodes 115B-115C and detector electrodes 115C-115D, but the analyte 125 is not detected in a detector volume 700D between detector electrodes 115D-115E, one may measure the time between the loss of signal in detector volume 700B and the acquisition of signal in detector volume 700D. If the speed of the analyte 125 in the fluidic channel 105 is determined, then the measured time may be used to calculate the distance the analyte 125 moved (velocity×time=distance) before it reached detector volume 700D between detector electrodes 115D, 115E and thus how much shorter the analyte 125 is than the distance between detector electrodes 115B and 115D.

The second method is preferably used with detector volumes defined by displaced electrodes, as it relies on using the distance between electrodes rather than a distance between detector volumes. A detector volume defined by detector electrodes separated by a distance that is less than the length of the analyte is completely filled by the analyte as the analyte moves through the fluidic channel, and provide an electrical signal that is the maximum for that detector volume/analyte combination. Thus, if two detector electrodes 115A, 115B (an electrode pair) are separated by a known distance and the analyte completely fills the detector volume therebetween, then the analyte is at least as long as the separation between the two detector electrodes. A detector volume bound by detector electrodes 115C, 115D (an electrode pair) that are separated by a distance greater than the length of the analyte provides an electrical signal that is less than maximal. The ratio of the electrical signal (e.g., observed voltage change) to the maximum expected signal (e.g., maximum expected voltage change) of a detector volume is equal to the ratio of the analyte length to the distance between detector electrodes bounding the detector volume:

$$l = d \times (\Delta V_{obs}/\Delta V_{max})$$

where the l is the analyte length, d is the distance between the sensing electrode, $\Delta V_{max}$ is the maximum expected voltage change of a detector volume, and $\Delta V_{obs}$ is the observed voltage change. This method can be used to determine the length of the biomolecule when the biomolecule is less than the distance between detector electrodes. It may also be used to increase the resolution of the determination of the biomolecule length when the biomolecule does not fit perfectly between detector electrodes.

Calibration to determine the maximal electrical signal may be performed with a similar analyte that is longer than the distance between detector electrodes being calibrated. A calibration factor may be calculated from the maximal signal obtained in other similar detector volumes that may have different separations between detector electrodes, or it may be calculated theoretically from the known behavior of the analyte in the test set up and the known distance between the detector electrodes. For example, if the electrical signal used is a voltage signal reflecting a potential drop across displaced detector electrodes, the percent change in voltage signal in any detector volume for a maximal signal for a species of analyte is a constant. That is, if the voltage signal between detector electrodes 115A, 115B changes by a maximum of 10% when a piece of double-stranded DNA that is much longer than the distance between detector electrodes 115A, 115B goes through the detector volume, then the maximum change in potential in any other detector volume in the same fluidic channel, in which the channel width and depth remain essentially constant, may also be 10%.

In some embodiments, the detector electrodes have thicknesses ranging from 5 nm to 100 nm at the point where the detector electrodes intersect the fluidic channels. The detector electrodes may be wider and/or thicker in regions distal to the fluidic channels and approaching contact pads disposed at the perimeter of the device. As an example, a width of 20 nm may be assumed for each of the detector electrodes. The detector electrodes may be disposed along the fluidic channel at regular intervals with respect to one another, by, e.g., 10 nm or 30 nm.

In particular, in an embodiment, a device utilizes multiple pairs of nanoscale detector electrodes for electrical sensing of biomolecules and other nanoscale analytes in fluidic channels. The analytes may include a biopolymer such as deoxyribonucleic acids, ribonucleic acids, and polypeptides. The biopolymer may be a single-stranded molecule. Portions of the analyte sequence may be at least partially hybridized with a probe, and the detected electrical signals may indicate the presence of a probe bound to the analyte. The detector electrodes disposed along the fluidic channel may be used to determine the length of the analyte. In use, the analyte may be disposed in the fluidic channel. A potential may be applied along the fluidic channel to generate an electrophoretic force therein, such that the analyte is translocated from one end of the fluidic channel to another end of the fluidic channel. As the analyte moves down the fluidic channel, it enters the detector volume disposed along the fluidic channel. The analyte may occupy more than one detector volume at the same time. Each occupied detector volume emits an electrical signal that indicates the presence of the analyte in the detector volume. The electrical signal may be a voltage signal, a current signal, or another electrical signal. As the analyte moves through the fluidic channel, the detector electrodes may detect two or more electrical signals corresponding to two or more detector volumes.

The electrical signal(s) may be recorded, e.g., by a measurement tool in electrical communication with the detector electrodes. The length of the analyte may be determined by analyzing the detected electrical signals. For instance, one may identify at least two detector volumes in which the analyte is sensed at a given time, and then determine a distance between detector electrodes corresponding to the at least two detector volumes. Thus, the furthest spaced detector volumes that have coincident signals may provide a lower bound for the length of the analyte in the fluidic channel while the closest spaced detector volumes that simultaneously lack a signal may provide an upper bound for the length of the analyte in the fluidic channel. The distance between the outer ends of the furthest spaced detector volumes that have coincident signals provides an upper bound on the length of the analyte in the fluidic channel. The distance between the inner ends of the furthest spaced detector volumes that have a coincident signal provides a lower bound on the length of the analyte in the fluidic channel. The error in the determination of the length of the analyte depends on the accuracy to which the distances between detector electrodes is known.

A correction factor may be applied to the measured length to determine the actual length of the analyte. For instance, it is known that a polymer that is confined to nanoscale channels stretches to a varying percentage of its full length depending on the size of the fluidic channel and the persistence length of the polymer under the conditions of the experiment (Tegenfeldt, J. O et al. *Proc. Nat. Acad. Sci.* 2004, 101, 10979) which is incorporated herein by reference in its entirety. Analytes that are longer than their persistence length (i.e., longer than the maximum length of the uninterrupted polymer chain persisting in a particular direction) tend to form random coils or balled-up structures in solution. When a biomolecule is confined to a fluidic channel, it may be forced to extend and become more linear. However, depending on the size of the fluidic channel and the persistence length of the biomolecule, it may not be straightened out to its full length. Thus, any measurement of the length of the biomolecule in a fluidic channel is preferably corrected either by using a calibration standard in the same detector volume or by applying a correction factor based on the behavior of the biomolecule in the fluidic channel.

Figure 7C:
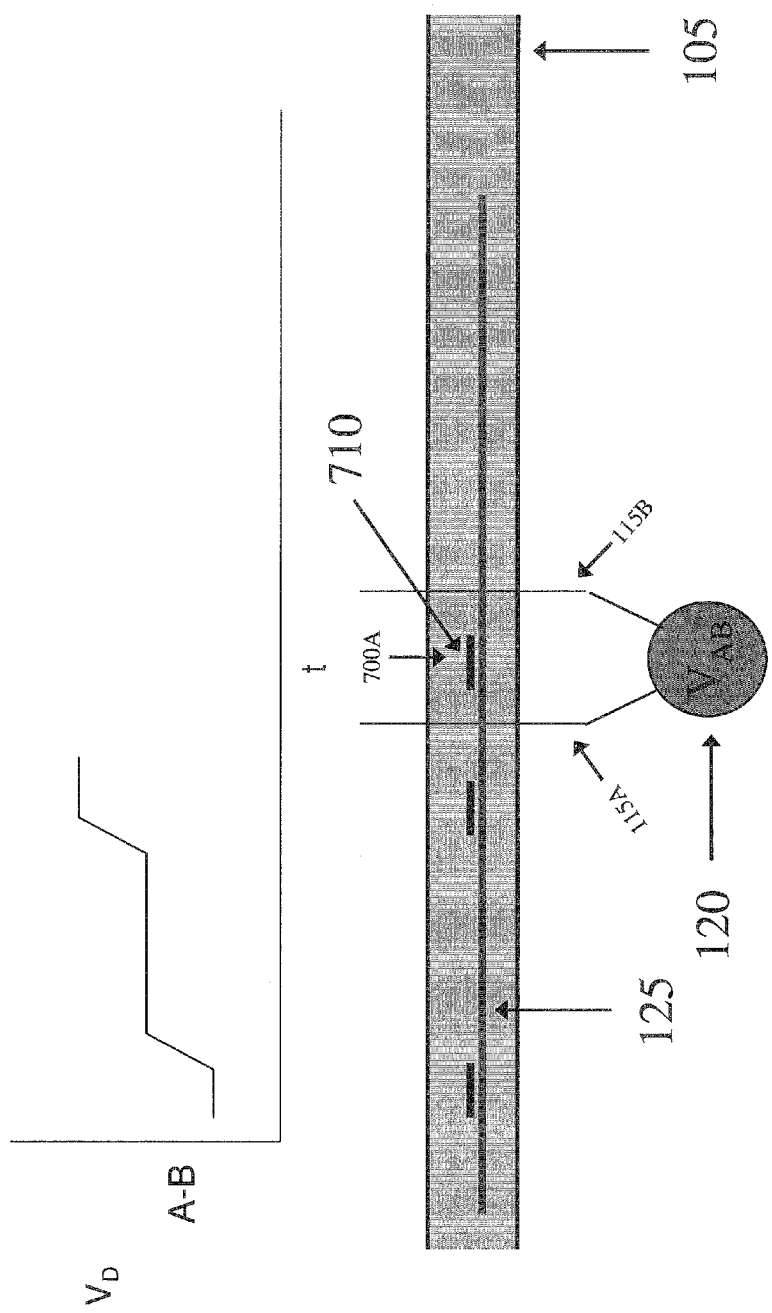
FIG. 7c is a graph illustrating the slope of the electrical signal that reflects first the entry of a biomolecule into a detector volume, and then the entry of a hybridized probe into the same detector volume.

In another embodiment, multiple detector electrodes may be used to determine the distance between labeled positions on a biomolecule analyte by observing electrical signals indicating labels that are coincident in two or more sensing elements. The biomolecule analyte may be DNA or RNA, and the DNA or RNA may be single-stranded or double-stranded. The label may be a protein that is bound to the biomolecule or it may be an oligonucleotide that is hybridized to the biomolecule. The label may also be any molecule that binds to the biomolecule. The binding may be sequence dependent, or it may be conformation dependent. FIG. 7c illustrates the slope of the electrical signal that reflects first the entry of the biomolecule into a detector volume 700A, and then the entry of a hybridized probe 710 into the same detector volume 700A.

The distance between detector electrodes allows one to determine the distance between the labeled positions. The determination of the distance between labeled positions relies on knowledge of the distance between the detector electrodes and does not require that the biomolecule move with constant velocity through the device. The spacing between detector electrodes may be chosen to vary in a fashion that enables the determination of a variety of distances. The distances between hybridization events may be used to map, haplotype, or sequence biomolecules such as DNA or RNA.

Figure 8B:
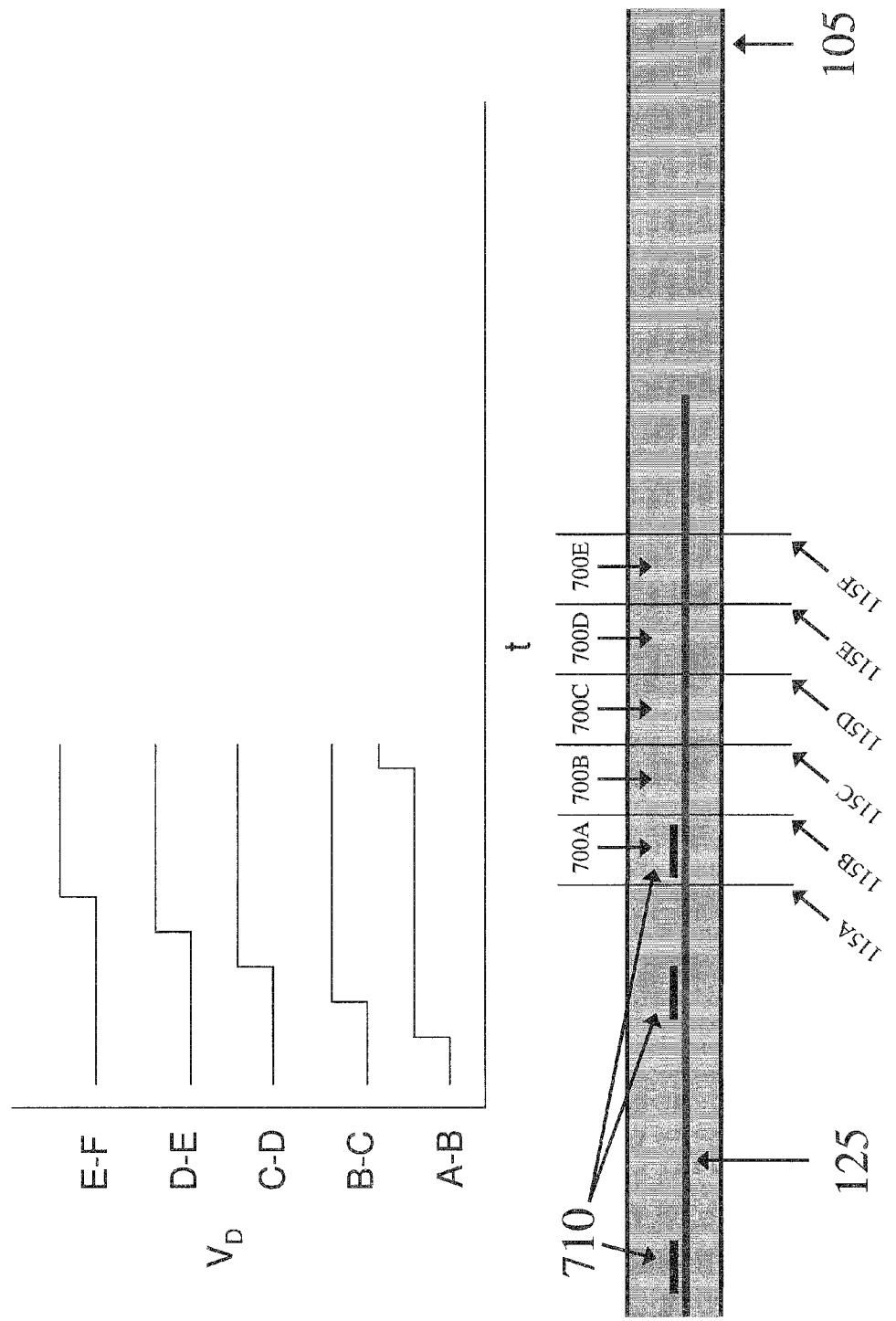
Figure 8D:
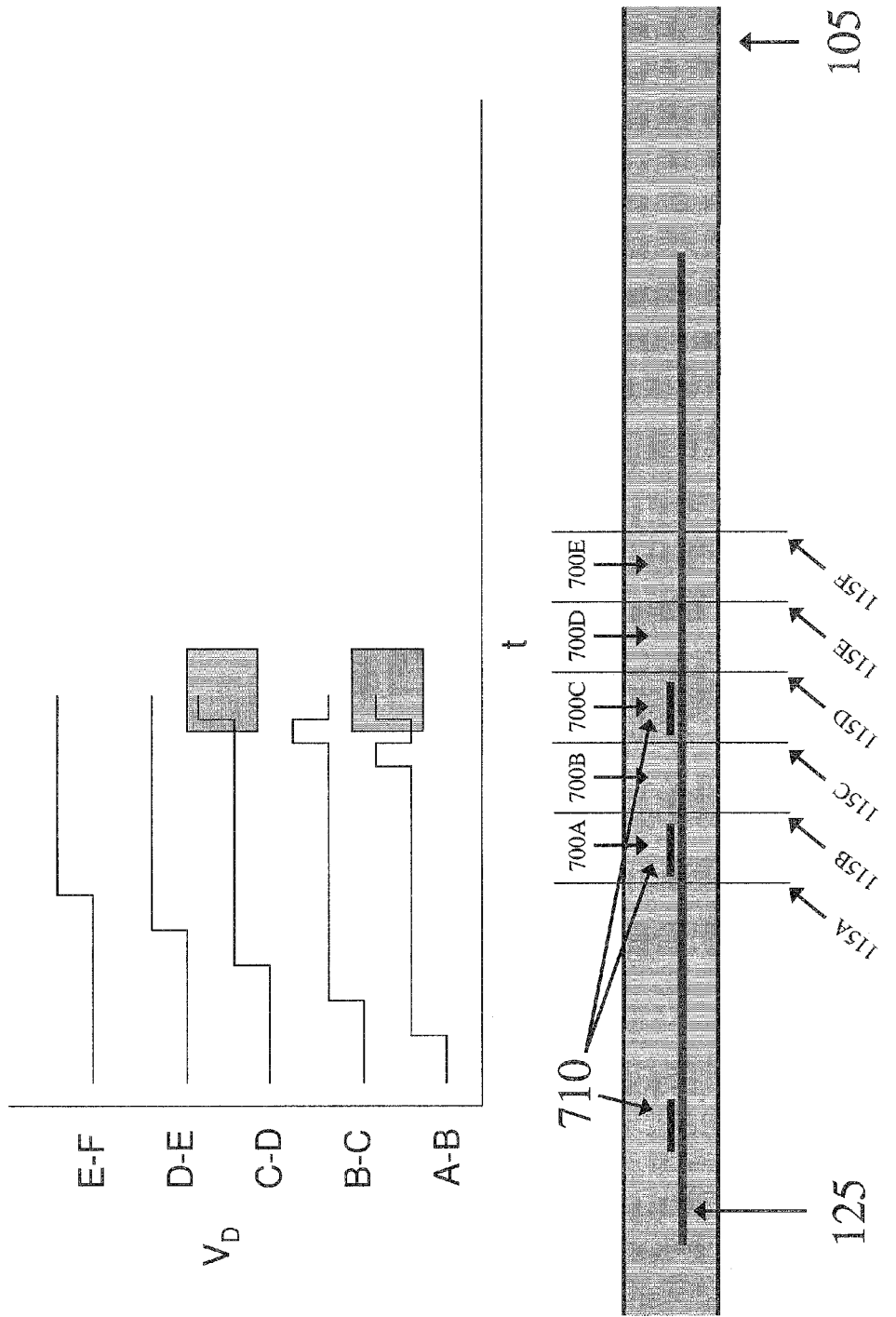

The determination of distances between hybridization events is illustrated in FIGS. 8a-i, where a fluidic channel 105 is transversed by six detector electrodes 115A-115F, (e.g., a distance-based detector). FIGS. 8a-8i illustrate the progression of a hybridized biomolecule through a fluidic channel, and the resulting electrical signals. A biomolecule 125 with hybridized probes 710 is disposed in the fluidic channel. In FIG. 8d, two sensing elements (each including two detector electrodes 115 and the detector volume 700 therebetween) indicate the presence of hybridized probes 710 at the same time. A distance between probes 710 may then be determined by using a response of electrical signals corresponding to two or more detector volumes. Correlation of signals from different detector volumes gives the distance between probes. The spacing between detector electrodes 115A-115F may be used to determine a maximum distance or a minimum distance between probes 710. In the illustrated embodiments, the distance between these probes 710 is less than the distance between detector electrodes 115A, 115C and greater than the distance between detector electrodes 115B, 115C.

The calculation of distances between probes 710 may be used to determine a map or sequence of a biomolecule as follows. An analyte 125 may be prepared by hybridizing a first plurality of probes 710 with the biomolecule such that the first plurality of probes 710 attaches to portions of the biomolecule to produce a partially hybridized biomolecule. A plurality of probes 710 may be made up of multiple copies of the same probe 710 with the same sequence selectivity (in the case of a map determination) or may be made up of two or more probes 710 with different sequence selectivity (in the case of a sequence determination). A partially hybridized biomolecule is created when the entire length of a sequence selective probe 710 binds to a portion of the length of the target biomolecule. The probes 710, i.e., hybridizing oligonucleotides, may each have the same composition, or may have different compositions. Further details regarding hybridization are given below.

It should be understood that, while the ultimate goal of embodiments of the present invention is to provide for the sequencing of biomolecules, the generation of maps offers significant utility as well. Data developed using the methods and apparatus herein for map determination may be combined with short-read data from this or other methods and apparatus to develop sequence information for target biomolecules. Short read sequence data conventionally refers to DNA sequences, obtained from a DNA sequencing instrument, that have a contiguous length that is shorter than those obtained from the sequence reads obtained by Sanger sequencing during completion of the Human Genome project. Thus, short read sequence data typically refers to sequencing reads that are shorter than 1000 base pairs. Short read sequence data may also refer to sequencing reads that are shorter than 400 base pairs.

As will be described in greater detail below, for sequence determination applications, probes with different sequence selectivity may be used together in a single run, or separately in several runs. It is preferred that when using probes of different sequence selectivity, probes are selected such that at least a portion of one probe set shares sequence selectivity with a subregion of the analyte to which a different probe set is selective, to thereby produce overlapping probe data sets. While the methods described below relate generally to the use of fluidic channels, it should be understood that similar techniques using nanopore systems are envisioned as well.

As illustrated in FIGS. 8a-8i, the analyte 125 may be disposed in a fluidic channel 105, e.g., a nanochannel or a microchannel. A potential may be applied along the fluidic channel 105 to generate an electrophoretic force therein such that the analyte 125 is translocated from a first end of the fluidic channel 105 to a second end of the fluidic channel. Two or more electrical signals may be detected as the analyte 125 moves through the fluidic channel. The detected electrical signals, corresponding to two or more detector volumes of the fluidic channel, may be detected by using a plurality of detector electrodes 115A-115F disposed along the length of the fluidic channel. The detected electrical signals may indicate the locations of the hybridized probes 710 along the biomolecule. The electrical signals may be analyzed to determine in which detector volumes probes 710 bound to the biomolecule are located. This analysis may be done either visually or with the assistance of a computer program that executes the analysis described herein. At least a portion of the sequence of the biomolecule may be determined by using a distance between the detector electrodes 115A-115F corresponding to the detector volumes in which the probes 710 are located and the known recognition site sequence of the probe 710. At each point where the probe has bound, the sequence may be known because it is complementary to the bound probe. The combination of the known recognition site sequence and its distance from the end of the biomolecule allow the determination of the biomolecule sequence. A computer algorithm may be used to process the two or more electrical signals to help determine the sequence of the biomolecule.

Additional details regarding the sequencing of a biomolecule based on positional information obtained by use of nanopores are provided below in the section *Sequencing by Using Probes* (fluidic channels are elongated nanopores) as well as in U.S. Patent Publication No. 2007/0190542 A1, which is incorporated herein by reference in its entirety. Further details regarding reconstructing positional data are disclosed in U.S. Publication No. 2009/0099786 which is incorporated herein by reference in its entirety; the publication discusses positional data within the context of sequencing of primarily double-stranded DNA, but the principles are applicable to the sequencing of single-stranded DNA.

As shown in FIG. 7c, the electrical signal may initially change when the biomolecule moves through a detector volume 700A associated with two detector electrodes 115A, 115B and further change when a portion of the biomolecule including a hybridized probe 710 moves through the detector volume 700A.

In some embodiments, a second plurality of probes may be hybridized with the biomolecule, and the detecting, analyzing, and determining steps may be repeated with the second plurality of probes. This subsequent hybridization may occur with the same biomolecule sample that was exposed to the first plurality of probes, or it may occur using a naïve, previously unhybridized sample.

The electrical signals may be used to detect and record complexed and uncomplexed regions of the biomolecule to create a first probe data set, i.e., probe map, of the first plurality of probes and a second probe map of the second plurality of probes, the first probe map and the second probe map each respectively including information about the relative positions of the hybridized first and second plurality of probes. Each probe map may include a series of numbers that indicate the distances between probes. The numbers may indicate distance in terms of base pairs or distance in terms of nanometers. A candidate sequence for at least a portion of the biomolecule may be determined by ordering at least two probe sequences using positional information and/or a combination of overlapping probe binding sequences and positional information.

The biomolecule may be a single-stranded or a double-stranded target biomolecule.

The first and second probe maps may include information about an error of the positional information for each probe. For example, each indicated distance may have an associated standard deviation, e.g., 100 nm±10 nm. Further, a candidate sequence may be determined by ordering at least two probe sequences using at least one of (i) positional information and parameters relating to the error in positional information or (ii) a combination of overlapping sequences of the probe molecules and positional information and error in positional information.

As will be described in greater detail below, the analyte may be prepared by contacting the biomolecule, i.e., the target molecule, with a first probe having a first probe specificity for recognition sites of the target molecule to form a first plurality of local binary complexes (in the case of a single-stranded target molecule) or ternary complexes (in the case of a double-stranded target molecule), the first probe having a first known recognition site sequence. The electrical signal may be used to determine positional information of the first plurality of local binary or ternary complexes.

The biomolecule may also be contacted with a second probe, either subsequently or in parallel to the first probe, having a second probe specificity for recognition sites of the target molecule to form a second plurality of local binary or ternary complexes. The second probe may have a second known recognition site sequence. Positional information of at least the first and second plurality of local binary or ternary complexes may be aligned to determine a sequence of the biomolecule. As noted, it is preferred, but not required that the first and second recognition site sequences have subregions that overlap.

Figure 9A:
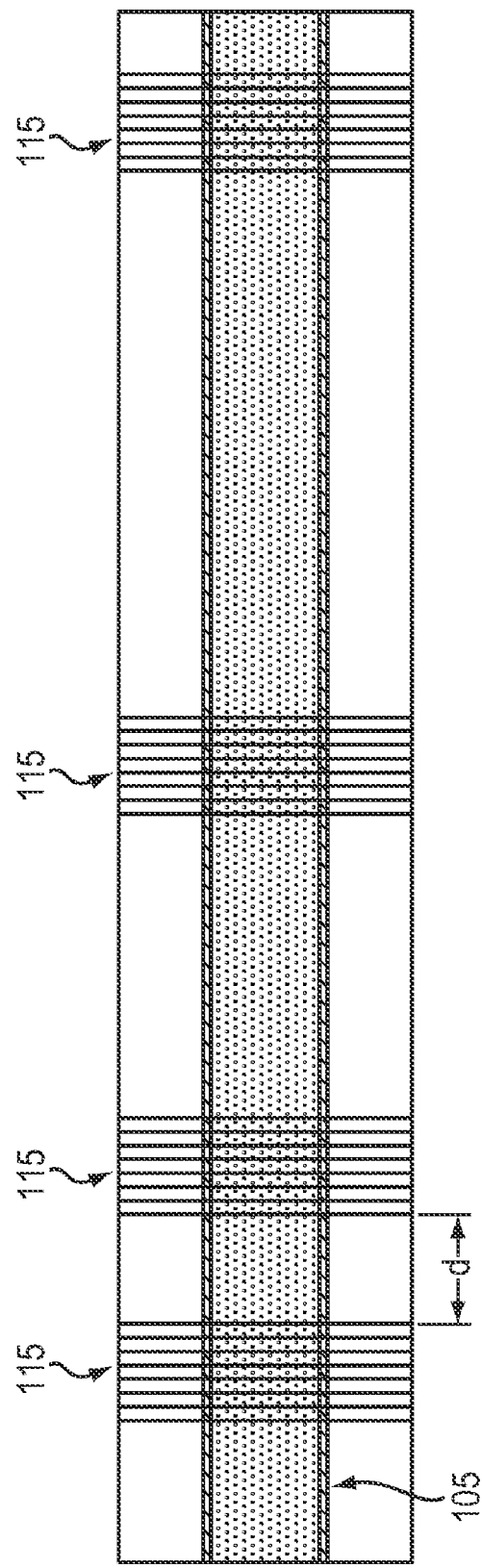
FIG. 9a is a schematic diagram illustrating a fluidic channel transversed by numerous perpendicular detector electrodes.
Figure 9B:
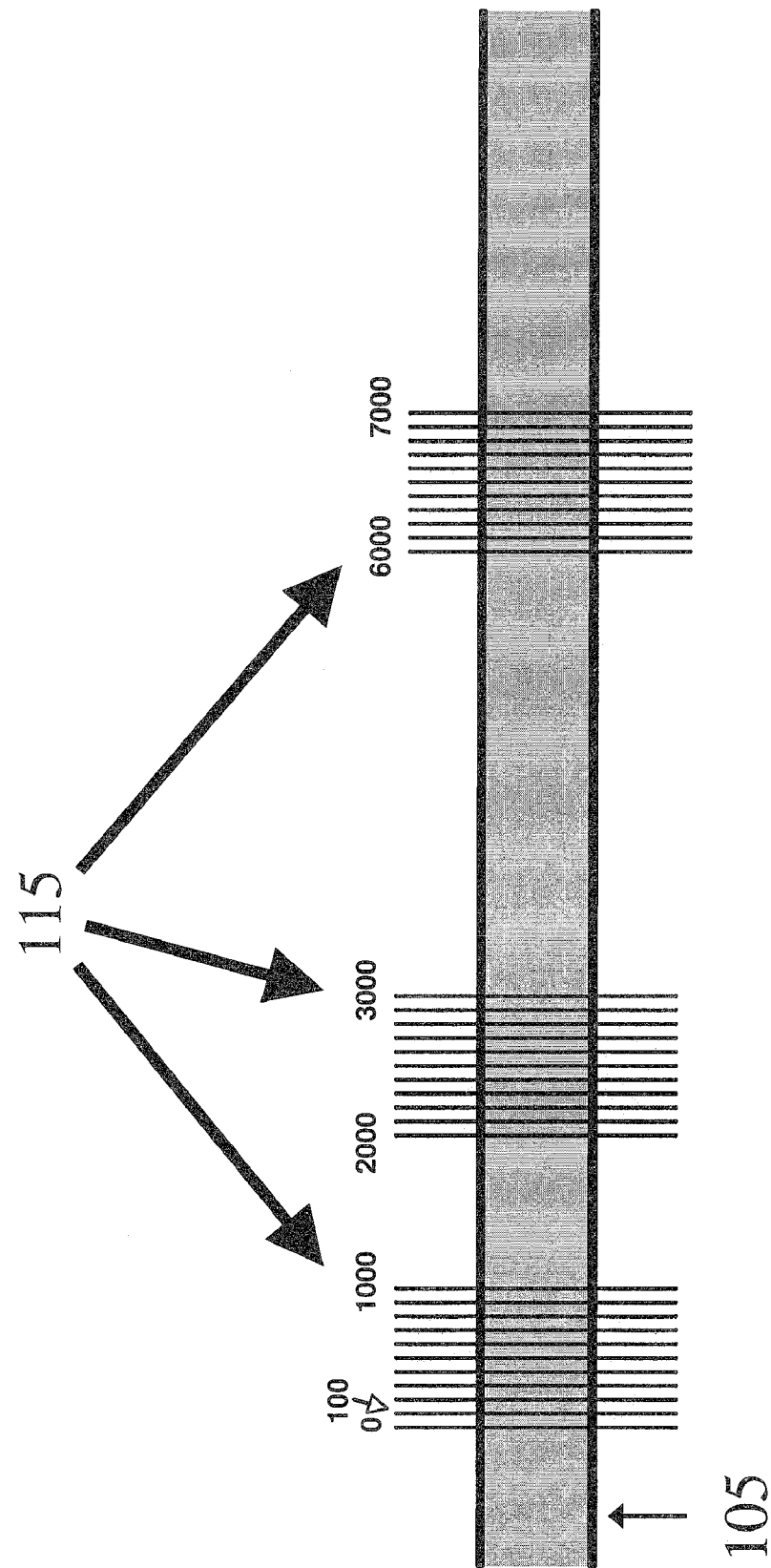
FIG. 9b is a schematic diagram illustrating an arrangement of detector electrodes that allows for measurement of small lengths (increments of 100) over total lengths of 7000.

Referring to FIGS. 9a and 9b, a fluidic channel 105 is transversed by numerous perpendicular detector electrodes 115. The detector electrodes 115 may be grouped into clusters of finely spaced electrodes, with greater separation between clusters. Finely spaced electrodes give distance information over short distances. Electrodes spaced further apart provide correlation signals over longer distances. In an embodiment, the detector electrodes 115 may include a first plurality of n electrodes each laterally offset by a first predetermined distance along the fluidic channel, i.e., the nanochannel or microchannel, to thereby define n−1 detector volumes. A second plurality of m electrodes may each laterally offset by a second predetermined distance along the nanochannel or microchannel, to thereby define m−1 detector volumes. The second plurality of electrodes may be laterally offset along the nanochannel or microchannel by a distance d (see FIG. 9a) that is greater than either of the first or second predetermined distances. In particular, the distance d is the distance between the two closest electrodes from the first and second pluralities of electrodes.

The detector electrode 115 arrangement of FIG. 9b allows the measurement of biomolecule lengths with an accuracy of about 100 bp. Larger spacing of the detector electrodes 115 allows longer lengths to be measured. By combining regions of short spacing with regions of long spacing, measurement of long lengths with high resolution may be obtained. As illustrated, in an embodiment, detector electrodes 115 are arranged to allow for accurate measurement of longer lengths in small length increments. That is, the detector electrode 115 spacing enables high resolution even for longer lengths. For instance, if the analyte is DNA, the small increments may have detector electrode 115 separations of about 100 bases, and the groups of tightly spaced detector electrodes 115 may be separated by 1000 bases to 10,000 bases or more.

Detector electrode spacing may be optimized with respect to the number of different length measurements that may be made with a defined number of detector volumes or a defined number of detector electrodes. The spacing between each detector volume may be predetermined and unequal. The spacing may be based on a Golomb ruler. Referring to FIG. 9c, a Golomb ruler (e.g., of length 6 as shown in FIG. 9c) in this context would define a set of integer distances between detector electrodes such that no two distances are the same. For instance, detector electrodes at positions 0, X, 4X, 6X would allow detection of lengths of X, 2X, 3X, 4X, 5X, and 6X.

A Golomb ruler may also be used to set the spacing between detector electrodes for each detector volume. Thus, the spacing between the detector electrodes defining the first detector volume may have a distance X. The next detector electrode may be placed at a distance of 3X from the second detector electrode. The next detector electrode may be placed at a distance 2X from the third electrode. Detector volumes having lengths X, 2X, 3X, 4X, 5X, and 6X may then be obtained from 4 electrodes.

Golomb rulers may serve as a starting point from which other electrodes may be inserted in order to sample all lengths or have all detector volumes represented. As a result, one or more of the lengths or spacings may be repeated. For instance, the Golomb ruler: 0, 3X, 4X, 9X, 11X can measure lengths X, 2X, 3X, 4X, 5X, 6X, 7X, 8X, 9X, 11X. The distance 10X is missing. By modifying the ruler to be 0, 3X, 4X, 9X, 10X, 11X the possible measured lengths are X, X, X, 2X, 3X, 4X, 5X, 6X, 6X, 7X, 7X, 8X, 9X, 10X, 11X. Thus, the X, 6X, and 7X spacings have more than a single occurrence. However, six pairs of detector electrodes are capable of measuring 11 integer increments of distance.

Other spacings, integral or non-integral, may be envisioned by one of skill in the art.

Referring to FIG. 10, in an alternative arrangement, detector electrodes 115A-115F transverse a fluidic channel 105 with varying distances between detector electrodes 115A-115F. The distances between detector electrodes 115A-115F may be selected in accordance with the principles discussed with reference to FIGS. 9a-9c. As illustrated, the device may include at least three pairs of detector electrodes 115A, 115B; 115C, 115D; 115E, 115F. A distance between detector volumes 700A, 700C defined by a first and second pair of detector electrodes 115A, 115B; 115C, 115D may be equal to a distance between detector electrodes 115B, 115C, and a distance between detector volumes 700C, 700E defined by the second and third pair of detector electrodes 115C, 115D; 115E, 115F may be equal to a distance between detector electrodes 115D, 115E. Thus, the distance between detector volumes 700A, 700C defined by the first and second pairs of detector electrodes 115A, 115B; 115C, 115D may be unequal to a distance between detector volumes 700C, 700E defined by the second and third pairs of detector electrodes 115C, 115D; 115E, 115F. In some embodiments, the detector volume 700A defined by the first pair of detector electrodes 115A, 115B is unequal to a detector volume 700C defined by a second pair of detector electrodes 115C, 115D, and a detector volume 700C defined by the second pair of detector electrodes 115C, 115D is unequal to a detector volume 700E defined by a third pair of detector electrodes 115E, 115F.

Figure 11B:
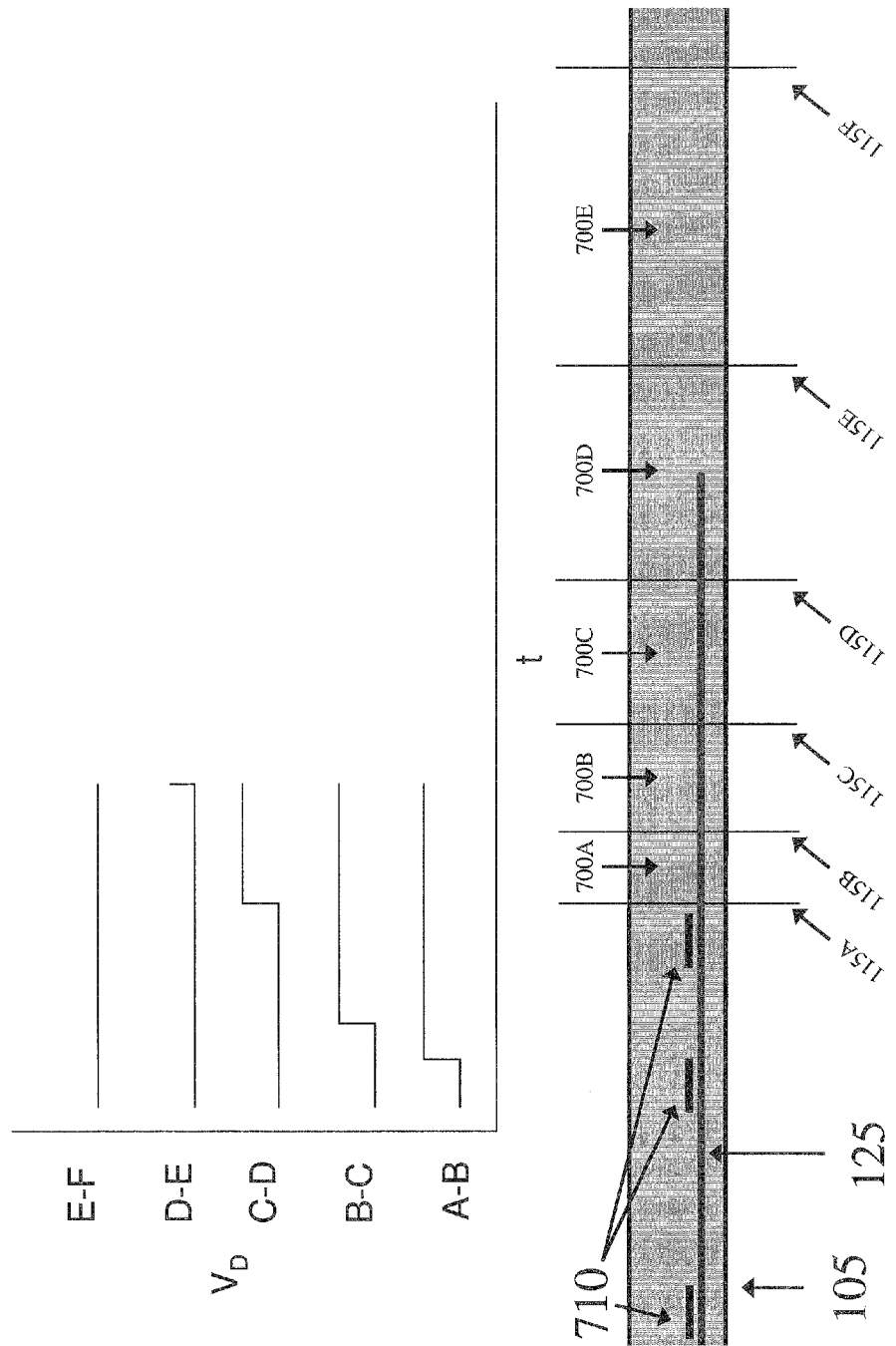
Figure 11C:
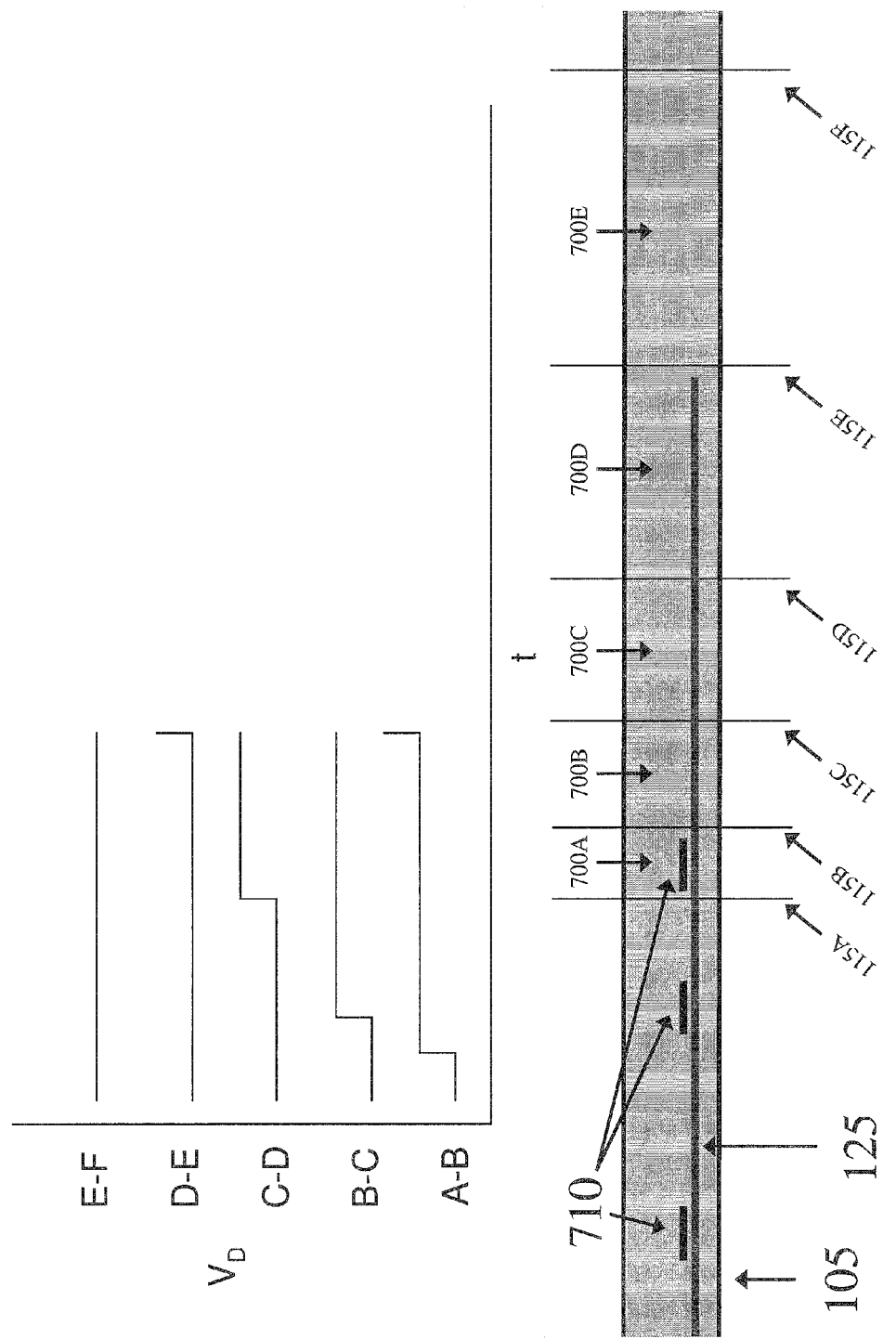
Figure 11F:
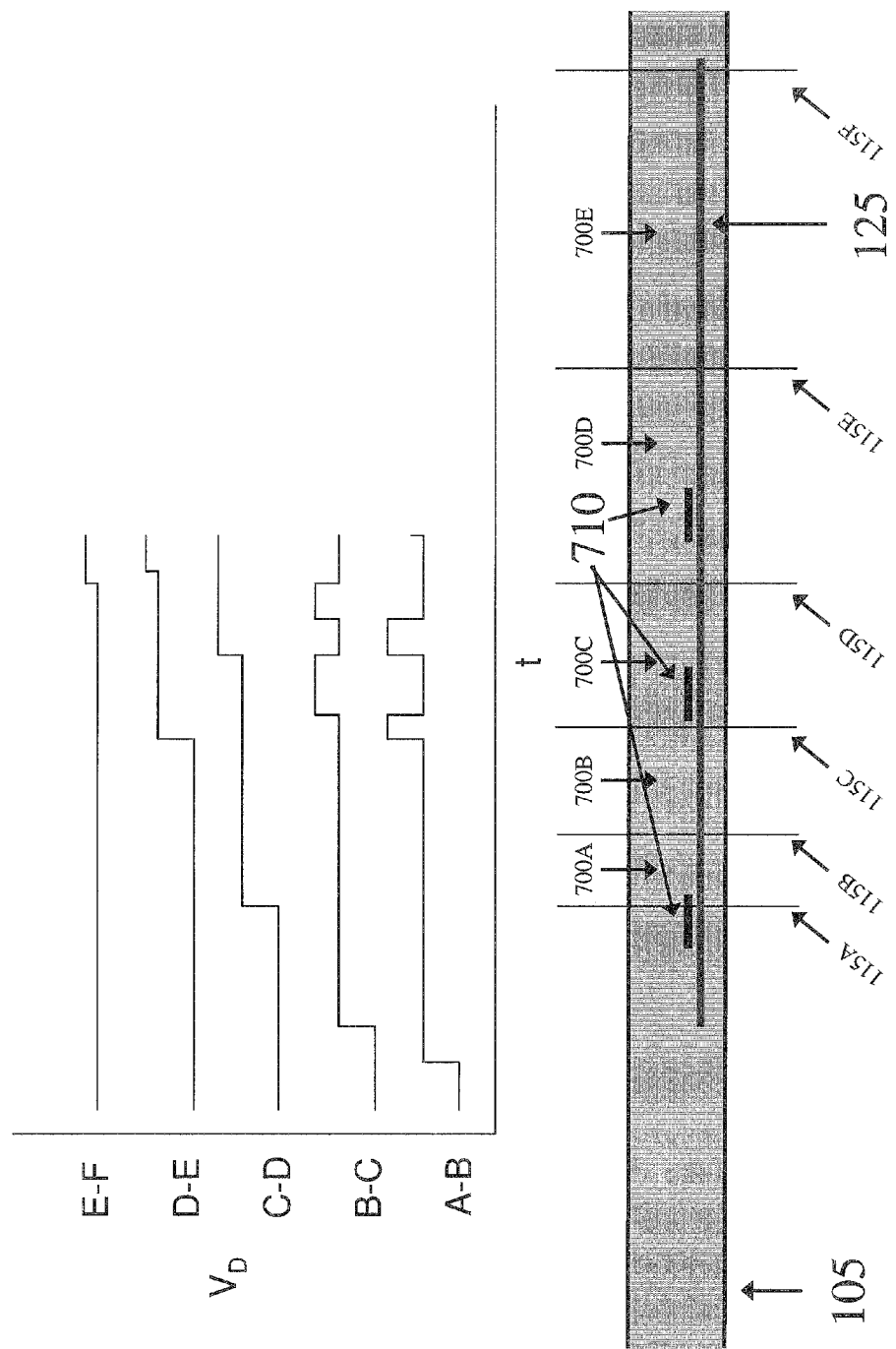

The arrangement of FIG. 10 is shown in use in FIG. 11a-g, where a biomolecule 125 with hybridized probes 710 is disposed in a fluidic channel. The detector volume 700E between detector electrodes 115E-115F contains two probes 710", 710'". The distance between the two probes 710", 710'", therefore, is less than the distance between detector electrode 115E and detector electrode 115F. Two peaks for a signal from the same detector volume, e.g., 700E, indicate that the distance between two detector electrodes 115E, 115F associated with the detector volume 700E is an upper limit of the distance separating two detected probes. FIGS. 11b-11g illustrate the translocation of the biomolecule with hybridized probes 710 being translocated through the fluidic channel; the electrical signals reflect the positions of the biomolecule and probes 710 in the detector volumes 700 between detector electrodes 115A-115F having variable distances. Referring to FIG. 11e, coincident signals from two different detector volumes 700A, 700C are indicative of a distance between the probes.

Sequencing by Using Probes

Sequencing a biomolecule such as single-stranded or double-stranded DNA or RNA using one or more probes may be performed as follows, in combination with the length/distance measurement techniques disclosed herein.

Figure 12:
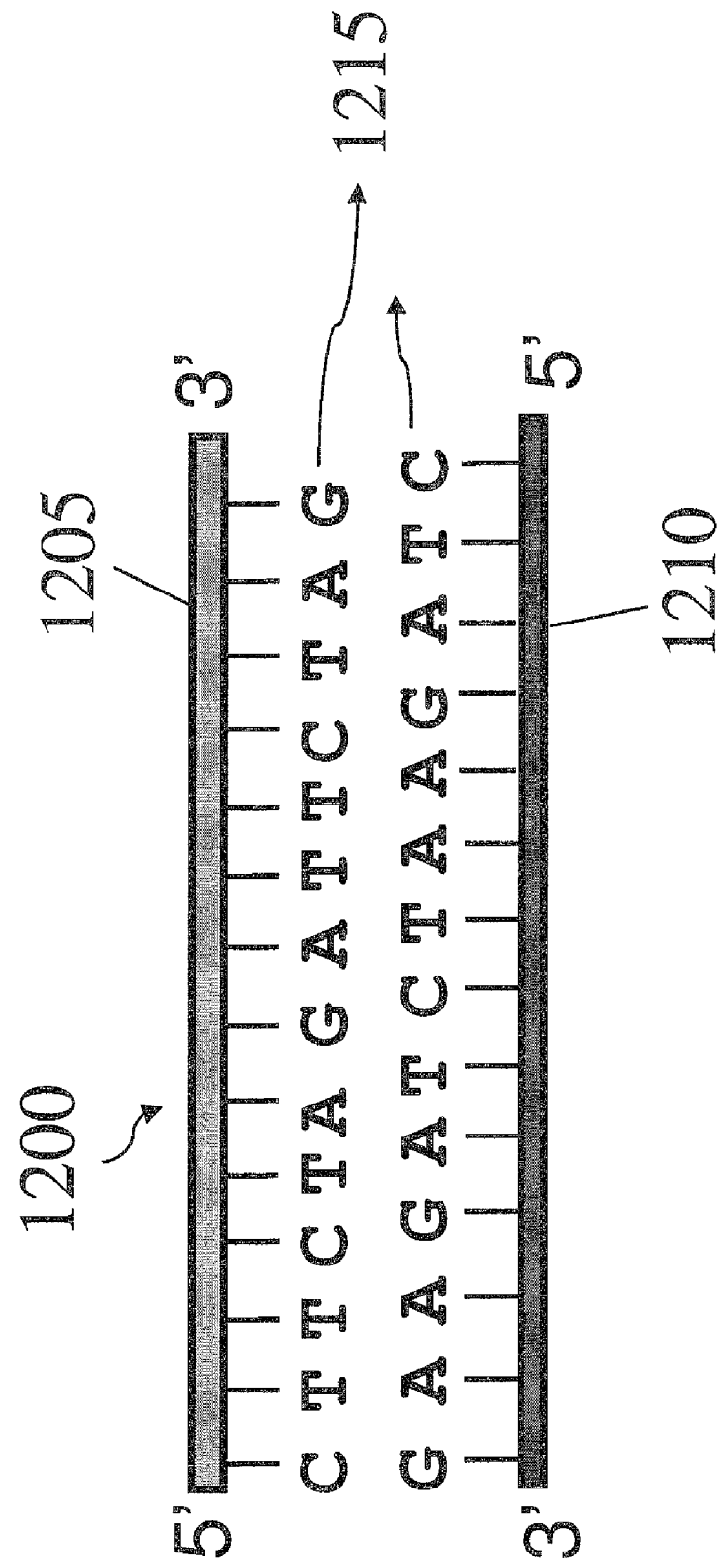
FIG. 12 is a schematic depiction of a DNA molecule (SEQ ID NO: 2)
Figure 13:
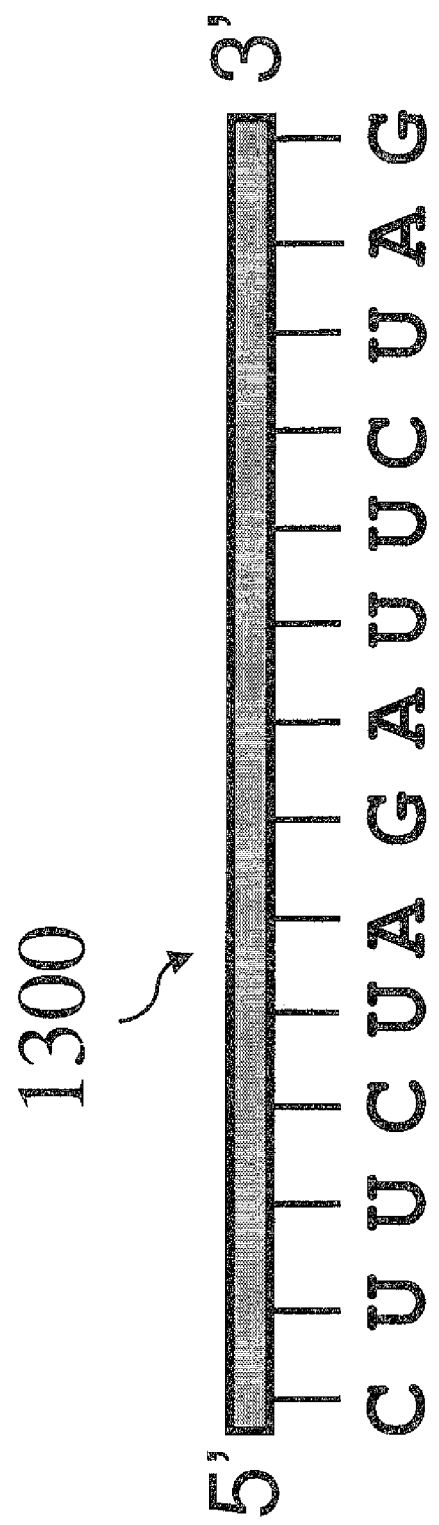
FIG. 13 is a schematic depiction of an RNA molecule (SEQ ID NO: 3)

Referring to FIG. 12, a DNA molecule 1200, i.e., a type of analyte 125, is schematically depicted and is structured in two strands 1205, 1210 positioned in anti-parallel relation to one another. Each of the two opposing strands 1205, 1210 may be sequentially formed from repeating groups of nucleotides 1215 where each nucleotide 1215 consists of a phosphate group, 2-deoxyribose sugar and one of four nitrogen-containing bases. The nitrogen-containing bases include cytosine (C), adenine (A), guanine (G) and thymine (T). DNA strands 1205 are read in a particular direction, from the so-called the 5' or "five prime" end to the so-called the 3' or "three prime" end. Similarly, RNA molecules 1300, as schematically depicted in FIG. 13, are polynucleotide chains, which differ from those of DNA 1200 by having ribose sugar instead of deoxyribose and uracil bases (U) instead of thymine bases (T). RNA strands 1300 are also read from the 5' end to the 3' end.

Traditionally, in determining the particular arrangement of the bases 1215 and thereby the sequences of the molecules, a process called hybridization may be utilized. The hybridization process is the coming together, or binding, of two genetic sequences with one another. This process is predictable because the bases 1215 in the molecules do not share an equal affinity for one another. T (or U) bases favor binding with A bases while C bases favor binding with G bases. Sequence selective binding is mediated via hydrogen bonds that exist between the opposing base pairs. For example, A and T (or U) for two hydrogen bonds using two hydrogen bond acceptor and donors that are lined up with respect to each other in the duplex. Similarly the nucleosides C and G bind to one another via three hydrogen bonds formed by hydrogen bond acceptor and donors on the bases.

Figure 14:
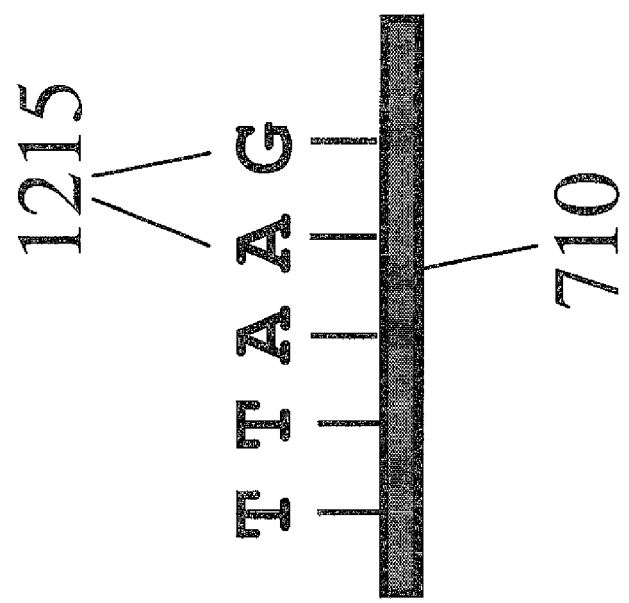
FIG. 14 is a schematic depiction of a hybridizing oligonucleotide (or probe)

A hybridizing oligonucleotide, i.e., a probe 710 may be used to determine and identify the sequence of bases 1215 in the molecule of interest. FIG. 14 illustrates a probe 710 that is a short DNA sequence having a known composition. Probes 710 may be of any length depending on the number of bases 1215 that they include. For example, a probe 710 that includes six bases 1215 is referred to as a six-mer wherein each of the six bases 1215 in the probe 710 may be any one of the known four natural base types A, T(U), C or G and alternately may include non-natural bases.

In this regard, the total number of unique probes 710 in a library depends upon the number of bases 1215 contained within each probe 710 and the number of different types of bases in the probes. If only the four natural bases are used in probe 710, the total number of probes in the library is determined by the formula $4^n$ (four raised to the n power) where n is equal to the total number of bases 1215 in each probe 710. Formulas for other arrangements or types of bases are well known in the art. Accordingly, the size of the probe library can be expressed as $4^n$ n-mer probes 710. For the purpose of illustration, in the context of a six-mer probe, the total number of possible unique, identifiable probe combinations includes $4^6$ (four raised to the sixth power) or 4096 unique six-mer probes 710. The inclusion of non-natural bases allows for the creation of probes that have spaces or wildcards therein in a manner that expands the versatility of the library's range of probe recognition. Probes that include universal bases organized into patterns with natural bases may also be used, as described previously.

Figure 15:
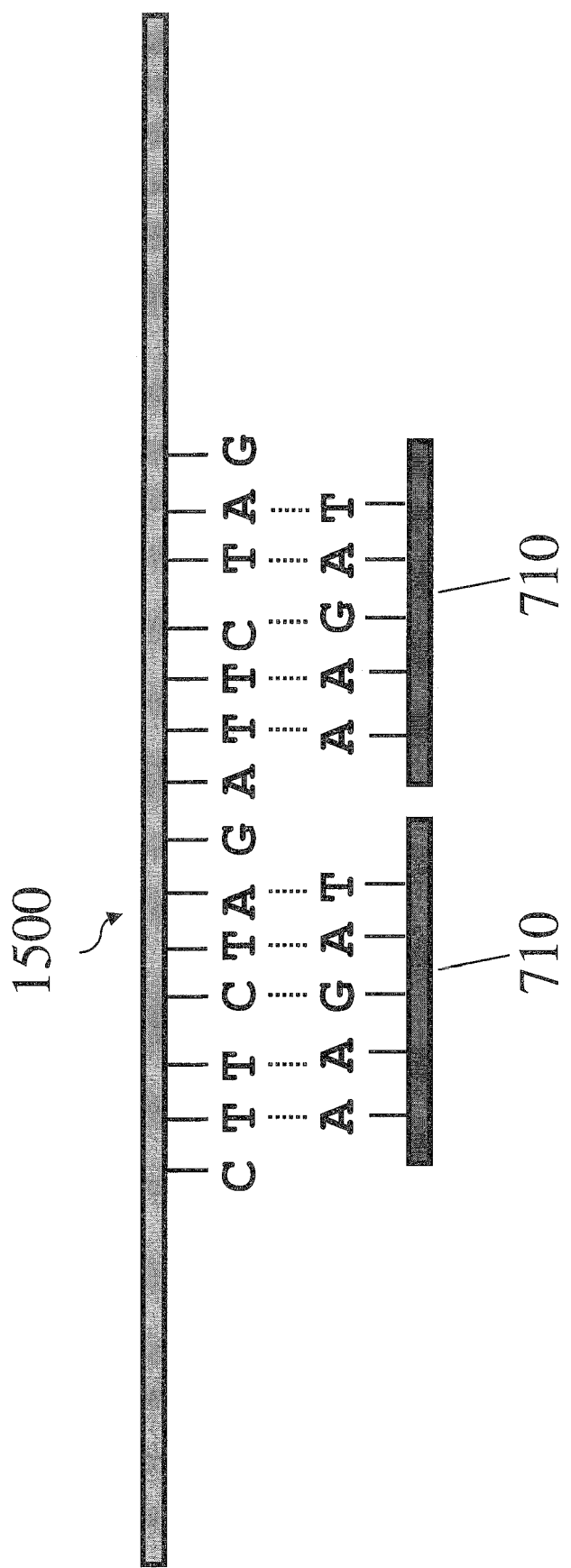
FIG. 15 is a schematic depiction of a single-stranded DNA molecule (SEQ ID NO: 2) hybridized with a probe.

The process of hybridization using probes 710, as depicted in FIG. 15, may begin by denaturing a double-stranded biomolecule to produce a single-stranded fragment 1500, i.e., a basis for an analyte 125. Very small amounts, i.e., less than a milligram of DNA may be used. Preferably less than 100 micrograms of DNA may be used. More preferably, less than 20 micrograms may be used. Most preferably 1-10 micrograms of DNA may be used. For re-sequencing applications or for applications that do not sequence an entire human or other genome, the amount of DNA used may be less than a nanogram. Denaturing is accomplished usually through the application of heat or chemicals, such that the hydrogen bonds between the two strands of the original double-stranded DNA are broken leaving two single strands of DNA whose bases are now available for hydrogen bonding. After the biomolecule 1500 has been denatured, a single-stranded probe 710 may be introduced to the biomolecule 1500 to locate portions of the biomolecule 1500 that have a base sequence that correlates to the sequence that is found in the probe 710. In order to hybridize the biomolecule 1500 with the probe 710, the denatured biomolecule 1500 and a plurality of the probes 710 having a known sequence are both introduced into a solution. The solution may be an ionic solution, such as a salt-containing solution. The solution conditions, such as salt concentration, ionic concentration, temperature and pH are set to insure stringent and accurate binding of the probe 710 to the complimentary portion of the biomolecule 1500. The mixture may be agitated to facilitate binding of the probes 710 to the biomolecule 1500 strand along regions thereof that have a matched complementary sequence. Hybridization of the biomolecule 1500 with the probe 710 may be accomplished before the biomolecule 1500 is introduced into a sequencing apparatus or after the denatured biomolecule 1500 has been placed into a cis chamber 1615 of the apparatus described below with reference to FIG. 16. In this case, after the denatured biomolecule has been added to the cis chamber 1615, buffer solution containing probes 710 with a known sequence is also added to the cis chamber 1615 and allowed to hybridize with the biomolecule 1500 before the partially hybridized biomolecule is translocated. In some embodiments, the biomolecule may be coated with one or more proteins, as discussed in detail below.

Figure 16:
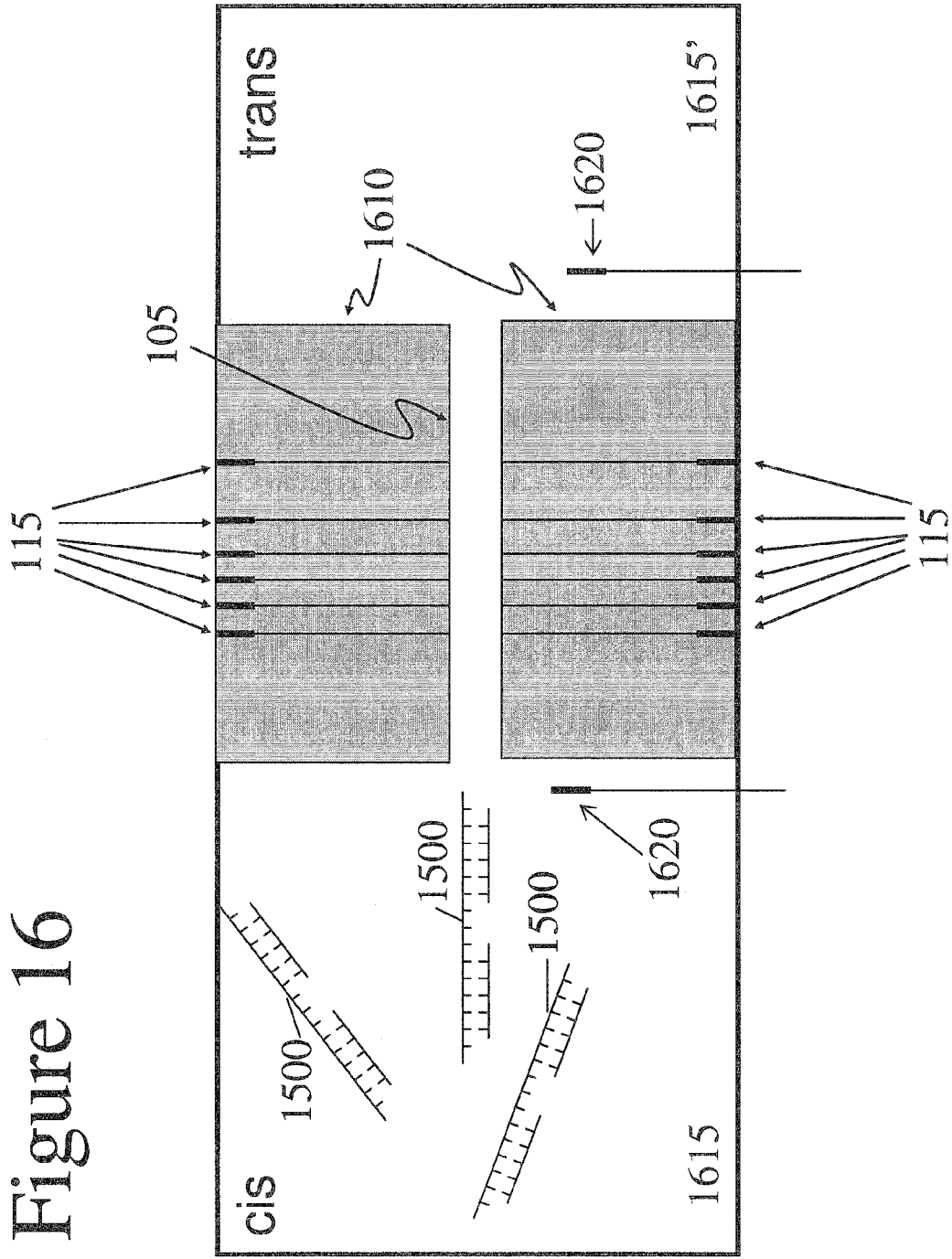
FIG. 16 is a schematic depiction of a microfluidic channel apparatus employed in a method of an embodiment of the present invention.

An embodiment of a fluidic channel sequencing arrangement is graphically depicted in FIG. 16. A structure may define a fluidic channel 105, i.e., a microchannel or a nanochannel. In other embodiments, the structure may define a nanopore. Accordingly, in the context of the present invention, the term "structure" may be used to refer to structures defining nanopores, as well as fluidic channels such as microchannels and nanochannels.

For the purpose of illustration, relatively short biomolecule strands 1500 with only two bound probes 710 are depicted. Long-stranded biomolecules 1500 may be translocated through the structure, i.e., fluidic channel 105, to determine the location of the probes 710 attached thereto. The sequencing arrangement 1600 includes a fluidic channel 105 defined in an insulating material 1610. For example, the fluidic channel 105 may be formed in a solid-state material. Further, the fluidic channel 105 may have a diameter that allows the passage of uncoated, double-stranded DNA and have dimensions of width and depth that are between approximately 1 nm and 5 μm, preferably between 2.3 nm and 100 nm, more preferably between 2.3 nm and 50 nm, e.g., 30 nm. In the case of double-stranded DNA samples coated with a protein such as RecA, the fluidic channel 105 is preferably at least 10 nm in width, more preferably about 100 nm.

A structure defining the fluidic channel 105 is positioned between a first and a second fluid chamber, i.e., a cis chamber 1615, and a trans chamber 1615', each of which is filled with a fluid. The cis chamber 1615 and the trans chamber 1615' are in fluidic communication with one another via the structure including fluidic channel 105 located in the insulating material 1610. In the case of a fluidic channel, a voltage is applied along at least a length of the fluidic channel 105. This potential difference between the chambers 1615 on opposing sides of the fluidic channel 105 results in a measurable ionic current flow through the fluidic channel 105. In one embodiment, an electrode 1620 may be installed into each of the cis 1615 and trans 1615' chambers to apply an electrical potential down the length of the fluidic channel 105. In an embodiment, the electrode in the cis chamber 1615 is a cathode, and the electrode in the trans chamber 1615' is an anode. At least one pair of electrodes 115 defines at least one detector volume within the structure.

The hybridized biomolecule strand 1500 with the probes 710 attached thereto is then introduced into the cis chamber 1615 in which the cathode is located. In an embodiment, the biomolecule 1500 is then driven or translocated through the detector volume in the fluidic channel 105 as a result of the applied voltage. As the biomolecule 1500 passes through at least one detector volume in the channel 105, an electrical property detected by the at least one pair of electrodes 115 defining the at least one detector volume is monitored, as a function of time. The electrical property may be changes in the electrical potential between pairs of electrodes defining at least one detector volume as the partially hybridized biomolecule translocates therethrough or changes in a current applied between electrodes across the channel.

Figure 17:
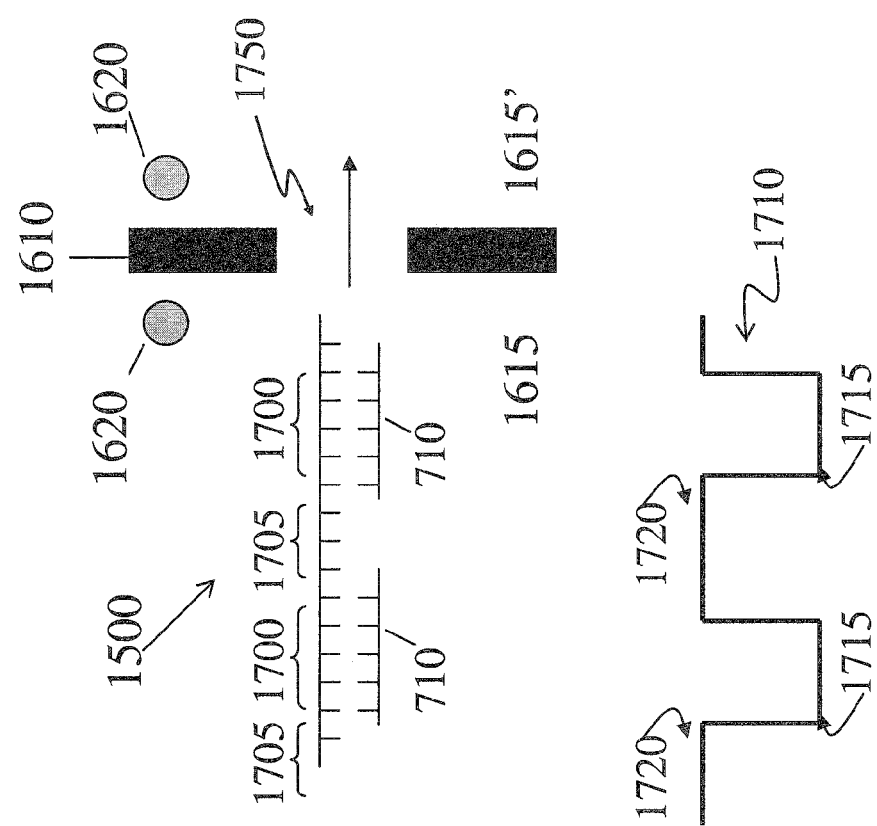
FIG. 17 is a close-up view of a hybridized biomolecule translocating through the nanopore of the apparatus in FIG. 16.

An analogous situation in which current is measured during translocation of a DNA strand through a nanopore is shown in FIG. 17. In the case of a nanopore 1750, the measured current runs parallel to the movement of the biomolecule 1500. For a fluidic channel system, a current-based sensor may measure the current between electrodes on opposing sides of the fluidic channel 105. The current measurement is thus essentially perpendicular to the direction of movement of the biomolecule 1500. In the case of the nanopore, variations in current are the result of the relative diameter of the biomolecule 1500 that is passing through the nanopore 1750 at any given time. For example, the portions 1700 of the biomolecule 1500 that have probes 710 bound thereto are twice the diameter of the portions 1705 of the biomolecule 1500 that have not been hybridized and therefore lack probes 710. This relative increase in volume of the biomolecule 1500 passing through the nanopore 1750 causes a temporary interruption or decrease in the current flow therethrough, resulting in a measurable current variation as is depicted in the waveform 1710 at the bottom of the figure. As the portions 1700 of the biomolecule 1500 that include probes 710 pass through the nanopore 1750, the current is partially interrupted forming a relative trough 1715 in the recorded current during passage of the bound portion 1700. Similarly, as the unhybridized portions 1705 of the biomolecule 1500 pass, the current remains relatively high forming a peak 1720 in the measured current. The electrodes 1620 installed in the cis 1615 and trans 1615' chambers, on opposite sides of the structure defining the nanopore 1750, detect and reflect these variations in the monitored current. Further, the measurements of the current variations are measured and recorded as a function of time. As a result, the periodic interruptions or variations in current indicate where, as a function of relative or absolute position, the known probe 710 sequence has attached to the biomolecule 1500.

In an analogous fashion, the potential measured between electrodes 115 in FIG. 16 will change as portions 1700 of the biomolecule 1500 that include probes 710 pass through the detector volumes delineated by electrodes 115. The periodic changes in potential or current indicate where, as a function of relative or absolute position, the known probe 710 sequence has attached to the biomolecule 1500.

In yet another embodiment, detector electrodes 115 cross the channel as shown in FIGS. 7-11 to thereby define detector volumes between adjacent detector electrodes. In this embodiment, an electrical potential is applied along the length of the channel, and changes in electrical potential can be detected in any one or more detector volumes defined between electrode pairs. As shown in FIGS. 7-11, this configuration also allows one to identify and distinguish detection volumes that have no biomolecule present, detection volumes that have present a portion of the biomolecule lacking probes, and detection volumes that have present a portion of the biomolecule including probes. The periodic changes in electrical potential indicate where, as a function of relative or absolute position, the known probe 710 sequence has bound to the biomolecule 1500.

Figure 18:
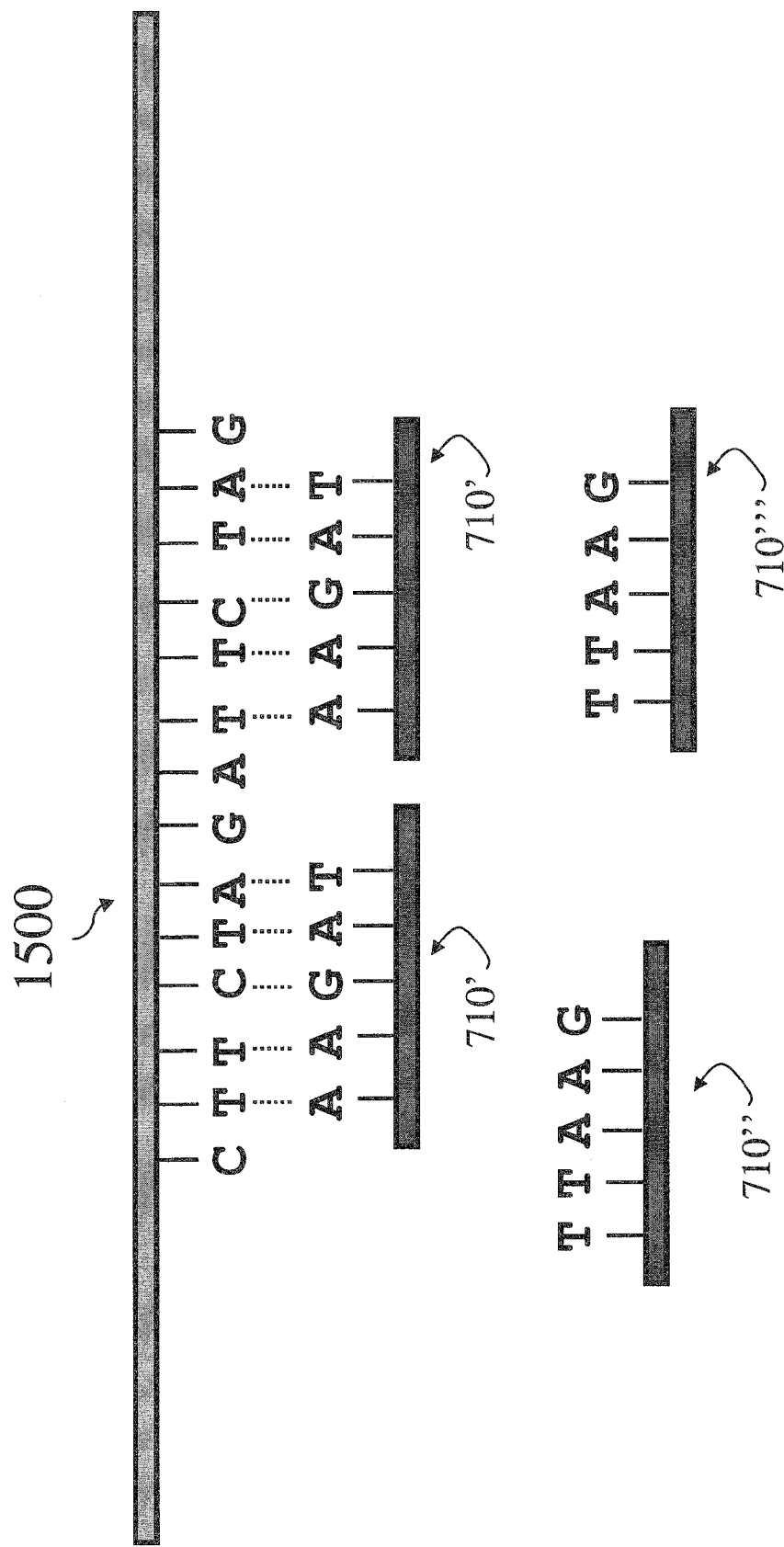
FIG. 18 (SEQ ID NO: 2) depicts the results from a repetitive application of a method of the present invention using different probes.

The measurements obtained and recorded, as well as the time scale, may be input into a computer algorithm that maps the binding locations of the known probe 710 sequences along the length of the biomolecule 1500. Once the probe 710 locations are known, since the probe 710 length and composition is known, the sequence of the biomolecule 1500 along the portions 1700 to which the probes 710 were attached can be determined. This process can then be repeated using a different known probe 710. Further, the process can be repeated until every probe 710 within the library of n-mer probes has been hybridized with the biomolecule 1500 strand of interest. It can be seen in FIG. 18 that by repeating the process with different known probes 710', 710" and 710''', the gaps in the portions of the biomolecule 1500 are gradually filled in with each subsequent hybridization and sequencing step until eventually the entire sequence of the biomolecule 1500 of interest is known.

In one embodiment, sequencing is enhanced using so-called "overlapping" probes. In this embodiment, fewer probes may be employed to develop more complete sequence data. Specifically, probes are selected such that they selectively hybridize to complementary regions on the target biomolecule that share a sub-region. Each probe set hybridizes to a different complementary region. Thus, in the case of six-mer probes for example, a first set of probes having sequence A-T-A-G-C-T (which selectively binds to T-A-T-C-G-A regions of the biomolecule) may be employed, and a second set of probes having a sequence C-T-G-G-C-A (which selectively binds to G-A-C-C-G-T regions of the biomolecule) may be employed. Note that each of the regions to which probes will bind shares a C-T subregion. In other words, at least one region complementary to the first probe set shares a subregion that is complementary to the second probe set. Thus, regions of the biomolecule which bind both probes allow data to be linked, thereby allowing biomolecule regions of sequence T-A-T-C-G-A-C-C-G-T (SEQ ID NO: 1) to be identified. By performing multiple such analyses, it becomes possible to develop extensive sequence data using only a subset of the entire probe library.

Each subsequent hybridization and sequencing of the biomolecule 1500 may be accomplished in a variety of ways. For example, a plurality of nanopore assemblies, each sequencing copies of the same biomolecule of interest using different known probes, may be utilized simultaneously in a parallel fashion. Similarly, the same biomolecule may be repetitively hybridized and sequenced by passing it through a series of interconnected chambers. Finally, any combination of the above two processes may also be employed.

Detection of variations in electrical potential between the cis 1615 and trans chambers 1615' as the hybridized biomolecule 1500 of interest passes through the nanopore 1750 may be accomplished in many different ways. For example, the variation in current flow as described above may be measured and recorded. Optionally, the change in capacitance as measured on the nanopore membrane itself may be detected and recorded as the biomolecule 1500 passes through the nanopore. Finally, the quantum phenomenon known as electron tunneling may be measured, whereby electrons travel in a perpendicular fashion relative to the path of travel taken by the biomolecule. In essence, as the biomolecule 1500 passes through the nanopore 1750, the probe 710 locations bridge the nanopore 1750, thereby allowing electrons to propagate across the nanopore in a measurable event. As the electrons propagate across the nanopore, the event is measured and recorded to determine the relative probe binding locations. The particular method by which the electrical variations are measured is not important, only that fluctuation in electrical properties is measured as they are impacted by the passing of the biomolecule through the nanopore.

The manner in which the electrical potential varies, as a function of time, may depend on whether a single-stranded (un-hybridized) or double-stranded (hybridized) region of the biomolecule is passing through the nanopore 1750 and may be complicated. In the simplest scenario, the double-stranded region 1700 may suppress the current in comparison to the single-stranded region 1705, which may suppress the current in comparison to when no biomolecule 1500 is translocating. However, for small nanopore 1750 dimensions or low salt concentrations, the current may be augmented with the translocation of double-stranded portions 1700. In this case, the points of increased current may be used as an indicator of where the probes 710 are positioned along the biomolecule 1500.

The recorded changes in electrical potential across the nanopore 1750 as a factor of time may then processed using a computer and compiled using the sequences of the known probes 710 to reconstruct the entire sequence of the biomolecule 1500 strand of interest.

Preparation of the Biomolecule Sample

Methods to increase the signal-to-noise ratio in nanopore or fluidic channel translocation of biomolecules that have been hybridized to probes are disclosed herein. In one embodiment, a single- or double-stranded biomolecule may be hybridized with a probe. The hybridized biomolecule may then be incubated with a protein or enzyme that binds to the biomolecule and forms at least a partial coating along the biomolecule.

RecA protein from *E. coli* typically binds single- or double-stranded DNA in a cooperative fashion to form filaments containing the DNA in a core and an external sheath of protein (McEntee, K.; Weinstock, G. M.; Lehman, I. R. Binding of the RecA Protein of *Escherichia coli* to Single- and Double-Stranded DNA. *J. Biol. Chem.* 1981, 256, 8835). DNA has a diameter of about 2 nm, while DNA coated with RecA has a diameter of about 10 nm. The persistence length of the DNA increases to around 950 nm, in contrast to 0.75 nm for single-stranded DNA or 50 nm for double-stranded DNA. T4 gene 32 protein is known to cooperatively bind single-stranded DNA (Alberts, B. M.; Frey, L. T4 Bacteriophage Gene32: A Structural Protein in the Replication and Recombination of DNA. *Nature,* 1970, 227, 1313-1318). *E. coli* single-stranded binding protein binds single-stranded DNA in several forms depending on salt and magnesium concentrations (Lohman, T. M.; Ferrari, M. E. *Escherichia Coli* Single-Stranded DNA-Binding Protein: Multiple DNA- Binding Modes and Cooperativities. *Ann. Rev. Biochem.* 1994, 63, 527-570). The *E. coli* single-stranded binding protein may form a varied coating on the biomolecule. The f1 geneV protein is known to coat single-stranded DNA (Terwilliger, T. C. Gene V Protein Dimerization and Cooperativity of Binding of poly(dA). *Biochemistry* 1996, 35, 16652), as is human replication protein A (Kim, C.; Snyder, R. O.; Wold, M. S. Binding properties of replication protein A from human and yeast cells. *Mol. Cell. Biol.* 1992, 12, 3050), Pf3 single-stranded binding protein (Powell, M. D.; Gray, D. M. Characterization of the Pf3 single-strand DNA binding protein by circular dichroism spectroscopy. *Biochemistry* 1993, 32, 12538), and adenovirus DNA binding protein (Tucker, P. A.; Tsernoglou, D.; Tucker, A. D.; Coenjaerts, F. E. J.; Leenders, H.; Vliet, P. C. Crystal structure of the adenovirus DNA binding protein reveals a hook-on model for cooperative DNA binding. *EMBO J.* 1994, 13, 2994). The protein-coated DNA is then translocated through a nanopore as has been demonstrated with RecA bound to double-stranded DNA (Smeets, R. M. M.; Kowalczyk, S. W.; Hall, A. R.; Dekker, N. H.; Dekker, C. Translocation of RecA-Coated Double-Stranded DNA through Solid-State Nanopores. Nano Lett. 2009). Translocation of protein bound to single-stranded DNA is contemplated herein. The protein coating functions in the same manner for single-stranded DNA and double-stranded DNA.

Figure 19:
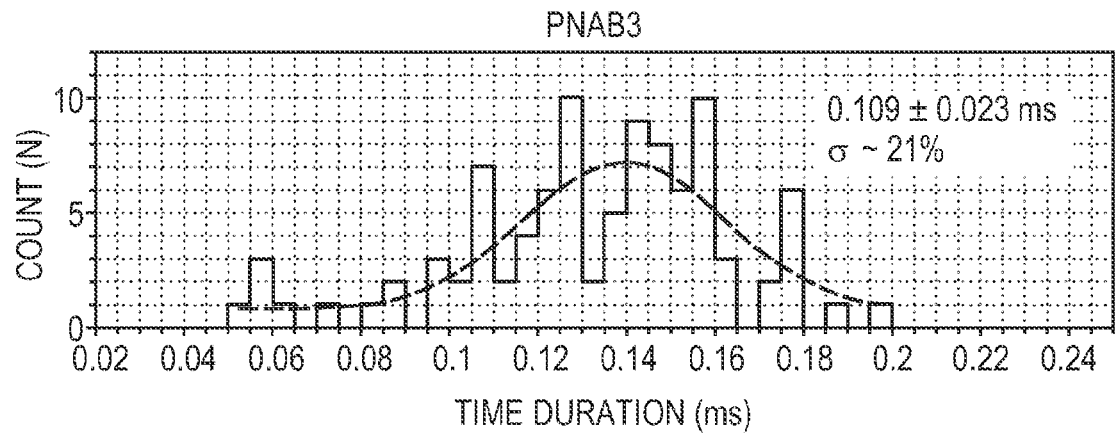
FIG. 19 is a histogram of duration times for translocation times of 5.6 kbp double-stranded DNA translocating through a 7 nm pore.
Figure 20:
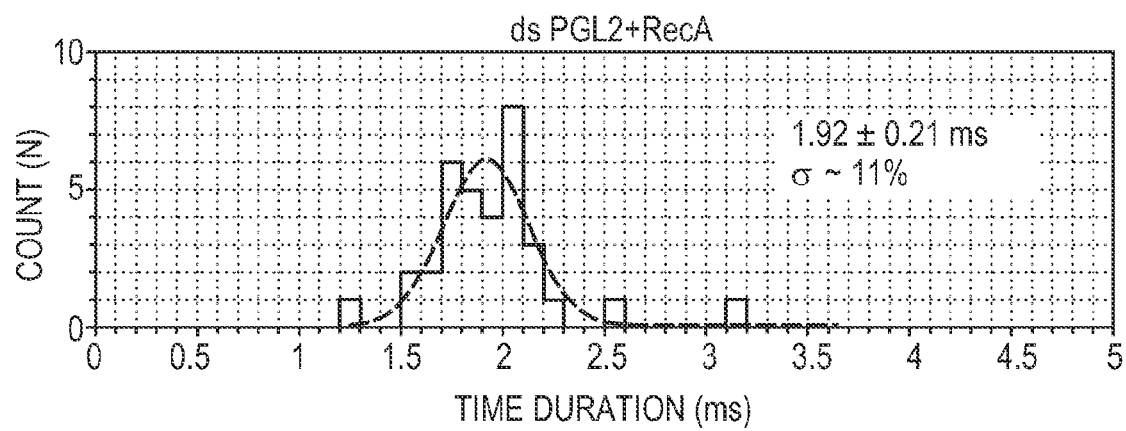
FIG. 20 is a histogram of duration times for translocation of RecA coated 5.6 kbp double-stranded DNA translocating through a 25 nm pore.

Coated biomolecules typically have greater uniformity in their translocation rates, which leads to a decrease in positional error and thus more accurate sequencing. FIGS. 19 and 20 demonstrate the reproducibility in translocation rates using methods described herein. Due to its increased diameter, a coated biomolecule generally translocates through a nanopore at a slower speed than a non-coated biomolecule. The translocation is preferably slow enough so that a signal can be detected during its passage from the first chamber into the second chamber. The translocation rate or frequency may be regulated by introducing a salt gradient between the first and second chambers. Exemplary salt concentration ratios of the cis to the trans side of the chamber may include, but are not limited to, 1:2, 1:4, 1:6, and 1:8. For example, salt concentrations may range from about 0.5 M KCl to about 1 M KCl on the cis side and from about 1 M KCl to about 4 M KCl on the trans side. The signal is preferably strong enough to be detected using known methods or methods described herein. Exemplary signal-to-noise ratios include, but are not limited to, 2:1, 5:1, 10:1, 15:1, 20:1, 50:1, 100:1, and 200:1. With a higher signal-to-noise ratio, a lower voltage may be used to effect translocation. However, too low a voltage may prevent translocation altogether.

In one embodiment, a biomolecule of interest is hybridized with the entire library of probes of a given length. For example, the biomolecule of interest can be hybridized with the entire universe of 4096 possible six-mers. The hybridization can be done sequentially (i.e., one probe after another) or in parallel (i.e., a plurality of biomolecules of interest are each separately hybridized simultaneously with each of the possible probes). Alternatively, the probes can be separated from each other in both space and time. Additionally, more than one probe type may be hybridized to the same biomolecule of interest at the same time.

The set of probes used to perform the sequencing may be a subset of the complete library of probes of a given length, such as about 85%, 75%, 65%, 55%, 45%, or 33% of the library. For instance, if sequencing is performed on a biomolecule that starts as double-stranded DNA, then only one-half of the probes that make up a library may be needed. Other subsets of the library may be designed to allow sequencing as well. If some information concerning the target sequence is known prior to performing the sequencing reaction, it may be possible to use a small subset of the total library. For instance, if the sequencing reaction is being performed to determine if single nucleotide polymorphisms are present with respect to a reference sequence, then a small number of probes with respect to the complete library may be used. Alternatively, the set of probes may not all be the same length. In an embodiment, a set of at least two probes may be used for hybridization, rather than an entire library of probes or subset thereof. In another embodiment, probes may be separated by (GC) content or other determinants of probe binding strength, in order to allow for optimization of reaction conditions. By separating the probes based on relative properties, multiple probes may be incorporated into a single hybridization reaction. Further, the probes may be grouped based on their related optimum reaction environment preferences. In yet another embodiment, pools of probes may be simultaneously hybridized to a biomolecule of interest. A pool of probes is a group of probes of different composition, each of which may likely be present in many copies. The composition of the probes may be chosen so as to reduce the chance of competitive binding to the biomolecule of interest. Alternatively, the composition of multiple pools may be chosen so that the same competitive binding is not present in all pools occupied by a single probe.

In still another embodiment, the probes may be attached to tags, making the current fluctuations more noticeable as the hybridized probes translocate through the nanopore. In addition, different tags may be used to help distinguish among the different probes. These tags may be proteins, double-stranded DNA, single-stranded DNA or other molecules.

Figure 21:
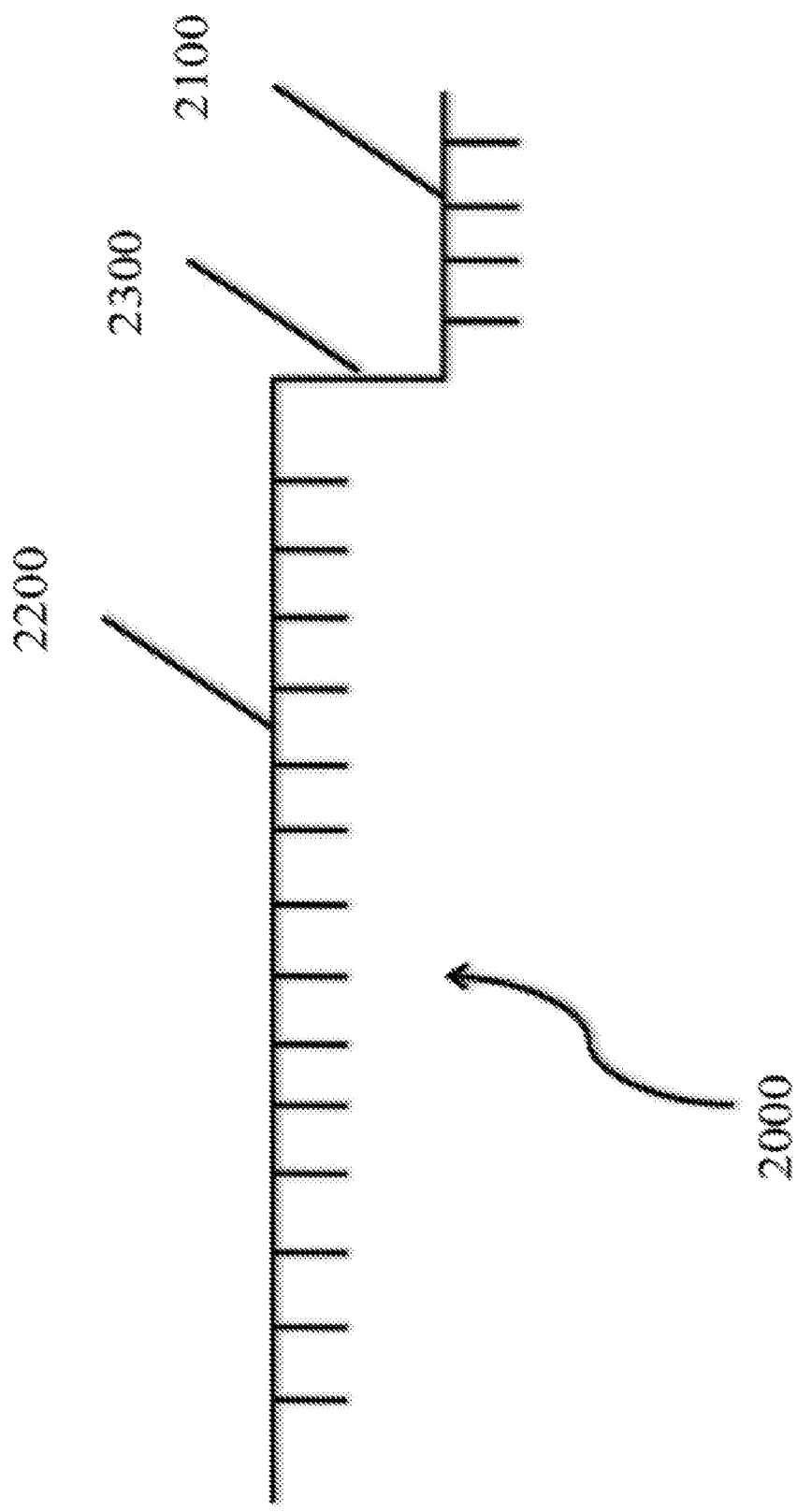
FIG. 21 is a schematic representation of a hybridizing oligonucleotide (probe) and an associated tag.
Figure 22A:
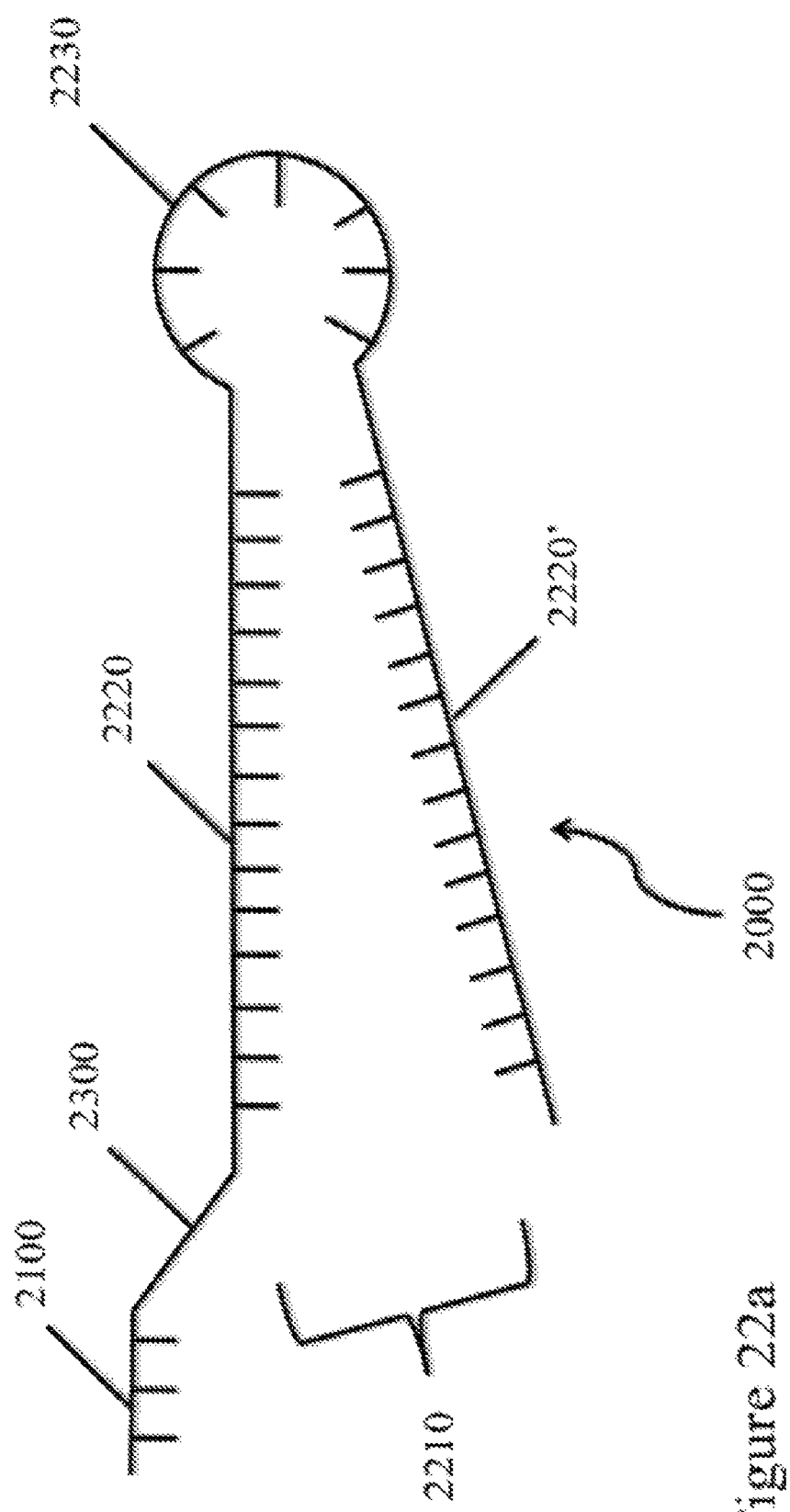
FIG. 22a is a schematic representation of one embodiment of a probe having an associated tag, whereby the tag can be annealed to form a DNA hairpin structure.
Figure 22B:
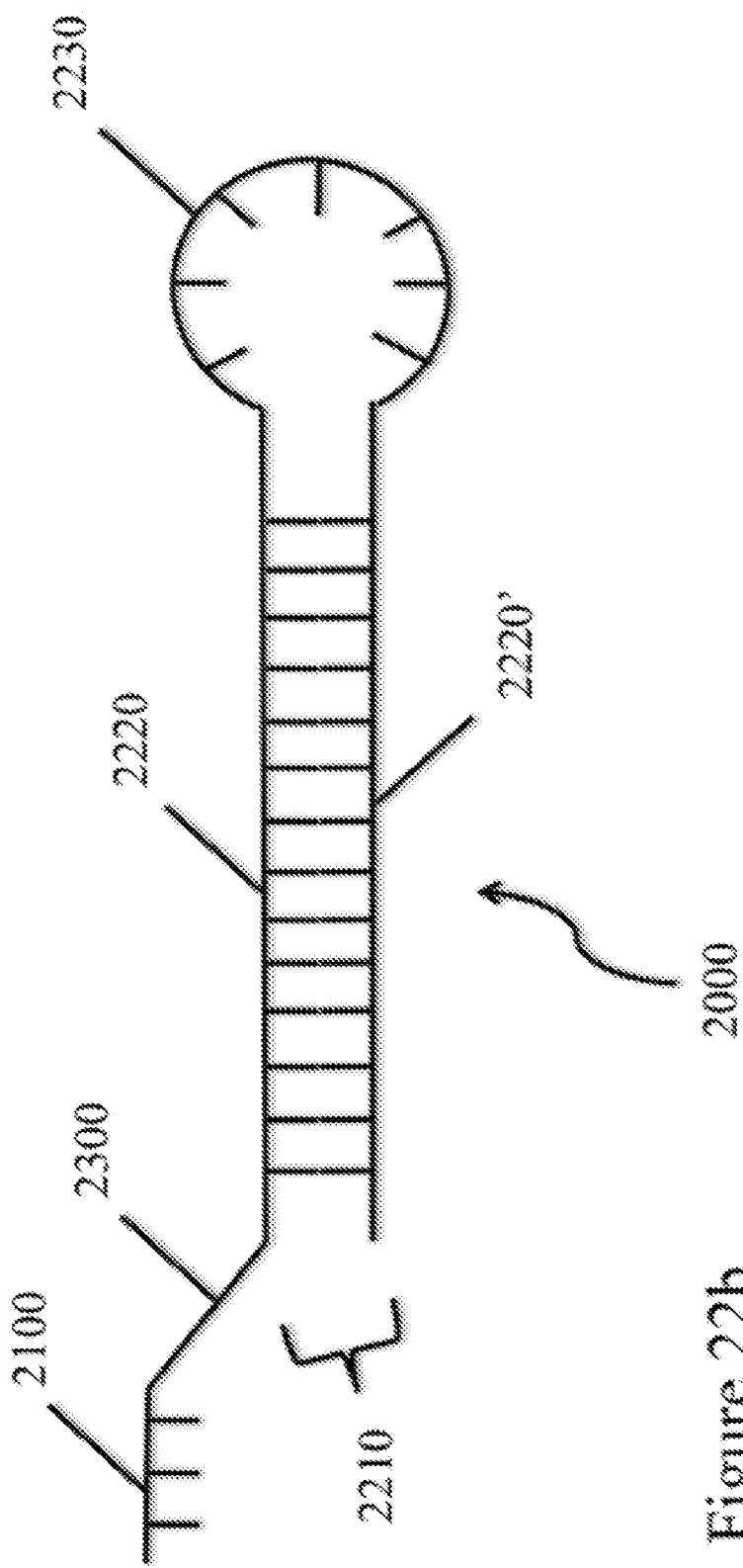
FIG. 22b is a schematic representation of the probe of FIG. 22a following annealing of the associated tag.

More specifically, as shown in FIG. 21, a tagged probe 2000 may include a probe region 2100, such as for example a 6-mer probe, connected to a tag 2200 by a linker 2300. As noted above, tag 2200 may include protein, double-stranded DNA, single stranded DNA or other molecules. The length of the tags is not intended to be limiting, however, tags in the range of about 35 bases to about 200 bases are preferred. In one embodiment, depicted in FIGS. 22a and 22b, the tagged probe may include a tag having a structure such as a DNA hairpin. In this case, the tagged probe 2000 includes a probe region 2100, a linker 2300, and a tag structure 2210 including a first DNA region 2220 connected to a second, complementary DNA region 2220' by a loop region 2230. In FIG. 22a, the tag structure 2210 has not yet been annealed and is present as a single-stranded DNA. In FIG. 22b, the complementary first 2220 and second 2220' DNA regions have been annealed to create the tag structure 2210 in the form of a DNA hairpin. More complex structural elements may be used to tag the probe. For instance, two consecutive hairpins may be linked to the probe through a linker. Other secondary structure elements such as t-structures may also be used.

Figure 23A:
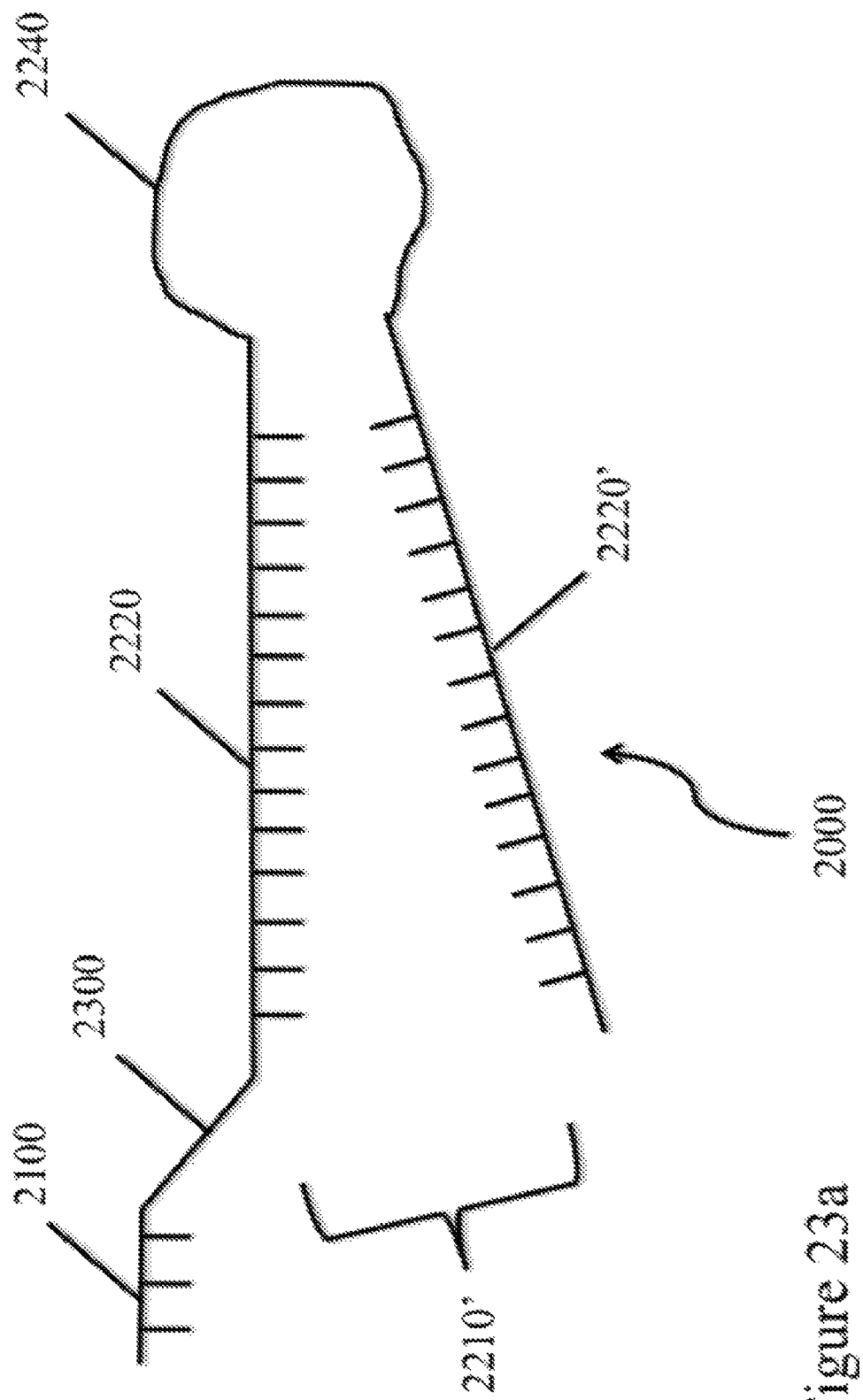
FIG. 23a is a schematic representation of a second embodiment of a probe having an associated tag, whereby the tag can be annealed to form a DNA hairpin structure.
Figure 23B:
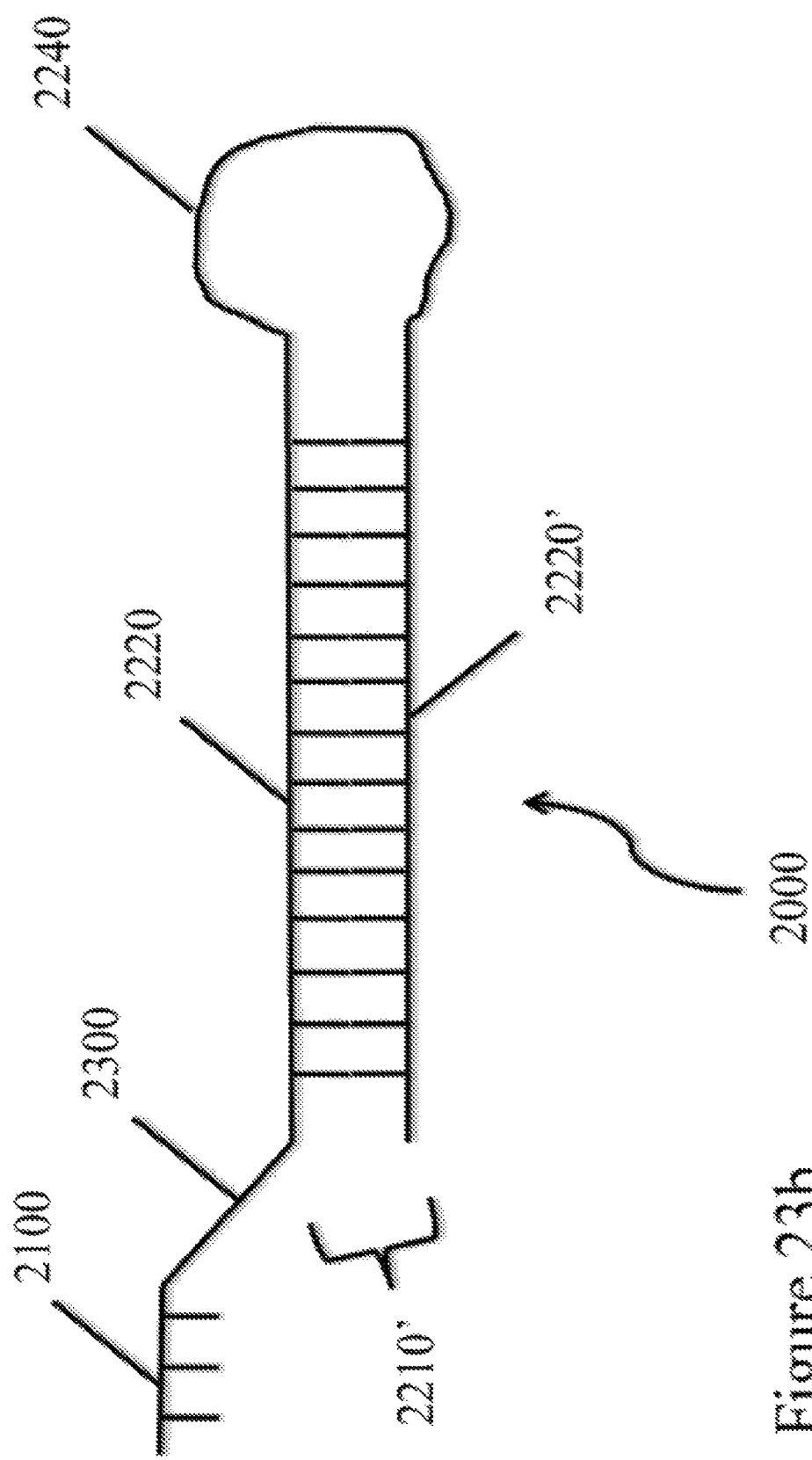
FIG. 23b is a schematic representation of the probe of FIG. 23a following annealing of the associated tag.
Figure 23C:
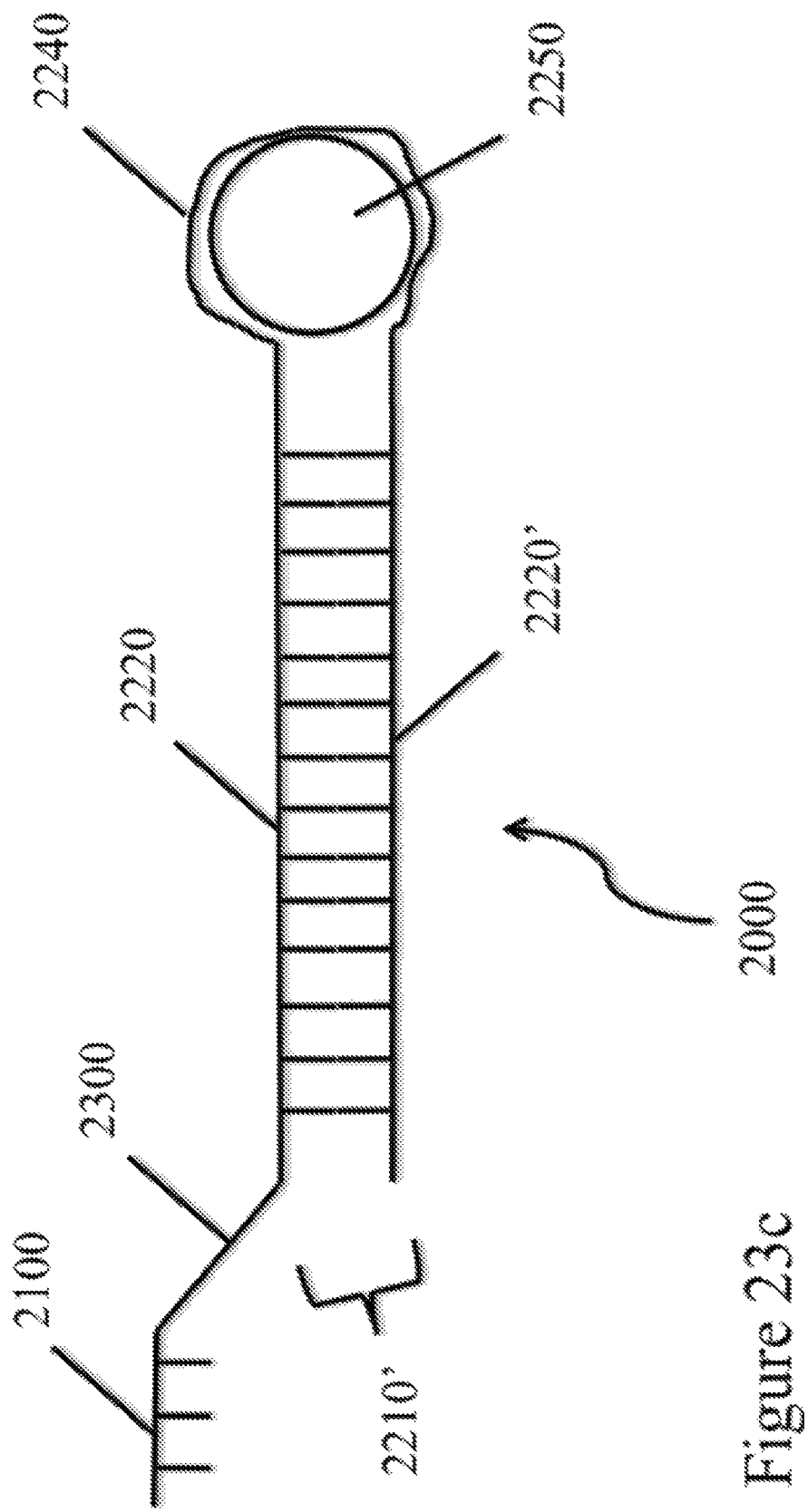
FIG. 23c is a schematic representation of the probe of FIG. 23b incorporating a detectable particle such as a gold bead.

In still another embodiment, shown in FIGS. 23a-23c, additional elements can be added to further enhance detection. Thus, as shown in FIG. 23a, the tagged probe 2000 includes a probe region 2100, a linker 2300, and a tag structure 2210' includes a first DNA region 2220 connected to a second, complementary DNA region 2220' by a loop region 2240. Unlike the structure of FIG. 22, in this case, the loop region 2240 is not DNA. As above, in FIG. 23b the complementary first 2220 and second 2220' DNA regions have been annealed to create the tag structure 2210 in the form of a DNA hairpin. Finally, as shown in FIG. 23c, a detectable particle 2250, has been inserted into the loop region 2240.

In certain embodiments, the biomolecule may be hybridized with sequence-specific probes prior to coating with protein. The probes may or may not have tags attached to them. If the probe has an attached tag composed of single- or double-stranded DNA, the protein, such as RecA, may coat the target single strand, the double-stranded regions where hybridization between target and probe has occurred, and the tag attached to the probe. Alternatively, the bound probes and associated tags may have a different affinity for the protein than for the biomolecule. If the tags have an essentially equal affinity for the protein, then both the tag and the target may be coated with protein. If the tag or probe has a greater affinity for the protein, the protein may be used to selectively coat the hybridized regions. If the tag or probe has a lower affinity for the protein, the protein may selectively coat regions of the biomolecule that do not have probe bound. Since any region with bound protein will have a larger signal, differentiation of the hybridized and non-hybridized regions allows for greater accuracy in determining the position of hybridization.

In another embodiment, protein such as RecA may be incubated with a single-stranded probe. The coated probe may then be incubated with a double-stranded target. The protein may mediate the insertion of the coated probe into the double-stranded target at positions where sequence homology exists between one of the DNA strands in the target and the sequence of the probe. The displaced strand forms a D-loop structure and the protein may remain bound to the double-stranded region of the D-loop. The target DNA containing one or more D-loop structures may be translocated through a nanopore or fluidic channel detector and the positions of hybridization determined. A higher signal may be observed at the triple-stranded region due to the increased volume occupied in the nanopore or fluidic channel.

The translocation of biomolecule/protein complexes through a nanopore or fluidic channel may include detecting an electrical signal indicative of the passage of protein coated regions. In one embodiment, the signal detected may be formed by passage of a tagged region of the biomolecule through the detector volume. The time for translocation may be indicative of the length of the biomolecule. The detection step may discriminate between protein coated, uncoated, or multiply coated regions, as a coated region may have a signal about ten times that of an uncoated region. Increased signal-to-noise may increase confidence for the detection of the probes. Positional information of probe binding to target biomolecule allows for the mapping or sequencing of the biomolecule.

EXAMPLES

The following four constructive examples describe possible scenarios in which the methods and devices described herein may be used to measure biomolecule lengths and to sequence biomolecules.

Example 1

A sensing device composed of two microfluidic chambers, one or more fluidic channels connecting the two microfluidic chambers, and two or more detector electrodes disposed along the length of each fluidic channel, is filled with an ionic fluid. Typically, the fluid may be water that contains salt.

Multiple copies of a fragment of DNA of unknown length may be introduced into one of the microfluidic chambers that is connected to the fluidic channel containing the multiple detector electrodes. Macroscopic electrodes are used to electrophoretically translocate the DNA strands from the microfluidic chamber into one or more fluidic channels. As the DNA enters the fluidic channel, it assumes a linear conformation. The degree to which it is linearized depends on a number of factors. Some of those factors are, e.g., the persistence length of the DNA strand, the temperature, the ionic conditions, and the width and depth of the fluidic channel.

The potential applied by the macroscopic electrodes causes the DNA strand to move down the length of the fluidic channel. As the fragment moves down the fluidic channel it passes through each of the detector volumes. When the leading edge of the DNA enters a detector volume, a change in some electrical characteristic such as cross channel current or potential between two detector electrodes that define the detector volume may be recorded. As the trailing edge of the DNA strand exits the detector volume, the electrical response typically returns to the value which was observed before the DNA entered the volume. The magnitude of the electrical response depends on the experimental set-up; preferably, the electrical response is equal to at least 3 times the magnitude of the root mean square noise for the system.

When the DNA enters a detector volume, an electrical signal is recorded. The signal is composed of a time stamp and an indication of which detector had changes in potential or other electrical property. The value of the electrical property may also be recorded. The value may be subtracted from the background signal or may be an absolute value. A table may be generated by a computer that lists all detector volume responses and the time stamp for each response. A computer program may subsequently determine when there has been coincident detection by determining when two or more detector volumes detect the presence of the DNA with the same time stamp. Each time that two or more detector volumes detect DNA at the same time, the time and affected detector volumes are noted. The distance between the affected detector volumes may also be recorded. Following complete translocation of the DNA fragment through all of the detector volumes in the fluidic channel, a computer program may be used to determine which of the recorded coincident detection events involved the two detector volumes with the largest distance between them.

The lower limit of the length of the DNA may be determined by calculating the distance between the two maximally separated detector volumes that indicate the presence of the DNA fragment at the same time. The upper limit of the length of the DNA fragment may be determined by calculating the distance between the closest two detector volumes that do not sense the DNA fragment at the same time during the experiment. The difference between these two distances defines the error in the measurement. Multiple copies of the same fragment may be observed independently in the same or multiple fluidic channels during the experiment.

Depending on how the distance between detector volumes is determined, a correction factor may be applied to the measured length in order to calculate the true length of the DNA fragment. For example, the distance between detector volumes may be measured by optical or electron microscopy during or after fabrication of the device. In this case, the length of the DNA calculated by the separation of the detector volumes does not take into account the incomplete linearization of the DNA in the fluidic channel. The extent of linearization may be estimated from literature values for linearization determined by optical methods on DNA in fluidic channels. If an estimated extent of linearization is 75%, the measured length can be divided by 0.75 to give the actual length.

The extent of linearization may also be determined by passing a DNA fragment of known length down the fluidic channel under the same conditions of temperature, pH, and ionic strength as the fragment of unknown length. The measured length may be used to calculate a correction factor as follows:

$$L_m/L_a = \text{Correction Factor}$$

where $L_m$ is the measured length of the fragment, and where $L_a$ is the fragment's actual, known length.

For instance, if a fragment of DNA whose known length is 143 nm is placed in the fluidic channel and the measured length of the DNA fragment is 100 nm, then the correction factor is 0.70. This indicates that under the particular set of conditions employed using the particular fluidic channel device, the extent of linearization is 70%. If an unknown fragment is measured in the same device under the same conditions and the measured length is 400 nm, then the actual length may be calculated by dividing the measured length (400 nm) by the correction factor (0.70) to obtain an actual fragment length of 571 nm. It is contemplated that single-stranded DNA and double-stranded DNA may be calibrated separately.

Rather than determining the distance between detector volumes by microscopy, the device may also be calibrated with a series of DNA fragments of known length. The fragments preferably span enough different lengths to calibrate all detector volumes that may be used in the experiment to measure the length of the unknown fragment. If DNA fragments of a known length are used to calibrate the device, no further correction factors that take into account the extent of linearization may be needed. For instance, a DNA fragment of known length 150 nm may pass through the detector volumes in the fluidic channel; the two detector volumes that are maximally separated and detect the DNA fragment at the same time may be, e.g., detector volumes 700B and 700D. When an unknown fragment passes through the fluidic channel and is also detected by, e.g., detector volumes 700B and 700D at the same time but not by any other pairs of detector volumes at a larger distance, then the length of the unknown fragment is at least 150 nm.

A mixture containing several different length fragments of DNA may be introduced into the fluidic channel. Detection in the fluidic channel allows the determination of lengths for each of the fragments in the mixture.

Example 2

A target DNA strand of known or unknown sequence may be denatured. Denaturation of the duplex DNA is typically accomplished through the application of heat or chemicals, such that the hydrogen bonds between paired strands are broken. The denatured DNA sample may be incubated with a probe of known sequence and base length or divided for incubation with multiple probes, each with their own specific recognition sequences on the target DNA. In order to hybridize the probe or probes to their recognition sequence or sequences, the conditions for the incubation are chosen such that the probe or probes bind to the known specific recognition site in preference to other sites or mismatch sites. The conditions are also chosen so that more of the probe binding sites on the denatured DNA strands are bound to a probe than unbound. The solution may be a buffered ionic solution. The solution may be agitated to facilitate binding of the probes. The temperature of the solution may be varied during the course of the incubation. For instance, the temperature of the incubation may be slowly cooled over the course of the hybridization.

Once the denatured target DNA has been hybridized with one or more probes, the sample may be introduced into a microfluidic chamber at one end of the fluidic channel device. The fluidic channel device may be filled with an ionic solution, e.g., a salt solution. The solution may also be buffered. The excess probe or probes may be removed prior to the introduction of the sample into the microfluidic chamber. Gel filtration is one method for removing short probes from a longer strand of DNA. Alternatively, other commercially available purification methods are available. Once the target DNA strand with hybridized probes has been introduced into a microfluidic chamber, a potential is applied via macroscopic electrodes to drive the DNA from the microfluidic chamber into one or more fluidic channels.

The target DNA upon entering the fluidic channel typically assumes a linearized conformation. The narrower the fluidic channel, the more linearized the DNA is forced to become. The voltage applied to the macroscopic electromotive electrodes electrophoretically drives the DNA down the fluidic channel. As the DNA and hybridized probes move down the fluidic channel they enter each of the detector volumes disposed along the fluidic channel. In this example, each detector volume includes two detector electrodes that determine the outer boundaries of the detector volume. Each pair of detector electrodes may be connected to a device that measures the potential between the two detector electrodes. The source of the potential difference between the detector electrodes is the potential applied to the macroscopic electrodes that are disposed at the ends of the fluidic channel. The value of the potential difference typically depends on the device geometry with respect to the size of the fluidic channel, the potential applied to the macroscopic electrodes, the distance between the detector electrodes in a pair, and the conductivity of the fluid-filled volume between the two detector electrodes.

In the absence of DNA, the detector volume may contain only the ionic solution and have a baseline potential difference measured between the two detector electrodes that define the detector volume. As DNA enters the detector volume, the potential measured between the two detector electrodes changes because the DNA has a conductivity different from that of the ionic solution. When DNA enters the detector volume, the conductivity of the fluidic channel between the two detector electrodes is typically reduced with respect to the conductivity when only ionic fluid is present between the detector electrodes. As DNA enters a detector volume, the change in potential or some other electrical property is measured. When a portion of the DNA that also has a probe hybridized thereto enters the detector volume, the potential changes further.

The target DNA has two or more positions where one or more probes have hybridized and is electrophoretically driven down the fluidic channel and through each of the detector volumes in the fluidic channel. As the DNA moves down the fluidic channel, the locations on the DNA to which the probes are hybridized also move through each of the detector volumes in turn. When a probe, on the target DNA enters a detector volume, an electrical signal is recorded. The electrical signal is composed of a time stamp and an indication of which detector had changes in potential or other electrical property. The value of the electrical property may also be recorded. The electrical property value may be subtracted from the background signal or may be an absolute value. A table may be generated by a computer that lists all detector volume responses and the time stamp for each response. A computer program may subsequently determine occurrences of coincident detection by determining when two or more detector volumes detect the presence of a probe on the target DNA with the same time stamp. Each time that two or more probes are disposed in detector volumes at the same time, the time and affected detector volumes are noted.

The distance between any two probes may be calculated from the distance between pairs of detector volumes that show coincident detection for that pair of probes. For instance, if two detector volumes separated by 100 nm show coincident signals for probes, then a distance of 100 nm between probes may be recorded. The greater number of different distances that exist between pairs of detector volumes in the fluidic channel, the more efficient the device may be in determining the distance between two probes.

In order to determine the distance between two detected probes, it is generally necessary to know the distance between each pair of detector volumes in which the probes are detected. This may be accomplished during fabrication of the device, at which time the position of the detector volumes may be noted. The distances may also be determined after fabrication by, e.g., electron microscopy. Finally, the distances between detector volumes may be determined by calibrating the device with known lengths of DNA or DNA having probes hybridized at known positions.

If the latter technique (calibration with a biomolecule) is used, no further correction of the measured distance between probes on the target DNA needs to be made. However, if the distance between detector volumes is determined during fabrication or by electron or optical microscopy, then a further correction to the determined distance between two probes is typically needed. This is a result of the fact that the target DNA and associated probes may not be perfectly linearized by the fluidic channel. For instance, the DNA may only be linearized by 70% in a 100 nm fluidic channel. If two detector volumes that are separated by 100 nm record coincident signals indicating the presence of probes, the recorded distance between the probes is 100 nm. However, the distance is preferably corrected for the non-perfect linearization of the DNA. In the case where the linearization is only 70%, the calculated distance between the two probes is 100 nm/0.70=143 nm.

The amount of linearization of the biomolecule may be determined from literature values or it may be obtained by calibrating the device under the conditions under which the experiment is to be run. A piece of DNA of known length may be placed in the fluidic channel and the two detector volumes having the greatest separation and recording signals indicating the presence of the DNA at the same time may be used to determine the measured length of the DNA. The correction factor may be determined by dividing the measured length by the known length. If the conditions such as ionic solution, temperature, and fluidic channel dimensions remain constant, the same correction factor may be used for every detector volume in the device. Thus, a piece of DNA that has a length of 500 nm may be placed in a device and measured to have a length of 400 nm. The correction factor for that device under the experimental conditions is 400 nm/500 nm=0.80. The correction factor of 0.80 may be used for every subsequent measurement in the device that is made under the same experimental conditions, including the calculation of distances between probes.

Example 3

A sensing device composed of two microfluidic chambers, one or more fluidic channels connecting the two microfluidic chambers, and two or more detector electrodes disposed along the length of each fluidic channel (e.g., a nanochannel), is filled with an ionic fluid. Typically, the fluid may be water that contains buffering agents or salt or both buffering agent and salt.

The sensing electrodes in the fluidic channel are disposed such that they contain two or more different volumes between each pair. As shown in FIG. 9c, the distances may be determined by a Golomb ruler. Alternatively, any spacing that results in at least two different lengths may be used. One such arrangement is shown in FIG. 10. Preferably many different lengths between sensing electrodes may be represented.

A target DNA strand is hybridized with a probe or a collection of different probes each of which preferentially binds a unique DNA sequence. The target, hybridized with probes, may be introduced into a microfluidic chamber that is connected to the fluidic channel that contains multiple detector electrodes. Macroscopic electrodes are used to electrophorese the DNA strands from the microfluidic chamber into one or more fluidic channels. Alternatively, the DNA may be pumped through the fluidic channel by pressure-induced fluid flow. As the DNA enters the fluidic channel it assumes a linear conformation. The degree to which it is linearized is dependent on a number of factors. Some of those factors are the persistence length of the DNA strand, the temperature, the ionic conditions, and the width and depth of the fluidic channel.

As the DNA fragment moves down the fluidic channel it passes through each of the detector volumes. When the leading edge of the DNA enters a detector volume, a change in some electrical characteristic such as the potential between two detector electrodes that are associated with the detector volume may be recorded. If the DNA strand is as long or longer than the distance between the two detector electrodes, then the electrical signal may reach a constant maximum value. If the DNA strand is shorter than the distance between the two electrodes, the electrical signal may be a fractional value of the maximum signal that is equal to the ratio of the DNA strand length to the length of the distance between the two detector electrodes. The maximum value may be predicted from the cross sectional area of the DNA or other analyte or may be determined with a reference DNA strand of known length that is longer than the detector volume.

When a portion of the DNA strand that has a probe hybridized enters the detecting volume, the electrical characteristic may change further. If the hybridized probe is longer than the distance between the two detector electrodes associated with the detector volume, a new maximum value may be obtained. If the probe is shorter than the distance between the two detector electrodes the new signal may be proportional to the maximum expected signal in direct relation to the ratio of the probe length to the distance between the two detector electrodes as described in the previous paragraph. If a portion of the target DNA containing two hybridized probes is contained by a single detector volume, the electrical characteristic may change by an amount that is the sum of the changes for each of the hybridized probes. The two hybridized probes 710" and 710'" in FIG. 11a are contained in a single detector volume as indicated by the two separate and additive electrical changes. When two or more probes are contained in a single detector volume the distance between the probes is less than the length of that detector volume. In FIG. 11a, the distance between probe 710" and probe 710'" is less than the distance between electrodes 115E, 115F.

The shortest distance between two detector electrodes that contains two probes places an upper limit on the measured distance between the two probes. The longest distance between two detector electrodes that does not encompass the two probes places a lower limit on the measured distance between the probes. The difference between these two distances defines the error in the measurement. Multiple copies of the same fragment may be observed independently in the same or multiple fluidic channels during the experiment.

Depending on how the distance between detector electrodes was determined, a correction factor may be applied to the measured distance in order to calculate the true distance between the probes. The distance between detector electrodes may be measured by optical or electron microscopy during or after fabrication of the device. In this case, the length of the DNA calculated by the separation of the detector electrodes does not take into account the incomplete linearization of the DNA in the fluidic channel. The extent of linearization may be estimated from literature values for linearization determined by optical methods on DNA in fluidic channels. If the estimated extent of linearization is 75% then the measured length is divided by 0.75 to give the actual length.

The extent of linearization may also be determined by passing a DNA fragment of known length down the fluidic channel under the same conditions of temperature, pH, and ionic strength as the fragment of unknown length. The measured length may be used to calculate a correction factor as described in Example 1.

The dynamic range of the detector may be determined by the number of different distances that are measured between the detector electrodes. The resolution may be determined by the amount of variation in the different distances and by the accuracy of determining the length between each detector electrode.

Example 4

Target DNA may be denatured and then hybridized with a probe or a pool of probes. Subsequent to hybridization, assembly of RecA protein into filaments around the hybridized DNA may be performed under the following conditions. The buffer pH may be between 6 and 8. The $Mg^{2+}$ concentration may be from 0-15 mM. The dithiothreitol (DTT) concentration may be 0-10 mM. The KCl concentration may be selected from a range of 0-600 mM. The concentration of ATPγS may be selected from a range of 0.1-3.0 mM. The DNA concentration may be 0.1-100 nM. The ratio of RecA monomer to DNA nucleotides, or base pairs in the case of double-stranded biomolecule, may range from 1:6 to 1:1.5. The RecA may be added all at once to the reaction or it may be added incrementally. The incubation temperature may be selected from a range from 22° C. to 40° C. The incubation time may be 10 minutes to 2.5 hours.

An exemplary set of conditions is a buffer pH of 6.2, 1 mM $Mg^{2+}$, 5 mM DTT, 50 mM KCl, 1.5 mM ATPγS, 1 nM DNA, and a 1:3.3 ratio of RecA monomer to nucleotides or base pairs. RecA is added in five equal increments at 5 minute intervals, and incubated at 37° C. for a total of 45 minutes.

Following assembly of RecA on the DNA, the sample may be diluted, buffers may be added, and/or salt may be added prior to conducting translocation experiments. The RecA bound DNA sample may be mixed with buffer containing salt. Typical final salt concentrations may be 0.2-2M KCl. For example, a final concentration can be 0.5M KCl. Other salts such as NaCl, RbCl, and KBr may be used. The salt solution on the trans side may be lower than, equal to, or greater than the concentration on the cis side of the nanopore device. An exemplary embodiment has 0.5M KCl on the cis side and 2.0M KCl on the trans side.

Figure 24:
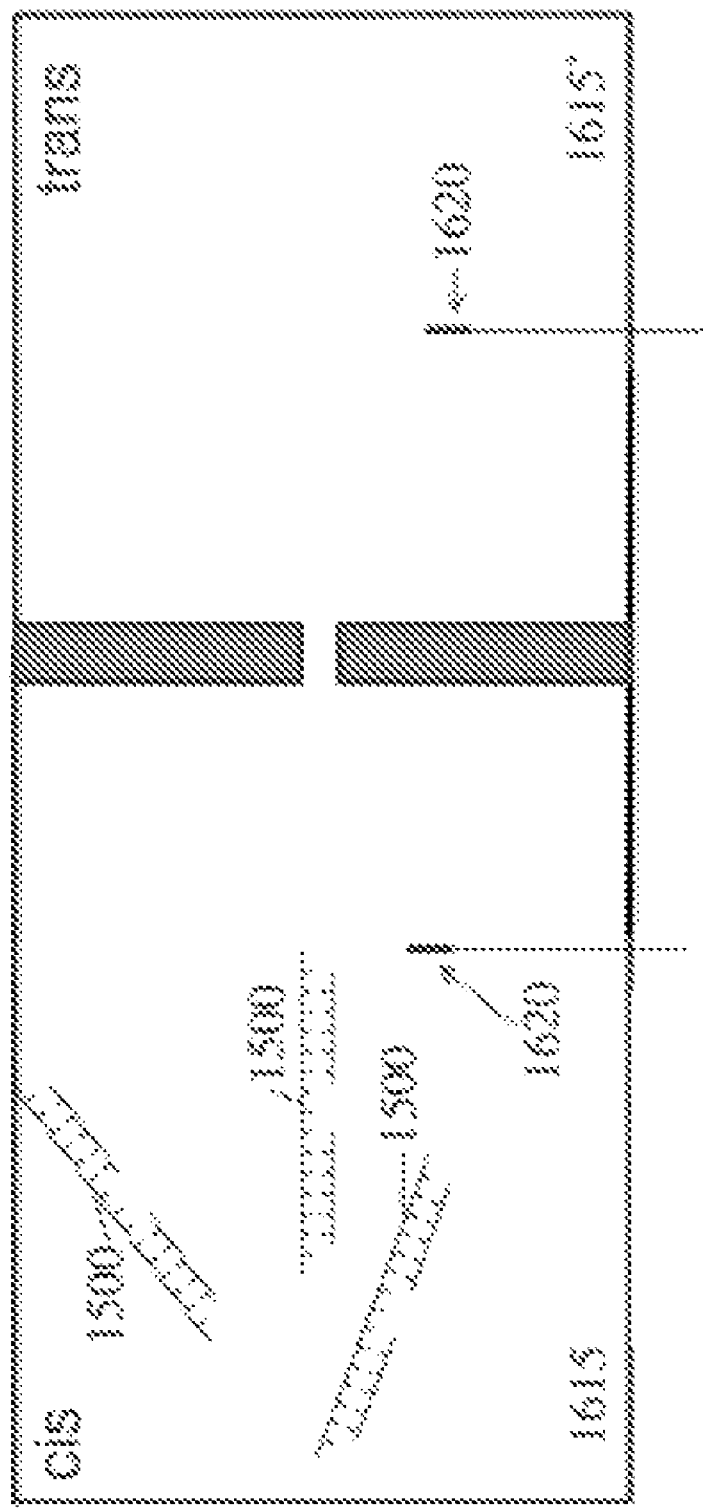
FIG. 24 is a schematic depiction of a nanopore apparatus employed in a method of an embodiment of the present invention.

In a nanopore device, the diameter of a nanopore may be selected from a range of 20-35 nm. An exemplary nanopre sequencing arrangement device as depicted in FIG. 24 may have a 30 nm nanopore and 100 μL fluid chambers. Like reference numerals in this FIG. 24 identify elements previously described with reference to FIG. 16. The device may be made of acrylic. The nanopore may be made in a 20-30 nm thick silicon nitride membrane. The sample may be placed in the cis chamber of the nanopore and translocated using standard conditions known to those skilled in the art. Electrodes, such as Ag—AgCl electrodes, may be placed about 1 mm from either side of the membrane. A constant voltage may be applied, and DNA translocation may be detected as a change in steady-state current over time using an amplifier. Operating voltages may vary from 15 mV to 400 mV. Exemplary translocation conditions may be found in, e.g., Heng, J. B.; Ho, C; Tim, T.; Timp, R.; Aksimetiev, A.; Grinkova, Y. V.; Sligar, S.; Schulten, K.; Timp, G. Sizing DNA Using a Nanometer-Diameter Pore. *Biophys. J.* 2004, 87, 2905 and Storm, A. J.; Storm, C.; Chen, J.; Zandbergen, H.; Joanny, J.-F.; Dekker, C. Fast DNA Translocation through a Solid-State Nanopore. Nano Lett. 2005, 5, 1193. The entirety of each of these references is incorporated herein by reference.

Figure 25:
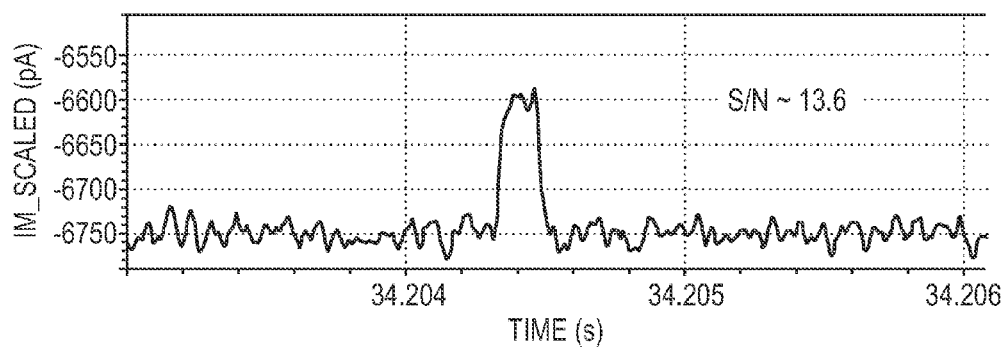
FIG. 25 is a current-versus-time trace for a double-stranded DNA of length 5.6 kbp passing through a 7 nm pore. The signal-to-noise ratio is ~13 at a filter frequency of 10 kHz.
Figure 26:
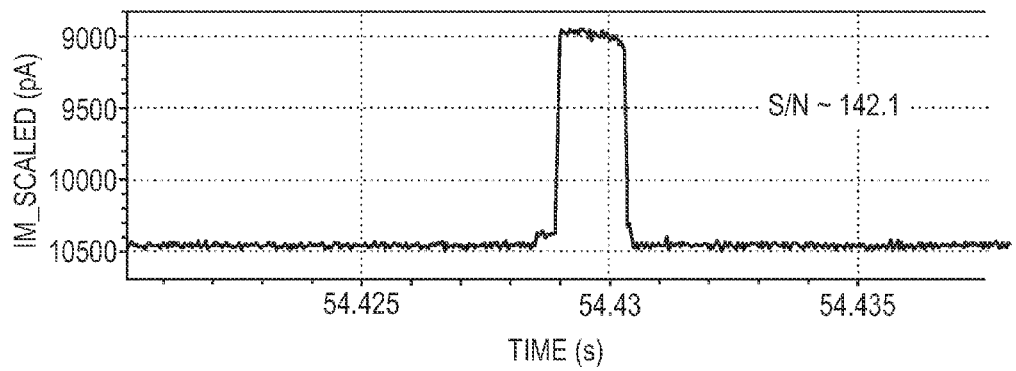
FIG. 26 is a current-versus-time trace for RecA coated double-stranded DNA of length 5.6 kbp passing through a 25 nm pore. The signal-to-noise ratio is ~142 at a filter frequency of 10 kHz.
Figure 27:
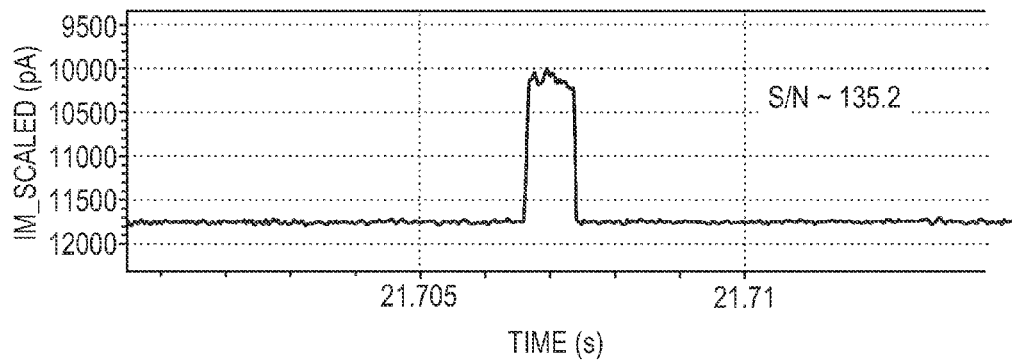
FIG. 27 is a current-versus-time trace for RecA coated single-stranded DNA of length 5.6 kbp passing through a 25 nm pore. The signal-to-noise ratio is ~135 at a filter frequency of 10 kHz.

As a reference, FIG. 25 shows the current as a function of translocation time for a double-stranded DNA not coated with protein and of length 5.6 kbp passing through a 7 nm pore. The signal-to-noise ratio is ~13 at a filter frequency of 10 kHz. FIG. 26 shows the current as a function of translocation time for RecA coated double-stranded DNA of length 5.6 kbp passing through a 25 nm pore. The signal-to-noise ratio is ~142 at a filter frequency of 10 kHz, about 10 times the signal-to-noise ratio of uncoated DNA. FIG. 27 shows the current as a function of translocation time for RecA coated single-stranded DNA of length 5.6 kbp passing through a 25 nm pore. The signal-to-noise ratio is ~135 at a filter frequency of 10 kHz. A similar increase in signal-to-noise ratio is observed for both single- and double-stranded DNA coated with RecA.

Figure 28:
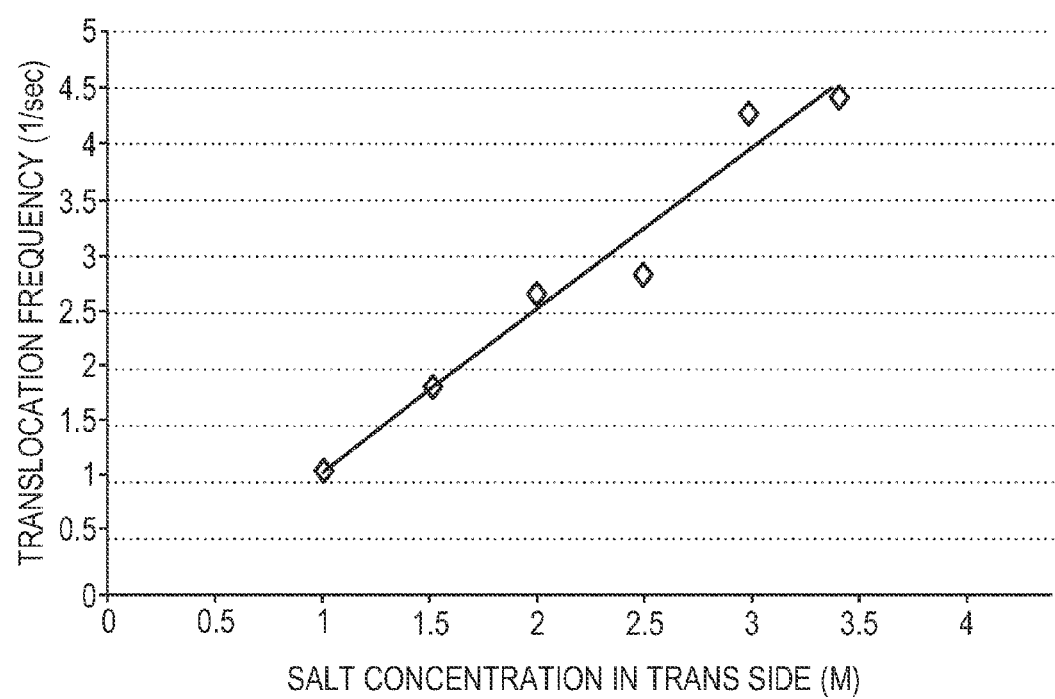
FIG. 28 depicts the effect on translocation time of varying the salt concentration on the trans side of a nanopore.

FIG. 28 depicts the effect of varying the salt concentration on the trans side of a nanopore on translocation time. The DNA concentration on the cis side was 0.5 nM, and the salt concentration was 1M KCl. The salt concentration on the trans side was varied from 1M KCl to 3.4M KCl, and the frequency of translocation events at the different salt concentrations was determined. At higher concentrations, the translocation frequency increased.

A computer may be used in the implementation of the sequencing techniques described herein. The computer can be a general purpose computer, such as a commercially available personal computer that includes a CPU, one or more memories, one or more storage media, one or more output devices, such as a display, and one or more input devices, such as a keyboard. The computer may operate using any commercially available operating system, such as any version of the Windows™ operating systems from Microsoft Corporation of Redmond, Wash., or the Linux™ operating system from Red Hat Software of Research Triangle Park, N.C. The computer is programmed with software including commands that, when operating, direct the computer in the performance of the methods of the invention. Those of skill in the programming arts will recognize that some or all of the commands can be provided in the form of software, in the form of programmable hardware such as flash memory, ROM, or programmable gate arrays (PGAs), in the form of hard-wired circuitry, or in some combination of two or more of software, programmed hardware, or hard-wired circuitry. Commands that control the operation of a computer are often grouped into units that perform a particular action, such as receiving information, processing information or data, and providing information to a user. Such a unit can comprise any number of instructions, from a single command, such as a single machine language instruction, to a plurality of commands, such as a plurality of lines of code written in a higher level programming language such as C++. Such units of commands are referred to generally as modules, whether the commands include software, programmed hardware, hard-wired circuitry, or a combination thereof. The computer and/or the software includes modules that accept input from input devices, that instruct the processing of data by the computer processor according to a set of instructions, that provide output signals to output devices, and that maintain the orderly operation of the computer. In particular, the computer may include at least one data input module that accepts information from a user interface and/or that receives data corresponding to electrical signals detected by the electrodes used in any given embodiment of the invention. The computer also includes at least one module that renders images and/or text on a display. In alternative embodiments, the computer is a laptop computer, a minicomputer, a mainframe computer, an embedded computer, or a handheld computer. The memory is any conventional memory such as, but not limited to, semi-conductor memory, optical memory, or magnetic memory. The storage medium is any conventional machine-readable storage medium such as, but not limited to, floppy disk, hard disk, CD-ROM, and/or magnetic tape. The display is any conventional display such as, but not limited to, a video monitor, a printer, a speaker, an alphanumeric display, and/or a force-feedback haptic interface device. The input device is any conventional input device such as, but not limited to, a keyboard, a mouse, a touch screen, a microphone, and/or a remote control. The computer can be a stand-alone computer or interconnected with at least one other computer by way of a network. This may be an internet connection.

Those skilled in the art will readily appreciate that all parameters listed herein are meant to be exemplary and actual parameters depend upon the specific application for which the methods and materials of the present invention are used. It is, therefore, to be understood that the foregoing embodiments are presented by way of example only and that, within the scope of the appended claims and equivalents thereto, the invention may be practiced otherwise than as specifically described.

The designs described herein merge nanopore and nanofluidic channel technologies and decouple the driving electrophoretic force from the detected signal. By using voltage sensing and by fabricating voltage amplifiers directly on the substrate where the nanoscale electrodes are placed, the device may operate at higher frequencies than has been possible with previous geometries.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. An apparatus for analyzing a target biomolecule, the apparatus comprising:
   a) first and second fluid chambers in fluid communication with one another, wherein the first and second fluid chambers are separated by a structure defining a member selected from the group consisting of a nanochannel and a microchannel;
   b) a plurality of electrodes each laterally offset from one another along at least a portion of a length of the nanochannel or microchannel, to thereby define a plurality of detector volumes therein, the electrodes being in communication with an electrical signal detector and data collection device programmed to respectively detect and record changes in an electrical property corresponding to at least one of the detector volumes as the target biomolecule translocates through the detector volumes, wherein (i) each detector volume is defined by a pair of the electrodes laterally offset from each other along the nanochannel or microchannel, (ii) each pair of laterally offset electrodes comprises a first electrode disposed upstream from a second electrode along a length of the nanochannel or microchannel, and (iii) the plurality of electrodes comprises at least three electrodes defining at least two detector volumes therebetween; and
   c) a driving force generator for translocating the target biomolecule from the first fluid chamber to the second fluid chamber through the plurality of detector volumes.

2. The apparatus of claim 1, wherein the plurality of electrodes comprises a first plurality of n electrodes each laterally offset by a first predetermined distance along the nanochannel or microchannel, to thereby define n−1 detector volumes.

3. The apparatus of claim 2, having a second plurality of m electrodes each laterally offset by a predetermined distance along the nanochannel or microchannel, to thereby define m−1 detector volumes.

4. The apparatus of claim 3, wherein the second plurality of electrodes is laterally offset from the first plurality of electrodes by a distance greater than either the first or second predetermined distance.

5. The apparatus of claim 1, wherein a spacing between each detector volume is predetermined and unequal.

6. The apparatus of claim 5, wherein the spacings between the plurality of detector volumes define a Golomb ruler.

7. The apparatus of claim 1, wherein spacings between the detector electrodes of at least two detector volumes are unequal.

* * * * *

```
                            SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tatcgaccgt                                                          10

<210> SEQ ID NO 2
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttctagatt ctag                                                     14

<210> SEQ ID NO 3
<211> LENGTH: 14
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
cuucuagauu cuag                                                     14
```